United States Patent
Bharadwaj et al.

(10) Patent No.: US 10,576,303 B2
(45) Date of Patent: *Mar. 3, 2020

(54) METHODS AND SYSTEMS FOR BEAM INTENSITY-MODULATION TO FACILITATE RAPID RADIATION THERAPIES

(71) Applicant: The Board of Trustees of the Leland Stanford Junior University, Stanford, CA (US)

(72) Inventors: Vinod Bharadwaj, Stanford, CA (US); Valery A. Dolgashev, San Carlos, CA (US); Rebecca Fahrig, Moehrendorf (DE); Billy Wiseman Loo, Foster City, CA (US); Peter G. Maxim, Palo Alto, CA (US); Sami Tantawi, Stanford, CA (US); Cecile Limborg, Palo Alto, CA (US); Ludovic Nicolas, Menlo Park, CA (US)

(73) Assignee: The Board of Trsutees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/896,407

(22) Filed: Feb. 14, 2018

(65) Prior Publication Data
US 2018/0236269 A1    Aug. 23, 2018

Related U.S. Application Data

(60) Division of application No. 15/068,387, filed on Mar. 11, 2016, now Pat. No. 9,931,522, which is a
(Continued)

(51) Int. Cl.
*A61N 5/10* (2006.01)
*H05H 9/04* (2006.01)
(Continued)

(52) U.S. Cl.
CPC ......... *A61N 5/1084* (2013.01); *A61N 5/1039* (2013.01); *A61N 5/1043* (2013.01);
(Continued)

(58) Field of Classification Search
CPC .. A61N 5/1084; A61N 5/1039; A61N 5/1043; A61N 5/1045; A61N 5/1064;
(Continued)

(56) References Cited

U.S. PATENT DOCUMENTS

| 3,757,118 A | 9/1973 | Hodge et al. |
| 4,644,168 A | 2/1987 | Rand et al. |

(Continued)

FOREIGN PATENT DOCUMENTS

| CN | 101453951 | 6/2009 |
| EP | 1358908 | 11/2003 |

(Continued)

OTHER PUBLICATIONS

Bazalova et al., "WE-C-BRB-05: Monte Carlo Simulations and Experimental Validation of Rapid Dose Delivery with Very High-Energy Electron Beams", Medical Physics, vol. 39, No. 6, Jun. 2012, p. 3944.
(Continued)

*Primary Examiner* — David E Smith
(74) *Attorney, Agent, or Firm* — Kilpatrick Townsend & Stockton LLP

(57) ABSTRACT

Methods and system for facilitating rapid radiation treatments are provided herein and relate in particular to radiation generation and delivery, electron source design, beam control and shaping/intensity-modulation. The methods and systems described herein are particularly advantageous when used with a compact high-gradient, very high energy electron (VHEE) accelerator and delivery system (and related processes) capable of treating patients from multiple
(Continued)

beam directions with great speed, using all-electromagnetic or radiofrequency deflection steering is provided; or when used with a high-current electron accelerator system of energy range more conventionally used in photon radiation therapy to produce much faster delivery of intensity-modulated photon radiation therapy, that can in both cases deliver an entire dose or fraction of high-dose radiation therapy sufficiently fast to freeze physiologic motion, yet with an equal or better degree of dose conformity or sculpting compared to conventional photon therapy.

21 Claims, 32 Drawing Sheets

Related U.S. Application Data continuation of application No. PCT/US2014/055252, filed on Sep. 11, 2014.

(60) Provisional application No. 61/876,679, filed on Sep. 11, 2013.

(51) Int. Cl.
*A61N 7/02* (2006.01)
*H05H 7/04* (2006.01)

(52) U.S. Cl.
CPC ......... *A61N 5/1045* (2013.01); *A61N 5/1064* (2013.01); *A61N 5/1067* (2013.01); *A61N 5/1078* (2013.01); *A61N 5/1081* (2013.01); *A61N 7/02* (2013.01); *H05H 9/048* (2013.01); *A61N 2005/1055* (2013.01); *A61N 2005/1058* (2013.01); *A61N 2005/1076* (2013.01); *A61N 2005/1089* (2013.01); *A61N 2005/1091* (2013.01); *A61N 2005/1098* (2013.01); *H05H 2007/048* (2013.01)

(58) Field of Classification Search
CPC .. A61N 5/1067; A61N 5/1078; A61N 5/1081; A61N 7/02; A61N 2005/1055; A61N 2005/1058; A61N 2005/1076; A61N 2005/1089; A61N 2005/1091; A61N 2005/1098; H05H 9/048; H05H 2007/048

See application file for complete search history.

(56) References Cited

U.S. PATENT DOCUMENTS

| | | | |
|---|---|---|---|
| 4,726,046 A | 2/1988 | Nunan et al. | |
| 4,737,647 A | 4/1988 | Stieber et al. | |
| 4,827,491 A | 5/1989 | Barish | |
| 5,452,720 A | 9/1995 | Smith et al. | |
| 5,661,377 A | 8/1997 | Mishin et al. | |
| 5,684,854 A | 11/1997 | Hughes | |
| 5,729,584 A | 3/1998 | Moorman et al. | |
| 5,847,401 A | 12/1998 | Davies et al. | |
| 5,859,893 A | 1/1999 | Moorman et al. | |
| 6,332,017 B1 | 12/2001 | Carroll et al. | |
| 6,333,966 B1 | 12/2001 | Schoen et al. | |
| 6,353,227 B1 | 3/2002 | Boxen | |
| 6,459,762 B1 | 10/2002 | Wong et al. | |
| 6,463,123 B1 | 10/2002 | Korenev | |
| 6,537,052 B1 | 3/2003 | Adler | |
| 6,559,610 B2 | 5/2003 | Tanaka et al. | |
| 6,628,750 B1 | 9/2003 | Korenev | |
| 6,714,620 B2 | 3/2004 | Caflisch et al. | |
| 6,724,782 B2 | 4/2004 | Hartemann et al. | |
| 6,728,335 B1 | 4/2004 | Thomson et al. | |
| 6,768,265 B1 | 7/2004 | Ives et al. | |
| 6,794,656 B2 | 9/2004 | Francke et al. | |
| 6,847,168 B1 | 1/2005 | Ives et al. | |
| 6,937,693 B2 | 8/2005 | Svatos et al. | |
| 6,977,987 B2 | 12/2005 | Yamashita et al. | |
| 7,085,347 B2 | 8/2006 | Mihara et al. | |
| 7,164,748 B2 | 1/2007 | Francke | |
| 7,167,540 B2 | 1/2007 | Muller et al. | |
| 7,180,243 B2 | 2/2007 | Secheresse et al. | |
| 7,190,764 B2 | 3/2007 | Mori et al. | |
| 7,206,379 B2 | 4/2007 | Lemaitre et al. | |
| 7,385,354 B2 | 6/2008 | Miyake | |
| 7,391,850 B2 | 6/2008 | Kaertner et al. | |
| 7,486,775 B2 | 2/2009 | Forster et al. | |
| 7,601,966 B2 | 10/2009 | Ben-haim et al. | |
| 7,630,474 B2 | 12/2009 | Clayton | |
| 7,741,624 B1 | 6/2010 | Sahadevan et al. | |
| 7,816,870 B2 | 10/2010 | Yakovlev et al. | |
| 7,835,492 B1 | 11/2010 | Sahadevan et al. | |
| 7,838,838 B2 | 11/2010 | Rousso et al. | |
| 7,839,972 B2 | 11/2010 | Ruchala et al. | |
| 8,027,431 B2 | 9/2011 | Stahl et al. | |
| 8,039,819 B2 | 10/2011 | Faure et al. | |
| 8,173,983 B1 | 5/2012 | Sahadevan et al. | |
| 8,232,748 B2 | 7/2012 | Treas et al. | |
| 8,315,357 B2 | 11/2012 | Zhu et al. | |
| 8,350,226 B2 | 1/2013 | Zdasiuk et al. | |
| 8,405,044 B2 | 3/2013 | MacKinnon et al. | |
| 8,547,006 B1 | 10/2013 | Ives et al. | |
| 8,575,579 B2 | 11/2013 | Moskvin et al. | |
| 8,610,075 B2 | 12/2013 | Rousso et al. | |
| 8,618,521 B2 | 12/2013 | Loo | |
| 8,624,496 B2 | 1/2014 | Neubauer et al. | |
| 8,674,630 B1 | 3/2014 | Cornelius | |
| 8,787,529 B2 | 7/2014 | Graves et al. | |
| 9,018,603 B2* | 4/2015 | Loo | A61N 5/1065 250/492.1 |
| 9,155,910 B1 | 10/2015 | Sahadevan | |
| 9,470,801 B2 | 10/2016 | Ziv et al. | |
| 9,804,104 B2 | 10/2017 | Libman et al. | |
| 9,931,522 B2 | 4/2018 | Bharadwaj et al. | |
| 9,962,562 B2 | 5/2018 | Fahrig et al. | |
| 2002/0191746 A1 | 12/2002 | Dinsmore et al. | |
| 2004/0044265 A1 | 3/2004 | Muller et al. | |
| 2004/0079899 A1 | 4/2004 | Ma | |
| 2004/0082855 A1 | 4/2004 | Robar et al. | |
| 2004/0140432 A1 | 7/2004 | Maldonado et al. | |
| 2006/0001855 A1 | 1/2006 | Lof et al. | |
| 2006/0106301 A1 | 5/2006 | Kats et al. | |
| 2007/0051905 A1* | 3/2007 | Fujimaki | G21K 1/043 250/492.3 |
| 2007/0152610 A1 | 7/2007 | Yakovlev et al. | |
| 2007/0265230 A1 | 11/2007 | Rousso et al. | |
| 2008/0001090 A1 | 1/2008 | Ben-haim et al. | |
| 2008/0002811 A1 | 1/2008 | Allison et al. | |
| 2008/0049897 A1 | 2/2008 | Molloy | |
| 2008/0298401 A1 | 12/2008 | Faure et al. | |
| 2009/0185656 A1 | 7/2009 | Heuscher | |
| 2009/0212231 A1 | 8/2009 | Hill et al. | |
| 2009/0225932 A1 | 9/2009 | Zhu et al. | |
| 2009/0252291 A1* | 10/2009 | Lu | A61N 5/1049 378/65 |
| 2009/0296885 A1* | 12/2009 | Boeh | A61N 5/1042 378/65 |
| 2010/0001200 A1 | 1/2010 | Ben-haim et al. | |
| 2010/0174180 A1 | 7/2010 | Rousso et al. | |
| 2010/0207042 A1 | 8/2010 | Harada et al. | |
| 2010/0228116 A1 | 9/2010 | Lu et al. | |
| 2010/0246767 A1 | 9/2010 | Tanabe | |
| 2010/0260317 A1 | 10/2010 | Chang et al. | |
| 2011/0073778 A1 | 3/2011 | Natori et al. | |
| 2011/0093243 A1 | 4/2011 | Tawhai et al. | |
| 2011/0206187 A1 | 8/2011 | Lee et al. | |
| 2011/0254443 A1 | 10/2011 | Neubauer et al. | |
| 2011/0266464 A1 | 11/2011 | Takai et al. | |
| 2012/0022363 A1 | 1/2012 | Dempsey | |
| 2012/0085916 A1 | 4/2012 | Clayton et al. | |
| 2012/0262333 A1 | 10/2012 | Trummer et al. | |
| 2012/0305796 A1* | 12/2012 | Iseki | G01T 1/2935 250/396 R |
| 2012/0326636 A1 | 12/2012 | Eaton et al. | |
| 2013/0016814 A1 | 1/2013 | Treas et al. | |

(56) References Cited

U.S. PATENT DOCUMENTS

| | | | |
|---|---|---|---|
| 2013/0035587 | A1 | 2/2013 | Lagendijk et al. |
| 2013/0172657 | A1 | 7/2013 | Meier et al. |
| 2013/0231516 | A1 | 9/2013 | Loo et al. |
| 2013/0287167 | A1 | 10/2013 | Gum et al. |
| 2014/0010351 | A1 | 1/2014 | Rommel |
| 2014/0037541 | A1 | 2/2014 | Rousso et al. |
| 2014/0135563 | A1 | 5/2014 | Loo et al. |
| 2014/0371581 | A1 | 12/2014 | Mostafavi et al. |
| 2015/0070029 | A1 | 3/2015 | Libman et al. |
| 2015/0087881 | A1 | 3/2015 | Takao et al. |
| 2016/0014876 | A1 | 1/2016 | Tantawi et al. |
| 2016/0193481 | A1 | 7/2016 | Tantawi et al. |
| 2016/0193482 | A1 | 7/2016 | Fahrig et al. |
| 2016/0310764 | A1 | 10/2016 | Bharadwaj et al. |

FOREIGN PATENT DOCUMENTS

| | | |
|---|---|---|
| WO | 2005115544 | 12/2005 |
| WO | 2007140090 | 12/2007 |
| WO | 2011127946 | 10/2011 |
| WO | 2012025261 | 3/2012 |
| WO | 2013133936 | 9/2013 |
| WO | 2014055989 | 4/2014 |
| WO | 2015038832 | 3/2015 |
| WO | 2015102680 | 7/2015 |
| WO | 2015102681 | 7/2015 |

OTHER PUBLICATIONS

Brahme et al., "Electron and Photon Beams from a 50 MeV Racetrack Microtron", Acta Oncologica. vol. 19. No. 4, Jan. 1, 1980, pp. 305-319.

Caryotakis, "Development of X-band Klystron Technology at SLAG", Proceedings of the 1997 Particle Accelerator Conference, vol. 3, May 1997, pp. 2894-2898.

Desrosiers et al., "150-250 MeV electron beams in radiation therapy", Physics in Medicine and Biology, vol. 45, No. 7, 2000, pp. 1781-1805.

Desrosiers et al., "An evaluation of very high energy electron beams (up to 250 MeV) in radiation therapy", Purdue University, Dec. 2004, 163 pages.

Dolgashev et al., "Geometric dependence of radio-frequency breakdown in normal conducting accelerating structures", Applied Physics Letters, vol. 97, No. 17, 2010, (http://apl.aip.org/resource/1/applab/v97/i17/p171501_s1).

Fuchs, "Laser-accelerated particles: Investigations towards applications in radiotherapy", Retrieved from internet: http://www.ub.uni-heidelberg.de/archiv/7452, 2007, 152 pages.

Fuchs et al., "Treatment planning for laser-accelerated very-high energy electrons", Physics in Medicine and Biology vol. 54, No. 11, 2009, pp. 3315-3328.

Furukawa et al., "Design study of a raster scanning system for moving target irradiation in heavy-ion radiotherapy", Medical Physics, vol. 34, No. 3, Mar. 2007, 1085-1097.

Glinec et al., "Radiotherapy with laser-plasma accelerators: Monte Carlo simulation of dose deposited by an experimental quasimonoenergetic electron beam", Medical Physics, vol. 33, No. 1, Jan. 2006, pp. 155-162.

Howell et al., "Measurements of secondary neutron dose from 15 MV and 18 MV IMRT", Radiation Protection Dosimetry, vol. 115, issues 1-4, 2005, pp. 508-512, abstract only.

Neilson et al., "Design of RF feed system and cavities for standing-wave accelerator structure", Nuclear Instruments and Methods in Physics Research A: Accelerators, Spectrometers, Detectors and Associated Equipment, vol. 657, issue 1, Nov. 2011, pp. 52-54, abstract only.

Palowitz et al., "MCNPX 2.7.E Extension", Los Alamos National Laboratory report LA-UR-11-01502, Mar. 2011, draft of later publication Palowitz, Denise B. et al., "MCNPX User's Manual, Version 2. 7.0," Los Alamos National Laboratory report LA-CP-11-00438, Apr. 2011, (http://mcnpx.lanl.gov/documents.html).

Papaconstadopoulos et al., "WE-C-BRB-04: Fast and Accurate Hybrid Source Model for Modulated Electron Radiotherap", Medical Physics, vol. 39, No. 6, Jun. 2012, p. 3944.

International Search Report and Written Opinion dated Apr. 19, 2013 received in International Patent Application No. PCT/US2013/025765, 20 pages.

International Search Report and Written Opinion dated Jul. 9, 2015 received in International Patent Application No. PCT/US2014/055252, 8 pages.

International Search Report and Written Opinion dated Jul. 2, 2015 received in International Patent Application No. PCT/US2014/055260, 7 pages.

International Search Report and Written Opinion dated Jan. 27, 2015 received in International Patent Application No. PCT/US2014/055270, 16 pages.

Schneider et al., "Secondary neutron dose during proton therapy using spot scanning,", International Journal of Radiation Oncology Biology Physics, vol. 53, issue 1, 2002, pp. 244-251, abstract only.

Tantawi et al., "rf distribution system for a set of standing-wave accelerator structures", Physical Review Special Topics—Accelerators and Beams, vol. 9, No. 11, Nov. 2006, pp. 112001-1-112001-6.

Ulmer, "On the Creation of High Energy Bremsstrahlung and Intensity by a Multitarget and Repeated Focusing of the u Scattered Electrons by a Small-Angle Backscatter at the Wall of a Cone and Magnetic Fields—A Possible Way to Improve Linear Accelerators in Radio . . . ", Radiation Physics and Chemistry 81, 2012, pp. 387-402.

Walters et al., "DOSXYZnrc Users Manual", Ionizing Radiation Standards National Research Council of Canada, Retrieved from Internet: http://irs.inms.nrc.ca/software/beamnrc/documentation/pirs794, 2001, pp. 1-109.

Yeboah et al., "Optimization of intensity-modulated very high energy (50-250 MeV) electron therapy", Physics in Medicine and Biology, vol. 47, No. 8, 2002, pp. 1285-1301.

Yeboah et al., "Optimized treatment planning for prostate cancer comparing IMPT, VHEET and 15 MV IMXT", Physics in Medicine and Biology, vol. 47, No. 13, Jun. 2002, pp. 2247-2261.

\* cited by examiner

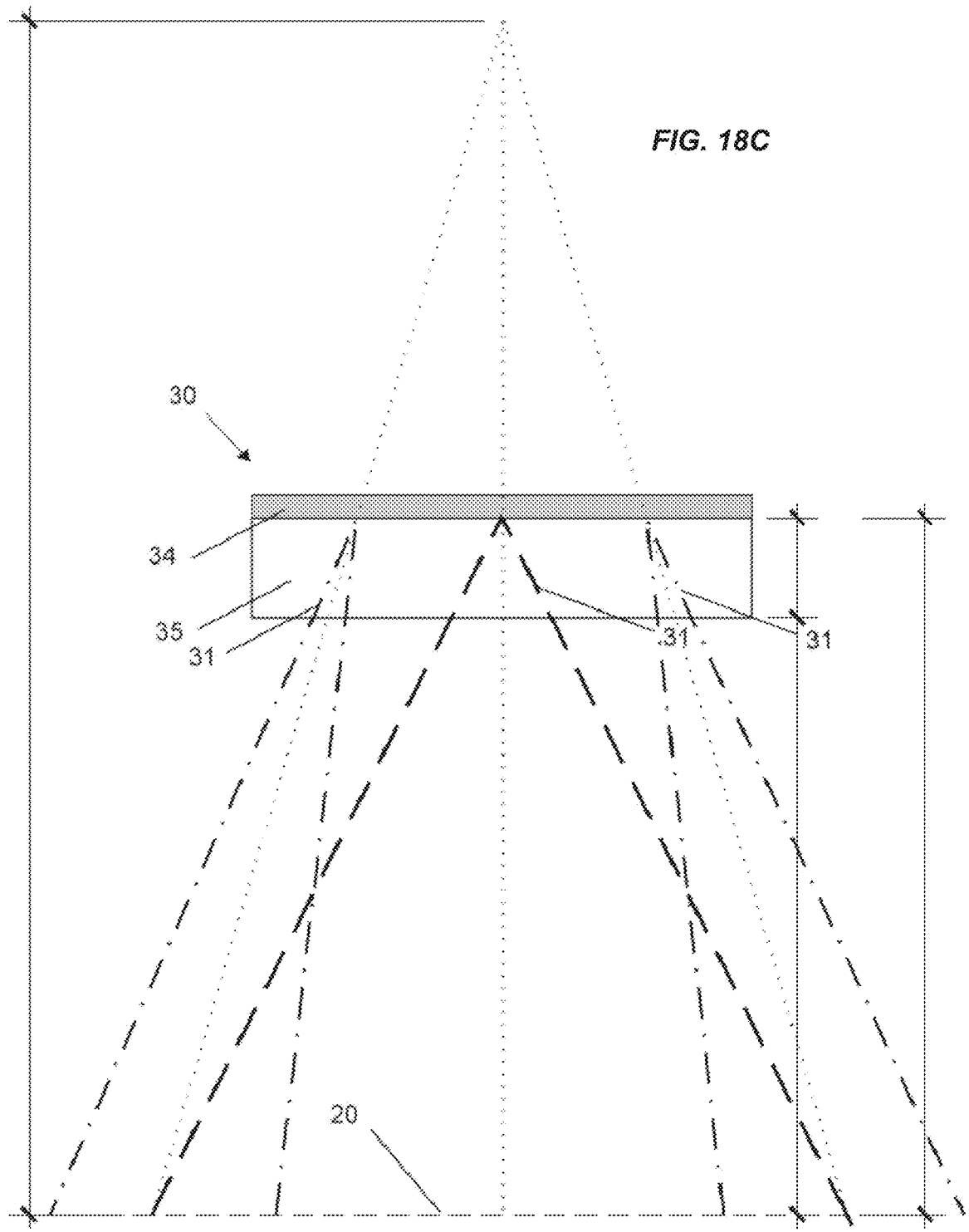

METHODS AND SYSTEMS FOR BEAM INTENSITY-MODULATION TO FACILITATE RAPID RADIATION THERAPIES

CROSS-REFERENCES TO RELATED APPLICATIONS

The present application is a Divisional of U.S. Ser. No. 15/068,387 filed Mar. 11, 2016 (Allowed); which is a continuation of PCT/US2014/055252 filed Sep. 11, 2014; which claims priority to U.S. Provisional Application No. 61/876,679 filed Sep. 11, 2013; the entire contents of which are incorporated herein by reference in their entirety for all purposes.

This application is generally related to U.S. application Ser. No. 13/765,017 entitled "Pluridirectional Very High Electron Energy Radiation Therapy Systems and Processes," filed Feb. 12, 2013 (now U.S. Pat. No. 8,618,521); PCT Application No. PCT/US2014/055260 filed Sep. 11, 2014; and PCT Application No. PCT/US2014/055270 filed Sep. 11, 2014; the full disclosures of which are incorporated herein by reference in their entirety for all purposes.

FIELD OF THE INVENTION

The invention generally relates to radiation therapies and more particularly to systems and methods for very rapid radiation therapies.

BACKGROUND OF THE INVENTION

Major technical advances in radiation therapy in the past two decades have provided effective sculpting of 3-D dose distributions and spatially accurate dose delivery by imaging verification. These technologies, including intensity modulated radiation therapy (IMRT), hadron therapy, and image guided radiation therapy (IGRT) have translated clinically to decreased normal tissue toxicity for the same tumor control, and more recently, focused dose intensification to achieve high local control without increased toxicity, as in stereotactic ablative radiotherapy (SABR) and stereotactic body radiotherapy (SBRT).

One key remaining barrier to precise, accurate, highly conformal radiation therapy is patient, target and organ motion from many sources including musculoskeletal, breathing, cardiac, organ filling, peristalsis, etc. that occurs during treatment delivery, currently 15-90 minutes per fraction for state-of-the-art high-dose radiotherapy. As such, significant effort has been devoted to developing "motion management" strategies, e.g., complex immobilization, marker implantation, respiratory gating, and dynamic tumor tracking.

BRIEF SUMMARY OF THE INVENTION

The present invention relates to methods and systems for facilitating radiation therapies, particularly extremely rapid radiation therapies that rapidly deliver a radiation treatment sufficiently fast enough to freeze physiologic motion.

In one aspect, the invention relates to a method for treating a patient, that includes: generating one or more patterned particle beams, each patterned particle, wherein each of the one or more patterned particle beams covers an area of the targeted tissue with spatially varying beam intensity according to a treatment pattern of desired radiation dose distribution; accelerating the one or more patterned particle beams with one or more accelerators; and transporting and/or magnifying the patterned beam to a desired location, direction, and size suitable for coverage of the targeted tissue, wherein a shape, resolution and contrast of the pattern is suitably maintained during transport and/or magnification so as to deliver the desired radiation dose distribution to the targeted tissue according to the treatment pattern. Magnifying the patterned beam may include magnifying the beam through one or more focusing elements disposed within the beamline of the one or more beams, such as by 100 to 200 times the original size of the pattern. The focusing elements may include electro-magnetic lenses, one or more permanent magnets, electromagnets or a combination thereof. Such methods may further include steering the one or more patterned particle beams to the targeted tissue with one or more beam steering devices from one or more directions. In some embodiments, steering is concurrent with magnifying of the one or more patterned particle beams. Methods may further including forming the two-dimensional intensity-modulated electron pattern on a photocathode by projecting or scanning a light source onto the photocathode.

In certain aspects, the one or more patterned particle beams comprise an array of smaller patterned beams produced by raster scanning individual smaller patterned beams from each beam direction of the one or more directions.

In another aspect, the invention relates to systems for treating a patient, that include: one or more beam generation devices configured to generate one or more patterned particle beams, each of the one or more particle beams covering an area of the targeted tissue with spatially varying beam intensity according to a treatment pattern of desired radiation dose distribution; one or more accelerators configured for accelerating the one or more patterned particle beams; and one or more magnification lenses along a beam line of the one or more particle beams between the accelerators and targeted tissue for magnification of the patterned particle beam to a desired size suitable for coverage of the targeted tissue according to the treatment pattern. The system may include one or more beam steering devices configured for steering the one or more patterned particle beams to the targeted tissue from one or more directions, which may be before or concurrent with magnifying the beam with one or more lenses, such as with a plurality of small aperture magnetic lenses.

In some embodiments, the system includes a beam deflector disposed along beamlines of the one or more particle beams between the one or more accelerators and the targeted tissue such that the one or more beam lines can be directed to the targeted tissue from multiple differing angles using a single common accelerator. The system may be configured to generate the one or more patterned particle beams from an array of smaller patterned beams by raster scanning. The system may be configured such that raster scanning occurs prior to the accelerator while the beam has a low energy. Raster scanning may be performed by deflection of a fixed position electron source or by rastering a laser spot on a photocathode.

In certain embodiments, the system includes an RF powered or DC particle gun and a photo-cathode configured to produce the two-dimensional intensity-modulated electron pattern. The system may include a programmable controller configured to control deliver the one or more particle beams to the targeted tissue from the one or more directions thereby irradiating the targeted tissue to deliver an entire treatment dose in less than 10 seconds, preferably about one second or less. The controller is configured to rapidly switch a modulation pattern sent to the photocathode within a rate of one pattern every 2 seconds or higher so as to provide delivery of differing treatment patterns to the targeted tissue from multiple directions within less than 10 seconds or less. In one aspect, the system is dimensioned so as to operate within a standard sized treatment room. In another aspect, the treatment pattern is adapted so as to be suitable for use in a non-medical application, such as cargo scanning or non-destructive scanning.

In another aspect, the invention relates to a photon collimation assembly that includes: one or more photon generating layer; and a substantially planar collimator block having an upstream side towards an electron source when included in a treatment system for treating a targeted tissue and downstream side towards the targeted tissue, the upstream side being disposed adjacent the photon generating layer, wherein the collimator block includes a plurality of channels, each extending from an inlet opening at the upstream side to an outlet opening at the downstream side of the collimator block, wherein the channels and outlet openings and a thickness of the block are dimensioned so as to suitably maintain resolution and contrast of an intensity-modulation pattern of a beam when collimated through the channels. In some embodiments, suitably maintaining resolution of the pattern entails maintaining a resolution of the treatment pattern at the original size within $1/10$ of a width of the overall pattern or smaller, such as $1/100$ of a width of the overall pattern.

In some embodiments, each of the channels of the collimation assembly has a substantially square cross-section throughout, while in other embodiments, each of the channels has a non-square cross-section optimized to produce specific beamlet shapes. The channels may be arranged on a rectangular or non-rectangular grid, the channels traverse the block at angles substantially perpendicular to the upstream and downstream faces of the block, or the channels traverse the block at angles substantially oblique to the upstream and downstream faces of the block. In one aspect, the assembly collimates without requiring movement of any mechanically moving parts.

In certain embodiments, a spacing between outlet openings of the channels of the collimation assembly is sufficiently small that a penumbra of individual beams transmitted through the channels fills a dosimetric gap in the targeted tissue between beamlets when used to treat the targeted tissue. In some embodiments, the spacing may be such that the adjacent beamlets overlap at the target. In one aspect, the openings and thickness of the collimator are dimensioned so that a penumbra of individual beams transmitted through the channels is sufficiently sharp to provide sufficient resolution to maintain an intensity-modulation pattern of the beams when transmitted through the channels. In some embodiments, the outlet opening is substantially larger than the inlet opening for each of the plurality of channels.

In some embodiments, the collimation assembly includes a photon generating target consists of individual target material plugs aligned over the corresponding channels of the collimator array embedded within a layer of heat conducting material situated at the upstream side of the collimator array. In certain embodiments, the collimation assembly includes an active cooling feature, such as cooling through flow of water or air through a portion of the collimator or component thermally coupled with the collimator assembly.

In another aspect, collimation assembly may be provided in a treatment positioned in beamline or may be include in a set of differing collimation assemblies. In some embodiments, a treatment system includes a rotating gantry on which one or more beamlines are mounted along with one or more collimation assemblies such that collimated beams can be directed to the target tissue from multiple directions by rotating the gantry. In another aspect, a system may include a carousel of differing collimation assembly that rotates so as to position as select collimation assembly in a desired beamline for treatment.

In one aspect, the system includes a combination of steering magnets, permanent magnets or electromagnets and accelerator assembled in a compact instrument delivering medium range energy electron bunches with a controlled intensity profile at a desired central target, and duplicable to cover a minimum number of incoming angles (e.g. 16) distributed around the target, and contained within a standard treatment room size. Typically, a standard treatment room size, such as about 20×20 feet wide and 10 feet high. Transport, magnification and delivery of the desired electron beam at the central target is achieved by combining steering, optical magnification, emittance preservation by means of a minimum number of magnets. In some embodiments, steering is performed concurrent with magnification, thereby allowing further reduction in size of the system.

Delivery of radiation therapies in significantly reduced time-scale as compared to convention methods poses a number of difficulties, many of which are addressed by the methods and systems described herein. For example, aspects relating to targeted tissue motion, radiation beam generation and steering, power production and distribution, radiation source design, radiation beam control and shaping/intensity-modulation, treatment planning, imaging and dose verification present various challenges and, as used in conventional therapies, barriers to delivering radiation therapies to targeted tissues on a significantly reduced time scale. While the methods and systems described herein may be used to facilitate very rapid radiation therapies, particularly by addressing the above noted aspects of radiation delivery therapies, it is understood that these methods and systems are not limited to any particular radiation therapy delivery system or application described herein, and may be advantageous when used in various other radiation therapies and delivery systems, including conventional radiation therapies as well as non-medical applications.

A fundamentally different approach to managing motion is to deliver the treatment so rapidly that no significant physiologic motion occurs between verification imaging and completion of treatment. According to certain embodiments of the invention, an accelerator, more preferably a compact high-gradient, very high energy electron (VHEE) linear accelerator, which may be a standing wave linear accelerator, together with a delivery system capable of treating patients from multiple beam directions, potentially using all-electromagnetic or radiofrequency deflection steering is provided, that can deliver an entire dose or fraction of high-dose (e.g., 20-30 Gy) radiation therapy sufficiently fast to freeze physiologic motion, yet with a better degree of dose conformity or sculpting than conventional photon therapy. The term "sufficiently fast to freeze physiologic motion" in this document means preferably faster than one human breath hold, more preferably less than 10 seconds, even more preferably less than 5 seconds, even more preferably less than one heartbeat and most preferably less than a second. In addition to the unique physical advantages of extremely rapid radiation delivery, there may also be radio-biological advantages in terms of greater tumor control efficacy for the same physical radiation dose. Certain embodiments of the invention can also treat non-tumor targets, such as, by way of nonlimiting example, ablation or other treatment of: (1) nerves or facet joints for pain control; (2) foci in the brain for neuromodulation of neurologic conditions including pain, severe depression, and seizures; (3) portions of the lung with severe emphysema; and/or (4) abnormal conductive pathways in the heart to control refractory arrhythmias.

According to certain embodiments of the invention, there is provided a system for delivering very high electron energy beam to a target in a patient, comprising: an accelerator capable of generating a very high electron energy beam; a beam steering device capable of receiving the beam from the accelerator and steering the beam to the target from multiple directions; and a controller capable of controlling length of time that the beam irradiates the target, the length of time sufficiently fast to freeze physiologic motion, and to control the directions in which the beam steering device steers the beam to the target.

In certain embodiments, the controller is configured to receive information from an imaging device and use the information from the imaging device to control the directions in which the beam steering device steers the beam to the target. In some embodiments, the accelerator is a linear electron accelerator capable of generating a beam having energy of between 1 and 250 MeV, more preferably 50 and 250 MeV and most preferably between 75 and 100 MeV. In a rapid radiation treatment embodiment, the time period is preferably faster than one human breath hold, more preferably less than 10 seconds, even more preferably less than 5 seconds, even more preferably less than one heartbeat and most preferably less than a second. The beam steering device may include an electro-magnetic device and/or a radiofrequency deflector device. In some embodiments, the beam steering device includes a gantry, the gantry including multiple beam ports. The beam ports may be disposed in various arrangements, including arrangements that are annular, staggered, and planar, non-planar. In some embodiments, the beam steering device includes a continuous annular gantry. In certain embodiments, the beam steering device is capable of providing thin pencil beam raster scanning.

Methods of utilizing beams of spatially varying beam intensity and the collimation assembly features described above to provide a radiation treatment, particularly a rapid radiation treatment, are also provided herein.

BRIEF DESCRIPTION OF THE DRAWINGS

FIG. 18C shows a conceptual schematic channel configuration in which channels of various sizes are interspersed to provide for example larger area coverage with larger channels and finer field edge shaping with smaller channels.

DETAILED DESCRIPTION OF THE INVENTION

I. Rapid Radiation Treatment

A. Significance

Figure 1:
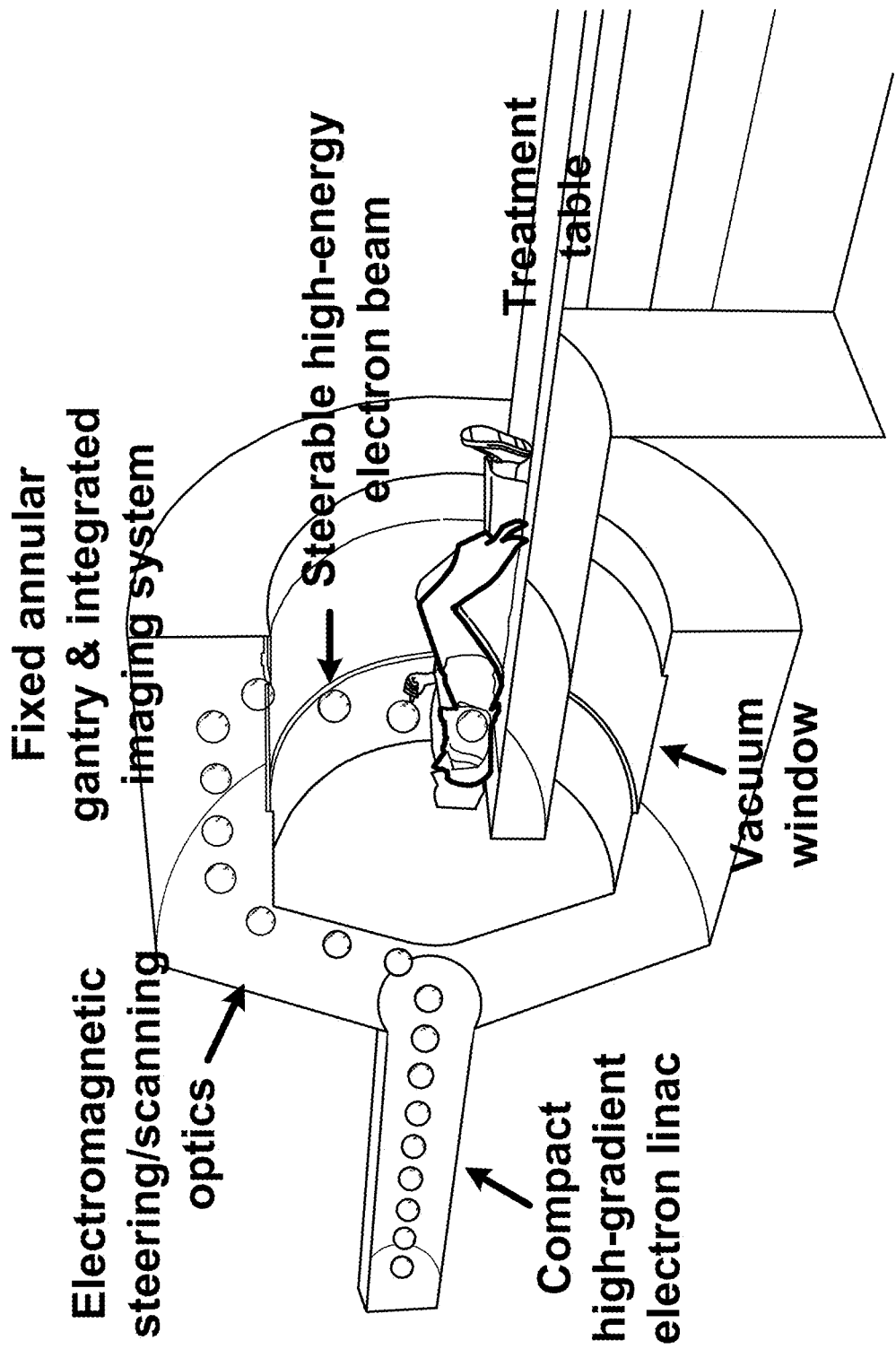
FIG. 1 is a schematic representation of a system in accordance with certain embodiments of the invention, showing beam access from a large number of axial directions by electromagnetic- or radiofrequency deflection steering.

In the U.S., cancer has surpassed heart disease as the leading cause of death in adults under age 85, and of the 1.5 million patients diagnosed with cancer each year, about two thirds will benefit from radiation therapy (RT) at some point in their treatment, with nearly three quarters of those receiving RT with curative intent. Worldwide, the global burden of cancer is increasing dramatically owing to the aging demographic, with an incidence of nearly 13 million per year and a projected 60% increase over the next 20 years, and the number of patients who could benefit from RT far exceeds its availability. Moreover, even when RT is administered with curative intent, tumor recurrence within the local radiation field is a major component of treatment failure for many common cancers. Thus, improvements in the efficacy of and access to RT have tremendous potential to save innumerable lives.

Although there have been major technological advances in radiation therapy in recent years, a fundamental remaining barrier to precise, accurate, highly conformal radiation therapy is patient, target, and organ motion from many sources including musculoskeletal, breathing, cardiac, organ filling, peristalsis, etc. that occurs during treatment delivery. Conventional radiation delivery times are long relative to the time scale for physiologic motion, and in fact, more sophisticated techniques tend to prolong the delivery time, currently 15-90 minutes per fraction for state-of-the-art high-dose radiotherapy. The very fastest available photon technique (arc delivery with flattening filter free mode) requires a minimum of 2-5 min to deliver 25 Gy. Significant motion can occur during these times.

Even for organs unaffected by respiratory motion, e.g., the prostate, the magnitude of intrafraction motion increases significantly with treatment duration, with 10% and 30% of treatments having prostate displacements of >5 mm and >3 mm, respectively, by only 10 minutes elapsed time. As such, considerable effort has been devoted to developing "motion management" strategies in order to suppress, control, or compensate for motion. These include complex immobilization, fiducial marker implantation, respiratory gating, and dynamic tumor tracking, and in all cases still require expansion of the target volume to avoid missing or undertreating the tumor owing to residual motion, at the cost of increased normal tissue irradiation.

Several factors contribute to long delivery times in existing photon therapy systems. First, production of x-rays by Bremsstrahlung is inefficient, with less than 1% of the energy of the original electron beam being converted to useful radiation. Second, collimation, and particularly intensity modulation by collimation, is similarly inefficient as the large majority of the beam energy is blocked by collimation. Third, using multiple beam angles or arcs to achieve conformal dose distributions requires mechanical gantry motion, which is slow. Treatment using protons or other heavier ions has dosimetric advantages over photon therapy, and these particles can be electromagnetically scanned very rapidly across a given treatment field. However changing beam directions still requires mechanical rotation of the massive gantry, which is much larger and slower than for photon systems. The cost and size of these systems also greatly limits their accessibility.

Very high-energy electrons (VHEE) in the energy range of 50-250 MeV have shown favorable dose deposition properties intermediate between megavoltage (MV) photons and high-energy protons. Without the need for inefficient Bremsstrahlung conversion or physical collimation, and with a smaller steering radius than heavier charged particles, treatment can be multiple orders of magnitude faster than any existing technology in a form factor comparable to conventional medical linacs. According to certain embodiments of the invention, a compact high-gradient VHEE accelerator and delivery system is provided that is capable of treating patients from multiple beam directions with great speed, using electro-magnetic, radiofrequency deflection or other beam steering devices. Such embodiments may deliver an entire dose or fraction of high-dose radiation therapy sufficiently fast to freeze physiologic motion, yet with a better degree of dose conformity or sculpting, and decreased integral dose and consequently decreased risk of late toxicities and secondary malignancies, than the best MV photon therapy. Suitable energy ranges in accordance with certain embodiments of the invention are 1-250 MeV, more preferably 50-250 MeV, and most preferably 75-100 MeV. Again, as described in the Summary section above, the term "sufficiently fast to freeze physiologic motion" in this document means preferably faster than one human breath hold, more preferably less than 10 seconds, even more preferably less than 5 seconds, even more preferably less than one heartbeat and most preferably less than a second.

According to some embodiments, a major technological advance is extremely rapid or near instantaneous delivery of high dose radiotherapy that can eliminate the impact of target motion during RT, affording improved accuracy and dose conformity and potentially radiobiological effectiveness that will lead to improved clinical outcomes. Rapid imaging and treatment can also lead to greater clinical efficiency and patient throughput. For standard treatments, the room occupancy time can be reduced to less than 5 minutes. There can also be a great practical advantage for special populations like pediatric patients who normally require general anesthesia for adequate immobilization during long treatments, and who can instead be treated with only moderate sedation for such rapid treatments. Such advantages can be achieved, according to some embodiments, in a compact physical form factor and low cost comparable to conventional photon therapy systems, and much lower than hadron therapy systems. One embodiment is shown in FIG. 1, which shows a system wherein beam access from a large number of axial directions is achieved by electromagnetic steering without moving parts or with a minimum of moving parts, for extremely fast highly conformal radiotherapy. The system shown in FIG. 1 includes a compact linear accelerator, a beam steering device, and a controller for controlling the very high electron energy beam that is delivered to the patient. The embodiment can also include an integrated imaging device that obtains images of portions of the patient including the tumor or other site to be treated. The imaging device can also provide information to allow for control of the beam steering device in order to control directions from which the beam is delivered, and timing of the beam, among other variables.

Furthermore, the prolonged treatment times of conventional highly conformal RT are sufficiently long for repair of sublethal chromosomal damage to occur during treatment, potentially reducing the tumoricidal effect of the radiation dose. Thus in addition to the unique physical advantages of extremely rapid radiation delivery, there may also be dose advantages. It is hypothesized that the treatment times sufficiently fast to freeze physiologic motion that are made possible by certain embodiments of the invention may be more biologically effective, producing enhanced tumor cell killing for the same physical dose. Differences between certain embodiments of the invention and conventional photon therapy that impact biological effectiveness include a much faster delivery time and differences in the radiation quality.

Dose rate effects are well described in the radiobiology literature, in which prolongation of delivery times results in decreased cell killing. The main mechanism known to be responsible for this effect is repair of potentially lethal DNA double strand breaks (DSB) during the interval over which a given dose of radiation is delivered. Several in vitro studies have demonstrated significantly decreased cell killing when delivery is protracted from a few minutes to tens of minutes. However, there is a lack of consensus in the literature regarding the kinetics of sublethal damage (SLD) repair, with some studies suggesting that components of SLD repair may have repair half-times of as little as a few minutes. If so, shortening the delivery times even from a few minutes to a time period sufficiently fast to freeze physiologic motion has the potential to increase tumor cell killing.

B. Beam Steering

Some embodiments of the invention take advantage of the fact that electrons are relatively easier to manipulate using electric and magnetic fields. Charged particles such as electrons and protons can be produced as spatially coherent beams that can be steered electromagnetically or with radiofrequency deflection with high rapidity. Thus, direct treatment with scanned charged particle beams can eliminate the inefficiencies of Bremsstrahlung photon multiple beams from different directions toward the target in the patient. All conventional radiation therapy systems accomplish multidirectional treatment by mechanically rotating a gantry, or an entire compact linac, or even cyclotron, directing radiation to the target from one direction at a time.

As a preliminary matter, at the end of the accelerator structure the beam must be deflected and then transported to the exit port and toward a target in or on the patient, such as a tumor in the patient. At the exit port the beam must be steered again to change the exit angle and/or beam size to adapt to the treatment plan. Electro-magnetic and/or RF deflector steering systems will manipulate the electron beam.

A variety of gantry designs are potentially available, from simple to complex, ranging from multiple discrete beam ports arranged around the patient to a continuous annular gantry to allow arbitrary incident axial beam angles. The design depends on a number of factors, including scanning strategies such as thin pencil beam raster scanning vs. volume filling with non-isocentric variable-size shots, or use of transverse modulation of the electron beam profile.

According to one embodiment, the steering system of the electron beam starts at the end of the accelerator structure with a two-dimensional deflector, which guides the beam into one of multiple channels. Once the beam enters a specific channel it is guided all the way to the exit of the channel, which is perpendicular to the axis of the patient. The guidance through the channels is achieved using low aberration electron optics. At the exit of each channel another small 2-D deflector can be added to scan the beam over a target. The number of channels can then be about 10-50. For a given channel width, a larger initial deflection would increase the number of channel entry ports that fit into the circumference swept by the beam. Thus if the field strength were increased, the number of channels could be increased to 100 or more.

Because a linear accelerator will typically consume 50 to 100 MW of peak power to achieve 100 MeV of acceleration, over a length of 2 to 1 m respectively, potentially megawatt powered RF deflectors can be considered. These have the advantage of being ultra-fast and permit capitalization on the RF infrastructure that is used for the main accelerator structure. In any event, the delivery system is preferably optimized to achieve high-dose treatment times sufficiently fast to freeze physiologic motion.

Beam steering systems according to certain embodiments of the invention adopt a design that uses a smaller number of discrete beam channels, for example 3-10, that are mechanically rotated with the gantry around the patient. The initial deflector at the exit of the accelerator rapidly steers beams into the channels as they rotate. Although the ideal is to eliminate the need for any mechanical moving parts, some advantages of this design include: arbitrary rotational angular resolution despite a fixed number of beam channels; reduced complexity and possibly cost given the smaller number of beam channels needed to achieve equivalent angular coverage; and the larger space between beam channels which makes it more straightforward to incorporate an x-ray source and detecting array for imaging, which when rotated provides integrated computed tomography imaging. The rate of mechanical rotation preferably provides full angular coverage sufficiently fast to freeze physiologic motion. The greater the number of beam channels, the less rotational speed required to meet this condition as a general matter.

One innovation of certain embodiments of the invention is to eliminate mechanical gantry rotation, thus a beam steering system with no mechanical moving parts. One such embodiment is illustrated in FIG. 1, in which there is a gantry through which a charged particle beam is electromagnetically steered or steered using radiofrequency deflection to the target from any axial direction and a limited range of non-coplanar directions in addition. An alternative implementation is to use multiple discrete beam ports arranged radially around the patient, with the beam being steered through each of the ports to the target for multidirectional beam arrangements. Another alternative implementation is to have multiple accelerating structures, one for each of a set of beam ports arranged radially around the patient.

Such novel treatment system geometries and steering systems can greatly enhance the treatment delivery speed of radiation therapy using any type of charged particle. Combining it with high-energy electrons in the 1-250 MeV range, more preferably the 50-250 MeV range, most preferably the 75-100 MeV range, has the following additional advantages: (1) Conformal dose distributions to both superficial and deep targets in patients superior to what can be achieved with conventional high-energy photon therapy; (2) Compactness of the source and power supply, which by using high-gradient accelerator designs such as those based wholly or partially on accelerators developed or in development at the SLAC National Accelerator Laboratory (SLAC) as described further below can accelerate electrons up to these energies in less than 2 meters; (3) Compactness of the gantry/beam ports compared to protons or ions because of the smaller electro-magnetic fields needed for electrons. This results in a system of comparable cost and physical size to existing conventional photon radiotherapy treatment systems, yet with better dose distributions and far faster dose delivery.

If treatment with photon beams is still desired, an alternative embodiment is to incorporate in this geometry an array of high density targets and collimator grid in place of a single target/multi-leaf collimator combination, one per beam port in the case of discrete beam ports, or mounted on a rapidly rotating closed ring and targeted by the scanned electron beam in the case of an annular beam port, in order to produce rapidly scanned, multidirectional photon beams. While this approach may be subject to the inefficiency of Bremsstrahlung conversion, the speed limitations of conventional mechanical gantry and multi-leaf collimator motions may be essentially eliminated. The main potential advantage of this implementation is that existing commercial electron linacs in a lower energy range could be used as the source.

In addition to extremely rapid dose delivery, certain embodiments of the invention naturally facilitate rapid image-guidance to ensure accuracy. By adjusting the energy of the scanned electron beam and directing it to an annular target or a fixed array of targets, with an appropriately arranged detector array, extremely fast x-ray computed tomography (CT) or digital tomosynthesis images can be obtained and compared to pre-treatment planning images immediately before delivery of the dose. Alternative embodiments can include integration of more conventional x-ray imaging or other imaging modalities, positron emission tomography and other options described further below.

C. Monte Carlo Simulation Design Considerations

One approach in designing certain embodiments of the invention is to proceed using some or all of the following: (1) Monte Carlo simulations to determine optimal operating parameters; (2) experimental measurements of VHEE beams to validate and calibrate the Monte Carlo codes; (3) implementation factors for practical, cost-efficient and compact designs for the systems; and (4) experimental characterization of key radiobiological aspects and effects.

1. Monte Carlo (MC) Simulation

MC simulations of VHEE of various energies have been performed on a sample case to estimate the range of electron energies needed to produce a plan comparable to optimized photon therapy. Dose distributions were calculated for a simulated lung tumor calculated on the CT data set of an anthropomorphic phantom.

Specifically, an optimized 6 MV photon beam Volumetric Modulated Arc Therapy Stereotactic Ablative Body Radiotherapy (VMAT SABR) plan calculated in the Eclipse treatment planning system, and simplistic conformal electron arc plans with 360 beams using a commonly available 20 MeV energy and a very high 100 MeV energy calculated with the EGSnrc MC code were compared. (See Walters B, Kawrakow I, and Rogers D W O, DOSXYZnrc, Users Manual, 2011, Ionizing Radiation Standards National Research Council of Canada. p. 1-109, available online at (http://irs.inms.nrc.ca/software/beamnrc/documentation/pirs794/), incorporated herein by this reference).

Figure 2A:
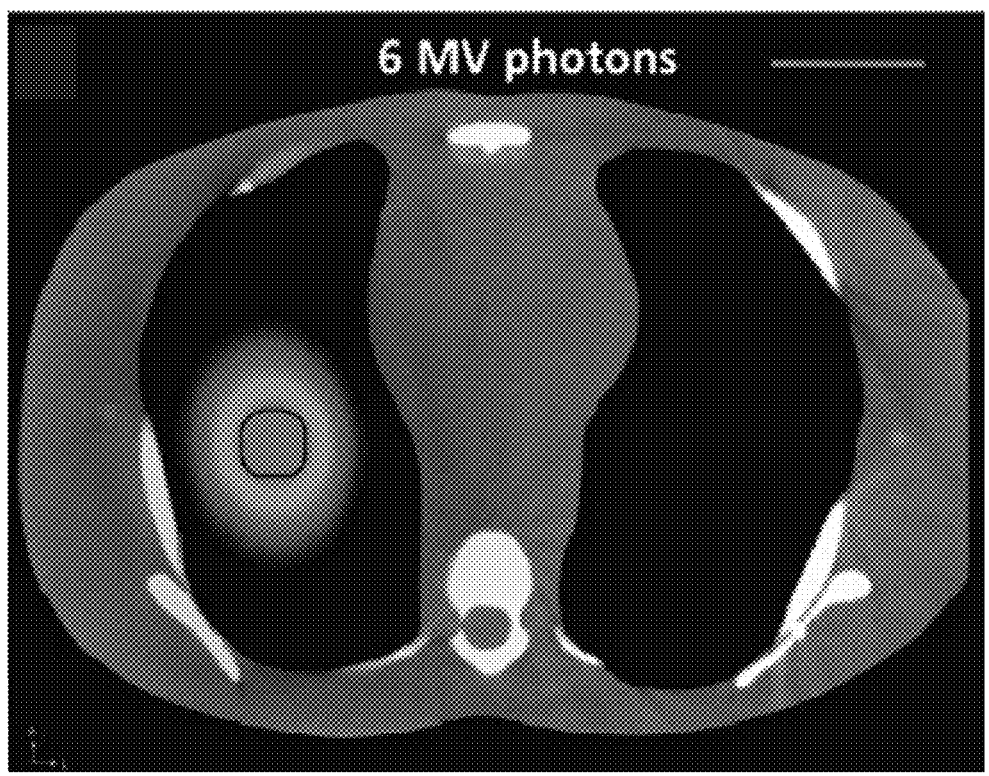
FIGS. 2A-2F show comparative simulation results of SABR for an early stage lung tumor using 6 MV photons, 20 MeV electrons, and 100 MeV electrons.
Figure 2B:
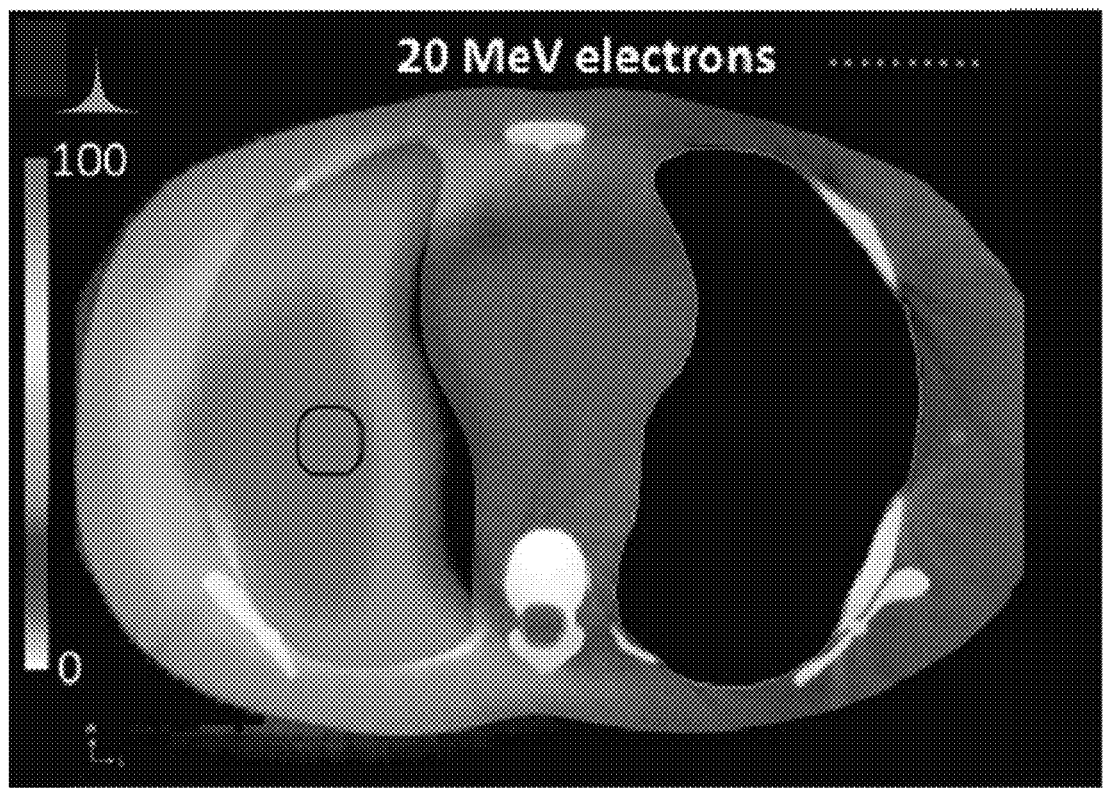
Figure 2C:
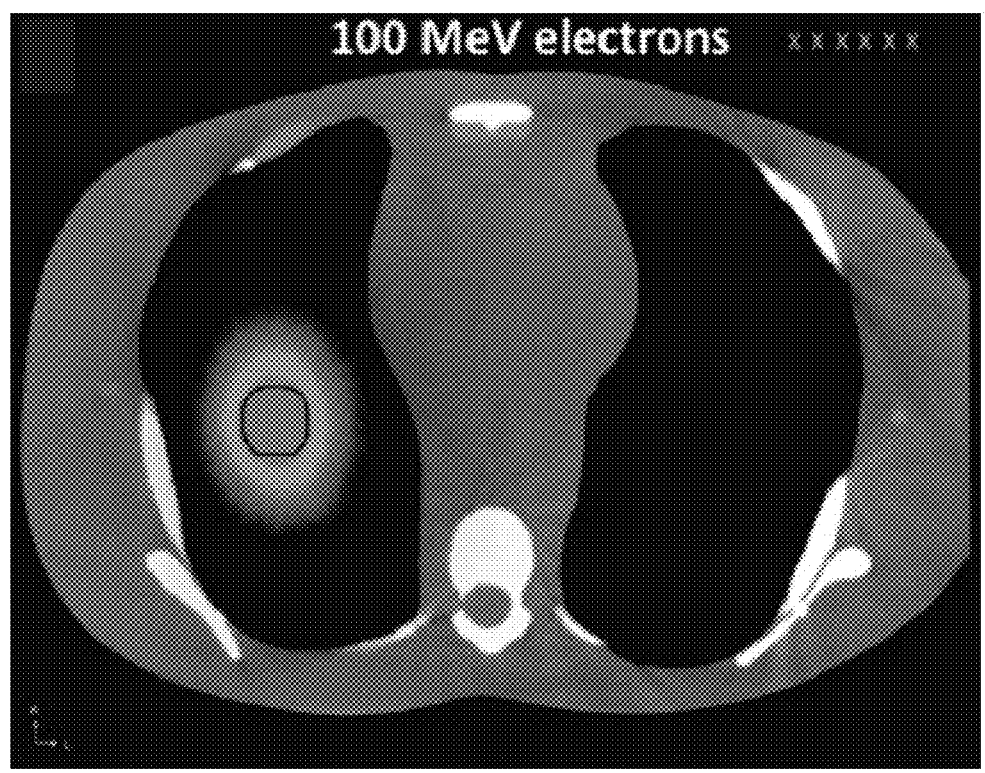
Figure 2D:
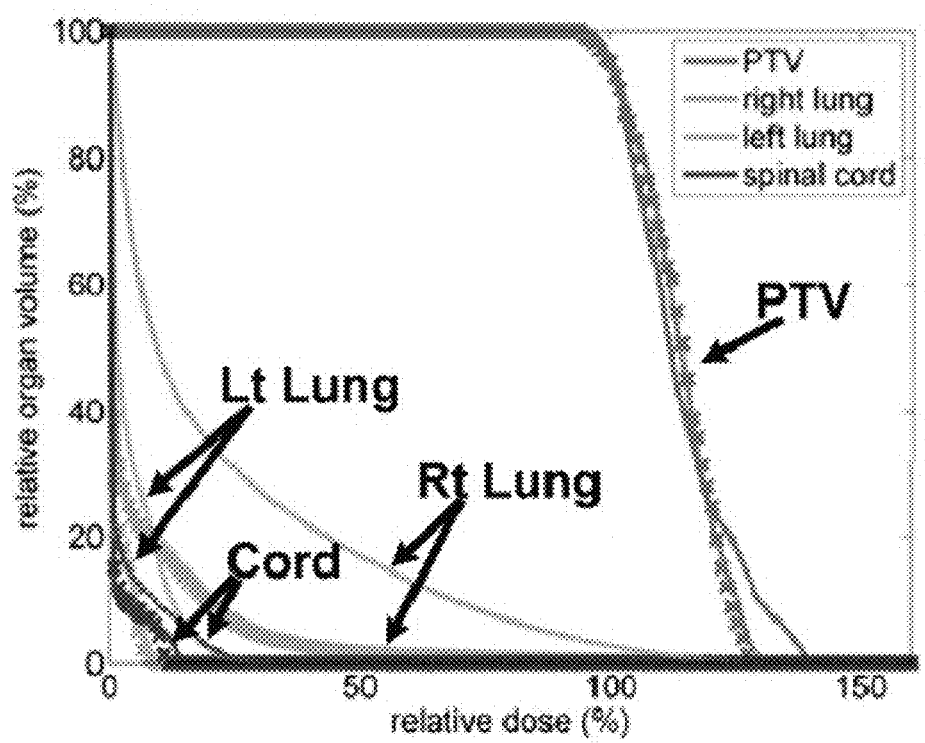

FIG. 2A-F show axial images of simulation of SABR for an early stage lung tumor: dose distribution in an anthropomorphic phantom for a state-of-the-art 6 MV photon VMAT plan (FIG. 2A), a conformal electron arc plan using currently available 20 MeV electron beam (FIG. 2B), and a conformal electron arc plan using a 100 MeV electron beam as might be delivered by an embodiment of the invention (FIG. 2C). A graphical representation shows dose volume histogram ("DVH") of the planning target volume ("PTV") (delineated in black in the axial images) and critical organs: DVHs for 6 MV photons are shown in solid, 20 MeV electrons in dotted, and 100 MeV electrons in crossed lines (FIG. 2D). The plans were normalized to produce the same volumetric coverage of the PTV by the prescription dose. While conventional 20 MeV electrons results in poor conformity, the 100 MeV electron plan, even without optimization, is slightly more conformal than the 6 MV photon VMAT plan. Simulating conformal electron arcs across an energy range of 50-250 MeV (FIG. 2E, 2F) demonstrates that both the high (100%) and intermediate (50%) dose conformity indices (CI100% and CI50%) as well as the mean lung dose and total body integral dose are superior for electron energies of ~80 MeV and higher for this selected clinical scenario. With inverse optimization, superior plans with even lower electron energies should be possible.

Figure 2E:
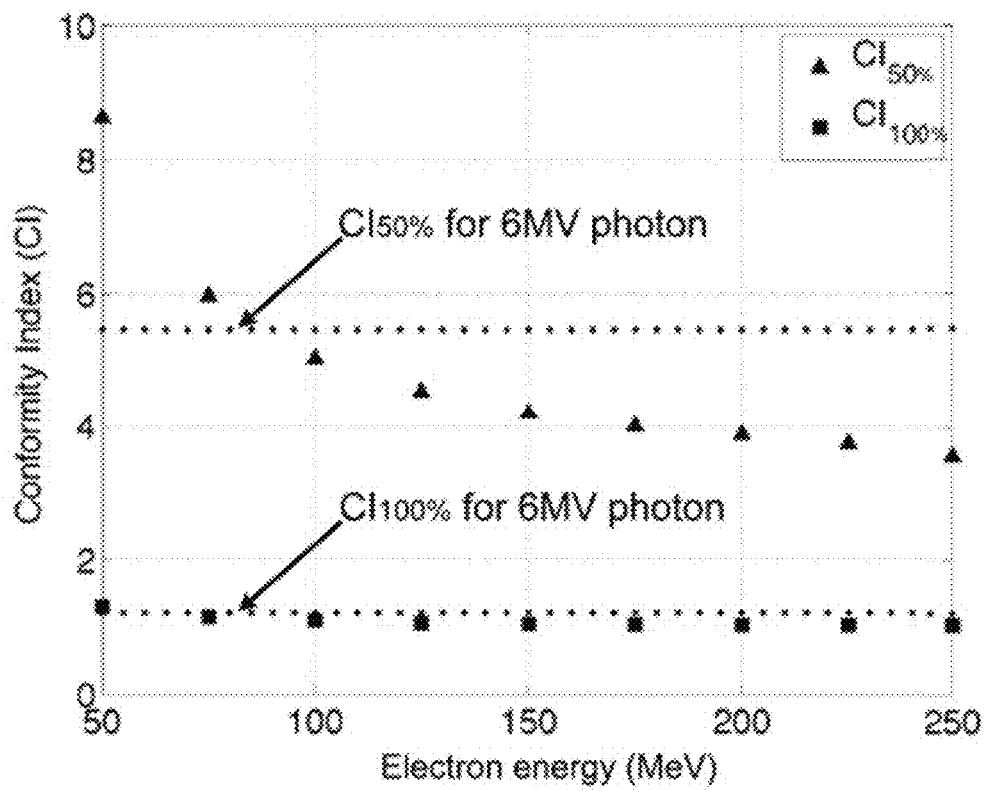
Figure 2F:
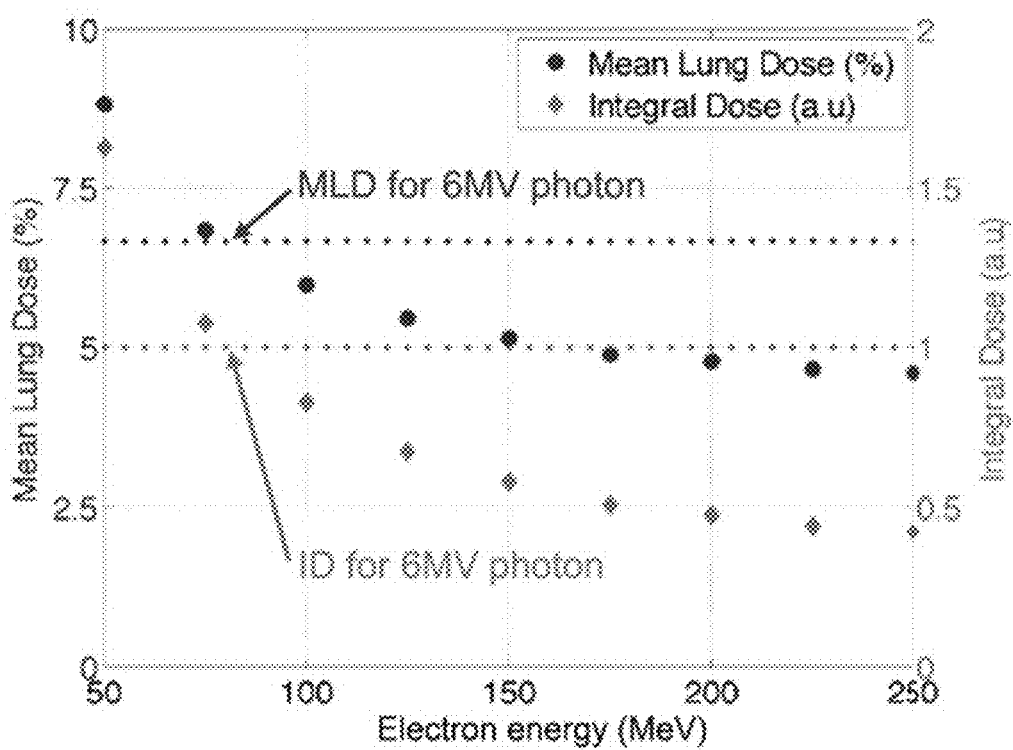

As shown in FIGS. 2A-2F, the axial views of the dose distributions demonstrate that when all the plans are normalized to produce the same volumetric coverage of the target, the dose conformity of the 20 MeV beam is poor whereas the 100 MeV electron beam, even without inverse optimization, generates a dose distribution equivalent to the state-of-the-art 6 MV photon beam VMAT plan. In fact, the DVH's of the target and critical structures for the three beams demonstrate slightly better sparing of critical structures with the 100 MeV electron plan compared to the 6 MV photon plan. As shown in FIGS. 2E and 2F, at electron energies above ~80 MeV, simple conformal electron arc plans (normalized to produce the same volumetric coverage of the target) are superior to the optimized 6 MV photon VMAT plan in terms of conformity, with conformity index defined as the ratio of the given percent isodose volume to the PTV, and the normal organ doses (mean lung dose) and total body integral dose (expressed in arbitrary units normalized to the photon plan). In preliminary simulations of this selected clinical scenario, the inventors have found electron energies of 75-100 MeV to produce plans of comparably high to superior quality compared to the best photon plans, and anticipate that plan optimization will produce superior plans with even lower electron energies. For example, the inventors have used Monte Carlo simulations to demonstrate that an 8 cc lung tumor could be treated with 100 MeV electrons to a dose of 10 Gy in 1.3 seconds.

Further optimization of the electron plan can help to define the minimum electron beam energy with a comparable dose distribution to the best photon VMAT plan. In preliminary simulations of this selected clinical scenario, the inventors have found electron energies of 75-100 MeV to produce plans of comparably high quality to the best photon plans, and anticipate superior plans with plan optimization.

2. Experimental Measurement of VHEE Beams a. Monte Carlo Simulations

Figure 3A:
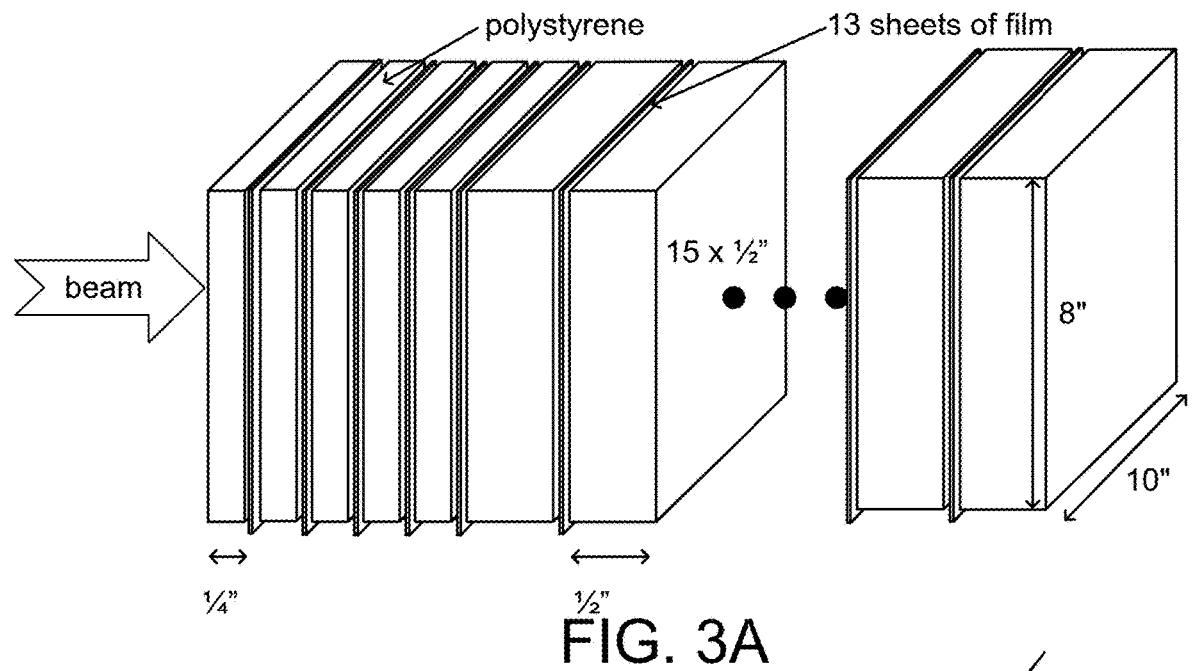
FIGS. 3A-3E show a schematic (FIG. 3A) and photograph (FIG. 3B) of the experimental setup for film measurements (FIG. 3C) of very high energy electron beams at the Next Linear Collider Test Accelerator (NLCTA) beam line at the SLAC National Accelerator Laboratory (SLAC), together with Monte Carlo simulations (solid lines) and film measurements (markers) of percentage depth dose curves (FIG. 3D) and beam profiles taken at 6 mm depth (FIG. 3E) for 50 MeV and 70 MeV beams, respectively.
Figure 3B:
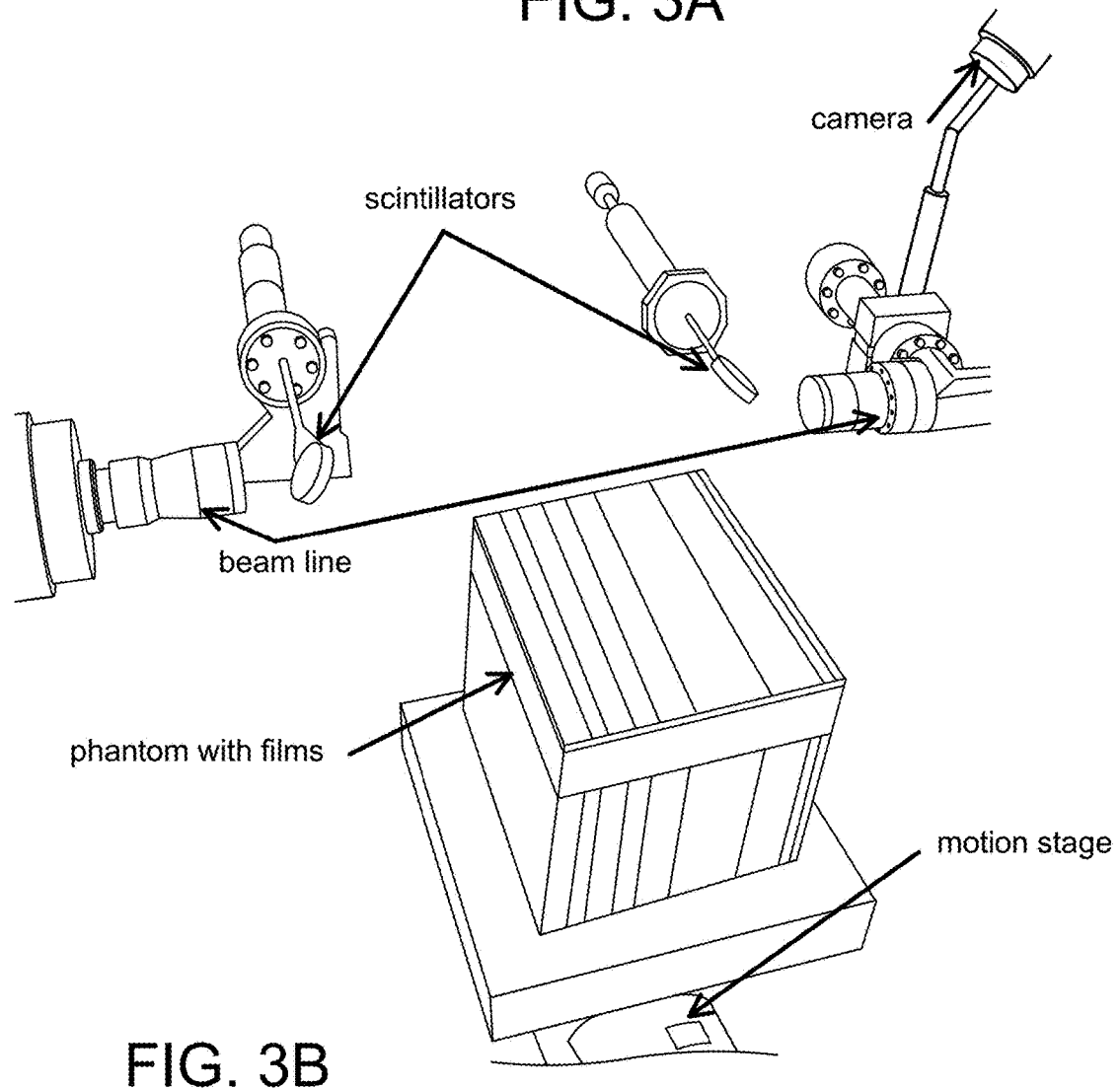
Figure 3C:
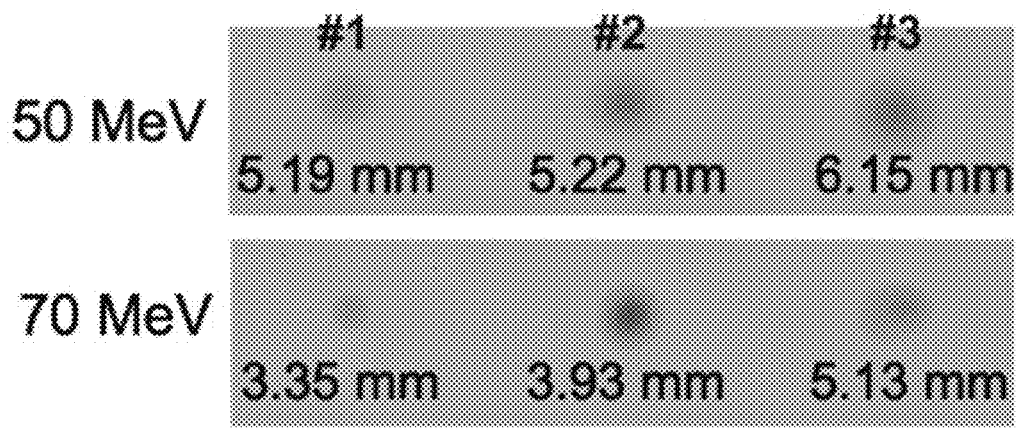

To demonstrate the accuracy of Monte Carlo calculations with VHEE beams, the inventors experimentally measured the dose distribution and depth dose profiles at the NLCTA facility at SLAC. Of note, the NLCTA employs compact high-gradient linear accelerator structures which can produce beams that are relevant to those potentially suitable for certain embodiments of the invention. The inventors assembled a dosimetry phantom by sandwiching GAFCHROMIC EBT2 films (International Specialty Products, Wayne, N.J.) between slabs of tissue equivalent polystyrene as shown in FIGS. 3A-3E. FIG. 3A is a schematic and FIG. 3B is a photograph of the experimental setup for film measurements (FIG. 3C) of very high-energy electron beams at the NLCTA beam line at SLAC. Monte Carlo simulations and film measurements of percentage depth dose curves (FIG. 3D) and 2-D dose distributions taken at 6 mm depth (FIG. 3E) for 50 MeV and 70 MeV beams demonstrate a high degree of agreement between calculation and measurement.

By way of procedure and in greater detail, the phantom as shown in FIG. 3A was irradiated with 50 MeV and 70 MeV beams. Three beam sizes ranging from 3.35 to 6.15 mm were tested for each energy level. The energy was measured by a spectrometer upstream from the location of the experiment and the beam size was measured by two scintillating screens using two cameras just before and after the phantom with the phantom removed from the beam line (FIG. 3B). The films were calibrated with a clinical electron beam at 12 MeV. MC simulations have demonstrated no energy dependence of the film response at electron energies above 1 MeV. The number of particles required to irradiate the films to dose levels between 1-5 Gy to match the dynamic range of the film was determined for each beam size using MC simulations and used in the experiment. The charge was set to 30 pC/pulse corresponding to $1.9 \times 10^8$ electrons and the pulse rate was reduced to 1 Hz for easier control of the exposure. The number of pulses varied from 2 to 40 pulses depending on the beam size. The experimental and calibration films were read out in a flatbed scanner (Epson Perfection V500, Long Beach, Calif.) with 0.1 mm pixels 24 hours after irradiation (FIG. 3C) and central axis percentage depth dose (PDD) curves and 2-dimensional dose distributions at various depths were plotted. The experimental setup was simulated in MCNPX 5.0 MC code. (See Palowitz D B, MCNPX User's Manual, Version 2.7.0, 2011. available online at (http://mcnpx.lanl.gov/documents.html), incorporated herein by reference).

Figure 3D:
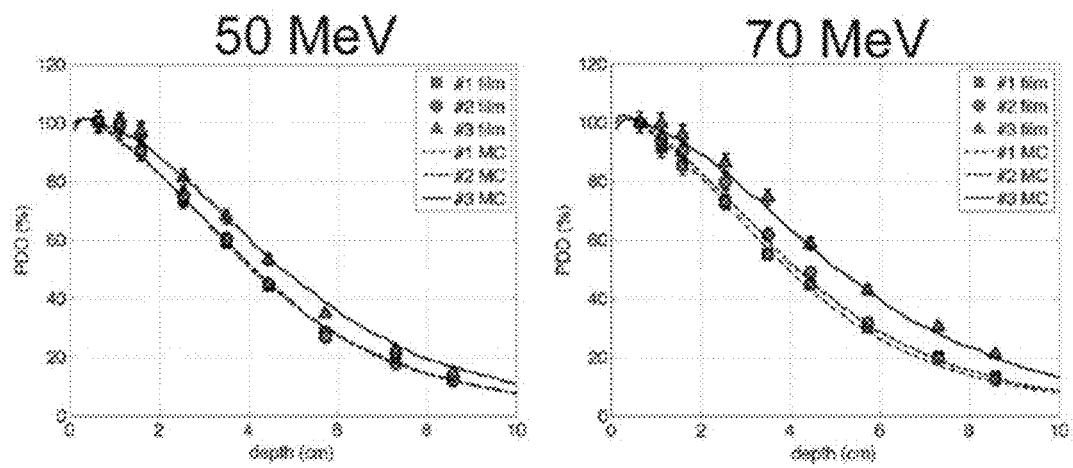
Figure 3E:
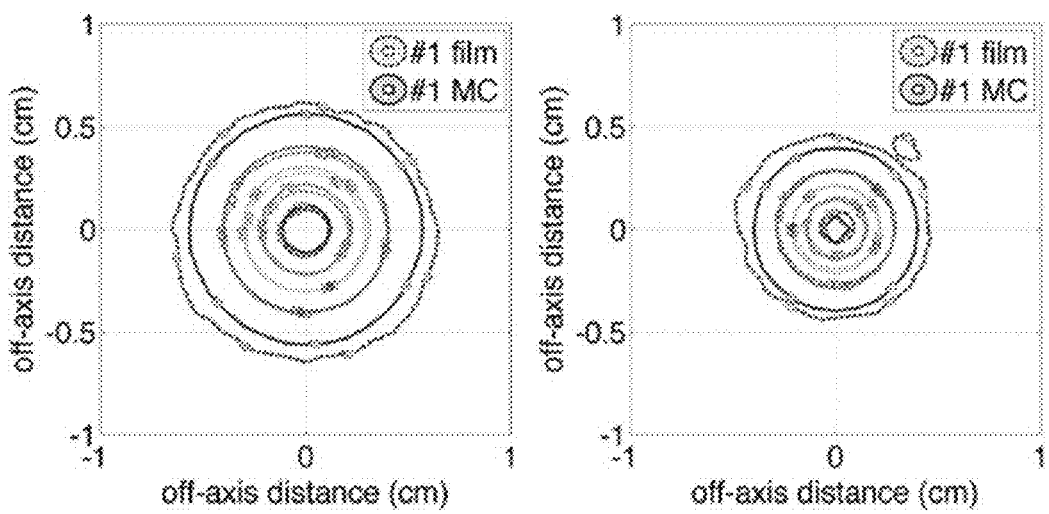

The simulations are compared to measurements in FIG. 3D-3E. Good agreement was observed for both the PDD curves and beam profiles for 50 and 70 MeV. These preliminary results indicate that dose from VHEE beams can be measured with GAFCHROMIC films and that VHEE beams can be accurately simulated with the GEANT4 code.

In the arrangement shown in FIG. 3B, a 50-μm vacuum window made of stainless steel was used to interface the accelerator line with open air, in which the dose phantom (FIG. 2A) was placed. The stainless window was found to cause significant angular beam spreading, so that the simulations were also performed with a beryllium window which imparted less beam spreading. While a vacuum window is necessary to separate the vacuum of the accelerator beam line from the open air and the patient, significant angular spread will adversely affect beam performance and clinical accuracy. The angular spread from a thinner beryllium window was still present but it was much smaller than steel, due to beryllium's low atomic number.

b. Cross Validation of Monte Carlo Codes

Figure 4:
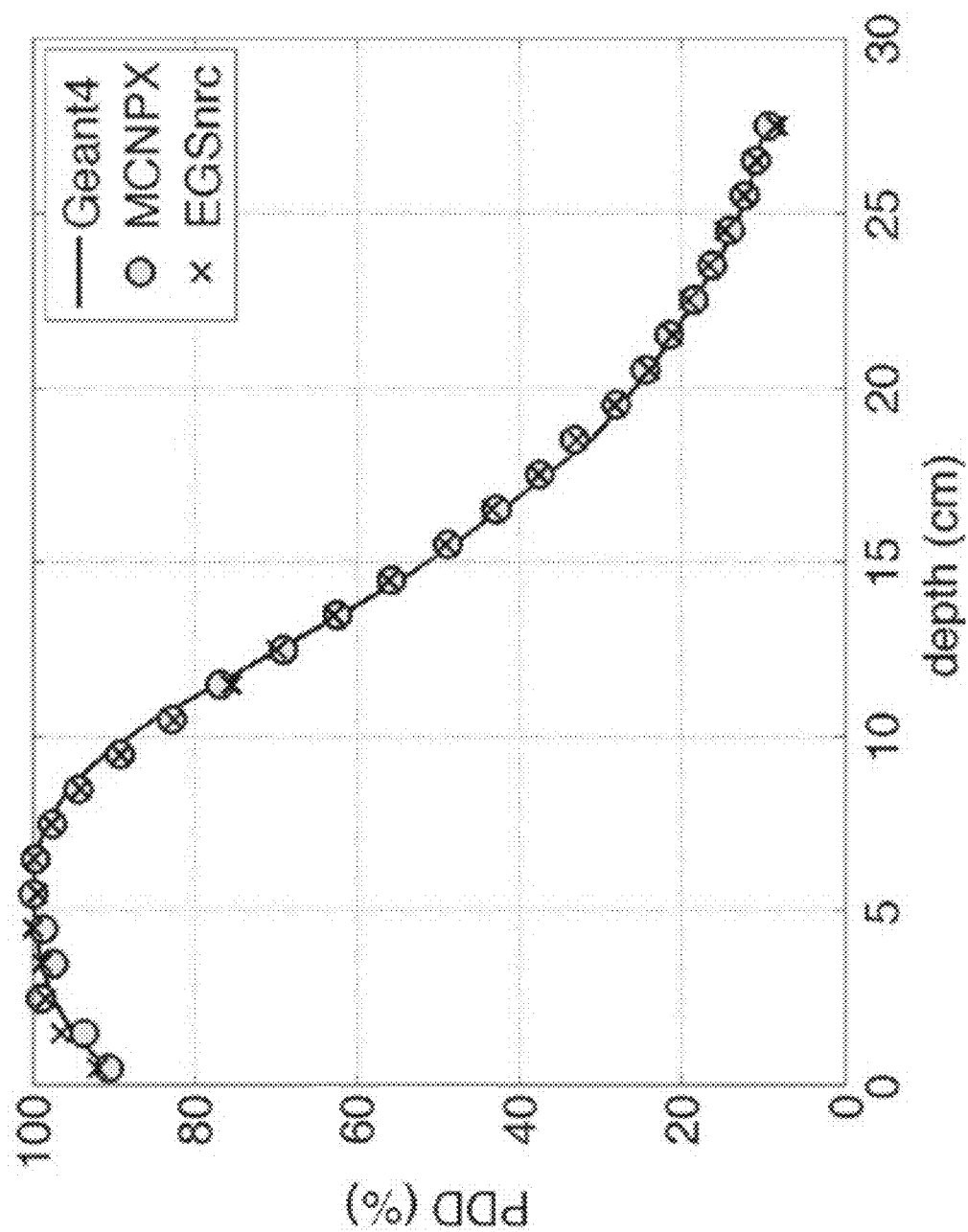
FIG. 4 shows graphic representations of percentage depth doses for a 2×2 cm 100 MeV electron beam in a water phantom, simulated using three independent Monte Carlo codes.
Figure 7:
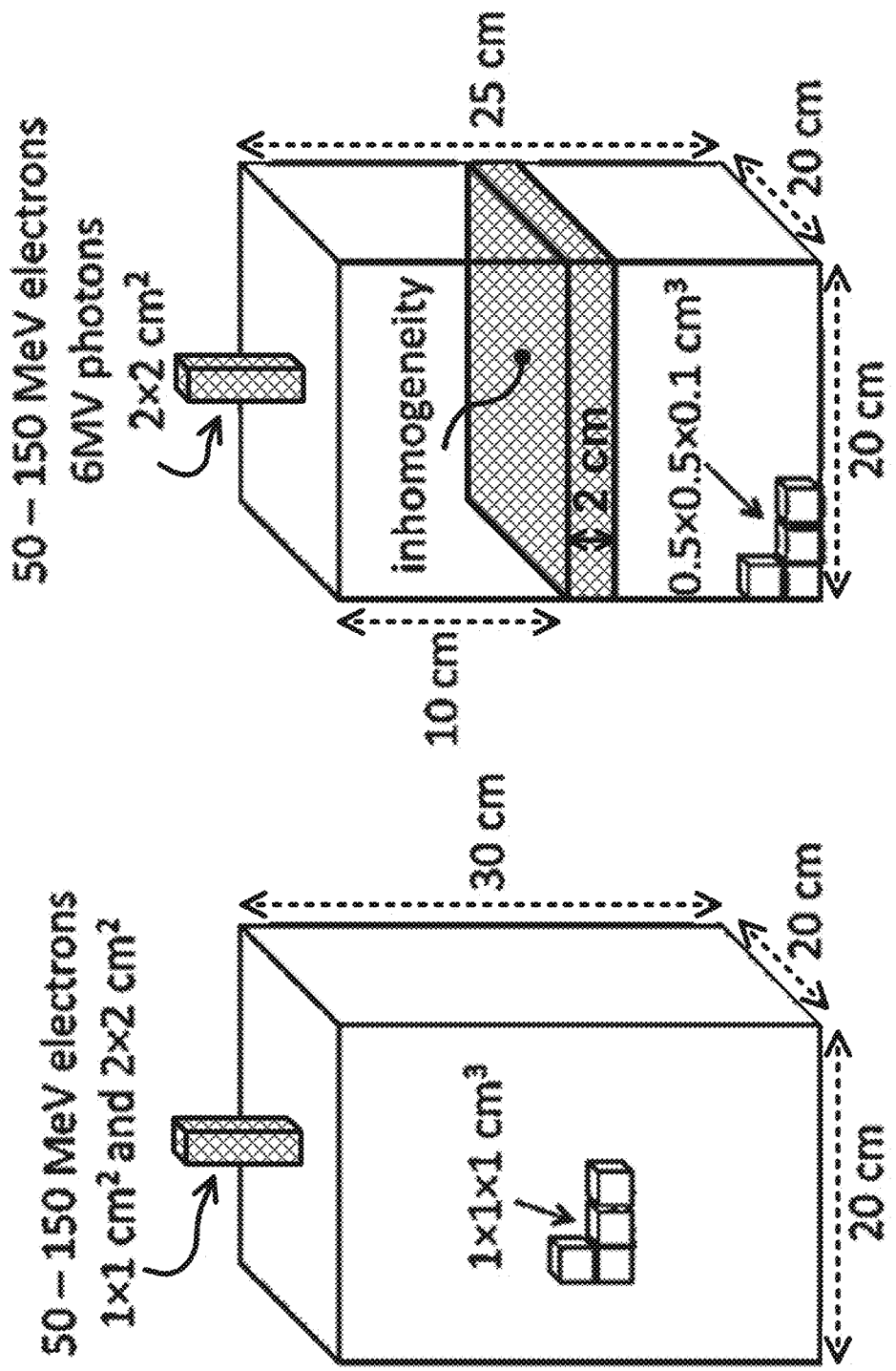
FIG. 7 shows water phantoms used in Monte Carlo simulations conducted in accordance with certain embodiments of the invention.

The inventors performed Monte Carlo simulations using three independent codes for identical geometries to determine the consistency of calculated doses. The dose deposition of a number of rectangular electron beams incident on a 20×20×30 cm water phantom (as shown in FIG. 7) was simulated in the GEANT4, MCNPX, and EGSnrc MC codes. The simulated electron beam energies were 50, 75, 100, and 150 MeV with beam sizes of 1×1 cm and 2×2 cm. The central-axis PDDs were plotted and compared for all three MC codes. Excellent agreement was found between the codes for all of these comparisons, as shown in FIG. 4, which shows PDD for a 2×2 cm 100 MeV electron beam, simulated using the three Monte Carlo codes.

c. VHEE Tissue Interactions

Figure 5:
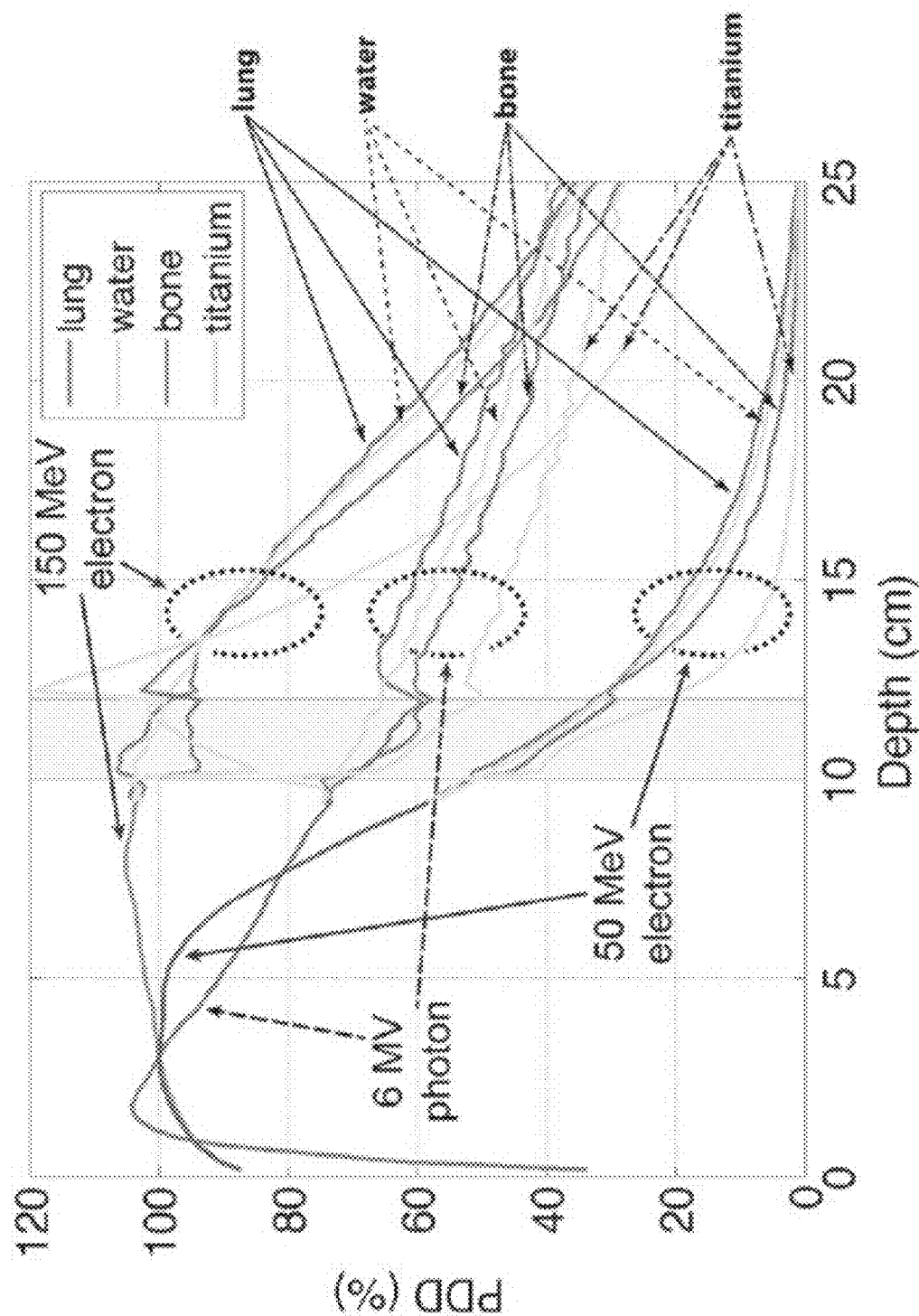
FIG. 5 shows graphic representations of percentage depth doses for 2×2 cm 50 and 150 MeV electron beams compared to 6 MV photons in a water phantom, with 2 cm thick heterogeneous tissue at 10 cm depth.

Monte Carlo simulations were performed to evaluate the impact of various tissue heterogeneities on VHEE beams relative to MV photon beams. FIG. 5 shows PDD curves for 2×2 cm 50 and 150 MeV electron beams compared to 6 MV photons in a water phantom with 2 cm thick heterogeneous tissue at 10 cm depth, normalized to identical dose at 3 cm depth. As shown in FIG. 5, the 50 and 150 MeV VHEE beams are less sensitive to tissue heterogeneity over the density range from lung tissue to titanium prosthetic implants compared to 6 MV photons.

Figure 6:
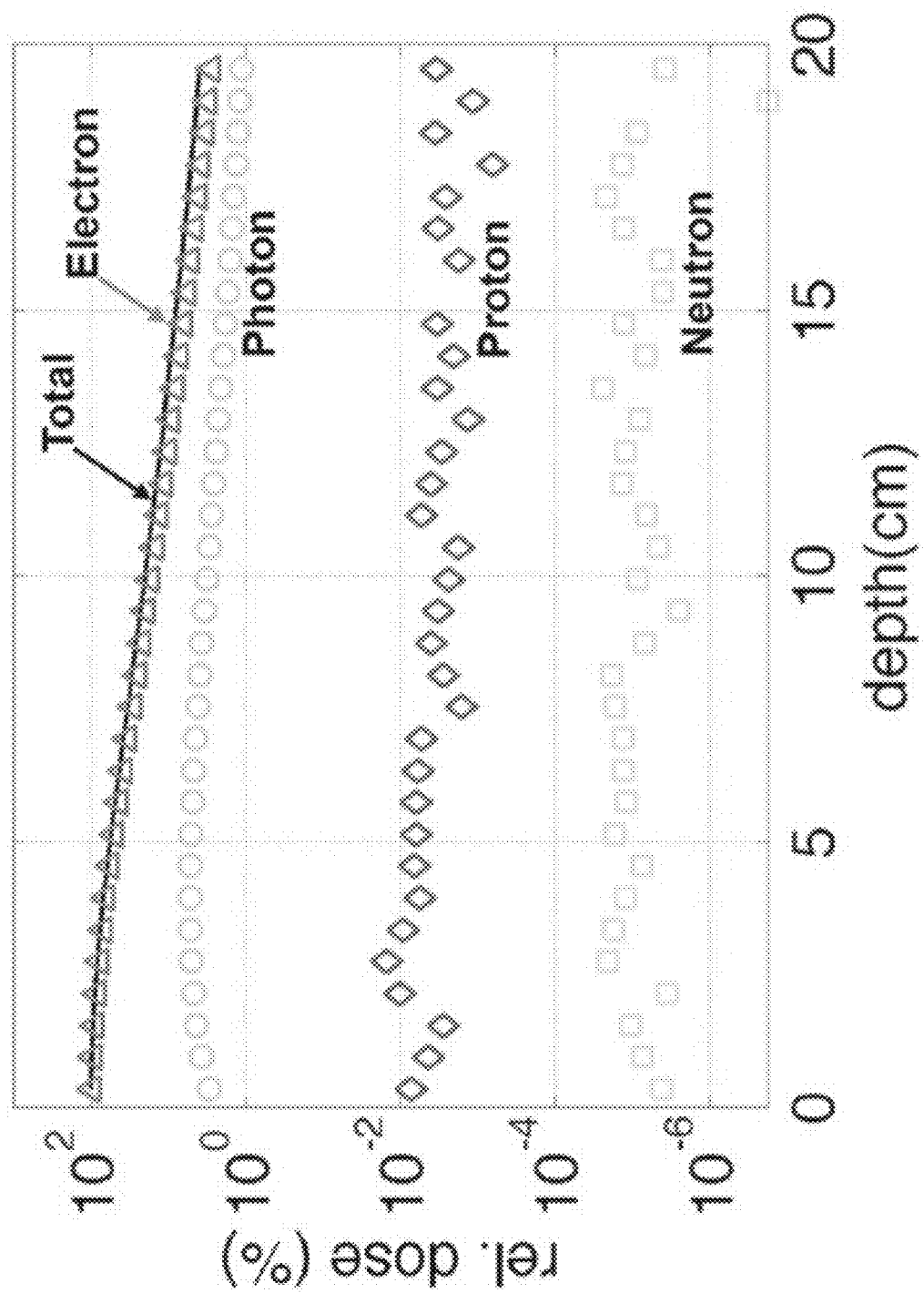
FIG. 6 shows graphic representations of relative contribution to dose from a 100 MeV electron beam vs. secondary generated particles (logarithmic scale).

Contribution of secondary particles produced by Bremsstrahlung and electronuclear interactions to the dose from VHEE beams were also analyzed. FIG. 6 shows relative contribution to dose from a 100 MeV electron beam vs. secondary generated particles (log scale). As shown in FIG. 6, for a 100 MeV electron beam, nearly all the deposited dose is due to electrons, with a minor contribution from Bremsstrahlung x-rays, and far lower dose from protons and neutrons. FIG. 6 also shows that dose from neutrons is far less than with 15-18 MV photons or high-energy protons. This holds for 50 and 70 MeV electrons as well (not shown). For a 25 Gy SABR treatment of a 2 cm diameter target, an upper limit of total body neutron dose is estimated to be 0.6 mSv based on MC simulations. This is in contrast to more than 1-2 orders of magnitude greater estimated neutron doses of 9-170 mSv for scanning beam proton therapy and 15-18 MV photon IMRT for the same clinical scenario, based on published measurements of ambient neutron doses [Schneider U, Agosteo S, Pedroni E, and Besserer J., "*Secondary neutron dose during proton therapy using spot scanning*," International Journal of Radiation Oncology Biology Physics, 2002; 53(1): 244-251. (PMID: 12007965); Howell R M, Ferenci M S, Hertel N E, Fullerton G D, Fox T, and Davis L W, "*Measurements of secondary neutron dose from 15 MV and 18 MV IMRT*," Radiation Protection Dosimetry, 2005; 115(1-4): 508-512. (PMID: 16381776) both of which are incorporated herein by this reference]. An advantage of such potential designs according to certain embodiments compared to >8 MV photon and scanning beam or passive scattering proton therapies is elimination of need for beam modifying structures prior to beam incidence on the patient, in which most neutrons are generated with existing modalities.

d. Tissue Inhomogeneities

The effect of tissue inhomogeneities on dose deposition of VHEE beams has been studied by the inventors. A 20×20×25 cm3 water phantom with 0.5×0.5×0.1 cm3 voxels and a 2-cm thick inhomogeneity placed at 10 cm depth was built (FIG. 7). The 2-cm thick slab was consequently filled with lung with mass density ρ of 0.368 g/cm3, adipose (ρ=0.950 g/cm3), ribs (ρ=1.410 g/cm3), and cortical bone (ρ=1.920 g/cm3) tissue to assess the effect of human tissue inhomogeneities. The tissue composition was obtained from the ICRU-44 document [ICRU. Tissue substitutes in radiation dosimetry and measurement, 1989 (incorporated herein by this reference)]. Moreover, the effect of metals, such as hip prostheses, dental fillings, and surgical clips, was investigated by simulating a steel slab (ρ=8.030 g/cm3). Doses deposited by 50, 100, and 150 MeV electron beams, as well as 6 MV photon beam interacting with the inhomegeneity slab were simulated. The DOSXYZnrc code was chosen for this task due to its simplicity of use and its shortest calculation times. The statistical uncertainties in all central axis voxels were below 1%.

3. Ultra-High Gradient Accelerator Structure Design

Pluridirectional very high electron energy radiation therapy systems and processes according to various embodiments of the invention can be created with various types of electron source. There are a number of potential sources of very high-energy electrons in the range of, for example, up to about 250 MeV. A non-exhaustive list includes cyclotrons, synchrotrons, linacs (which can include more conventional designs with greater length), racetrack microtrons, dielectric wall accelerators, and laser plasma wakefield accelerator sources. Some of these are large and would need to be housed in a separate room. Some are not very mature technologies. In terms of goals of certain embodiments of the invention which can include any or all of compactness (entire system fitting within existing medical linac vaults without a separate room), power requirements, cost, repetition rates, compatibility with intensity modulation techniques described in this document, and other practical considerations, compact very high-gradient standing wave linear accelerators such as those developed at SLAC as described in the two paragraphs immediately below, or derivatives of them, may be at least a logical starting point, although other currently existing or future options should not be ruled out.

Highly efficient π-mode standing wave accelerator structures have been developed at SLAC for the project formerly known as the Next Linear Collider, a positron-electron collider at 500 GeV energy for high-energy physics research [Dolgashev V, Tantawi S, Higashi Y, and Spataro B, "*Geometric dependence of radio-frequency breakdown in normal conducting accelerating structures*," Applied Physics Letters, 2010; 97(17). (http://apl.aip.org/resource/1/applab/v97/i17/p171501_s1) incorporated herein by this reference (hereinafter sometimes "Dolgashev 2010"). Such accelerators are capable of accelerating electrons to 100 MeV within 1 meter (Id.) using an optimized accelerating waveguide powered by a 50 MW 11.4 GHz microwave generator (klystron) [Caryotakis G. Development of X-band klystron technology at SLAC. Proceedings of the 1997 Particle Accelerator Conference, 1997; 3: 2894-2898. (http://ieeexplore.ieee.org/xpls/abs_all.jsp?arnumber=752852) incorporated herein by reference. In order to produce a practical system in terms of cost and size, optimized designs according to certain embodiments of the invention allow both economical production and high performance to minimize the treatment time while allowing maximum possible flexibility in beamlet shapes, directionality, and energy.

Furthermore, it has been shown that coupling a series of small sections of standing-wave accelerators with a distributed radiofrequency (RF) network makes it possible to design a system without any reflection to the RF source [Tantawi S G, "*rf distribution system for a set of standing-wave accelerator structures*," Physical Review Special Topics-Accelerators and Beams, 2006; 9(11) (http://prst-ab.aps.org/abstract/PRSTAB/v9/i11/e112001) incorporated herein by this reference (hereinafter, "Tantawi 2006"). Building on these developments, practical implementations of a standing-wave accelerator structure have been designed to accelerate electrons to 100 MeV within one meter. (See for example, Neilson J, Tantawi S, and Dolgashev V, "Design of RF feed system and cavities for standing-wave accelerator structure," Nuclear Instruments and Methods in Physics Research A: Accelerators, Spectrometers, Detectors and Associated Equipment, 2011; 657(1): 52-54. (hereinafter, "Neilson 2011"), available online at (http://www.sciencedirect.com/science/article/pii/S0168900211008898), incorporated herein by reference). Such accelerators can serve as a basis for or be relevant to certain embodiments of the invention.

D. Other Design Issues

1. Design Options for the Injector System

To inject the required low charge bunch into accelerators according to certain embodiments of the invention, several possibilities are available. Those include a photo-injector RF gun. Additional options can be considered to reduce the cost and size of the system, including a variety of field emitter configurations and RF thermionic guns and DC photocathode guns.

2. Optimization of the RF Source by the Addition of a Pulse Compression System

RF source requirements depend ultimately, at least in part, on the accelerator design. With the optimized cavities as described above, it is projected that a 50 MW source at X-band will be sufficient for a 2 meter accelerator operating at 50 MV/m. This type of source is available at SLAC and is being commercialized by Communications & Power Industries (Palo Alto, Calif.). With the use of a pulse compression system it may be possible to either reduce the cost and sophistication of the RF source dramatically or make the accelerator structure more compact by reducing the length to 1 meter. Because the typical filling time of such a structure is about 100 ns and the RF source typically provides several µs long pulses, one can use a compact RF pulse compressor with a high compression ratio and a power gain of about 3.5 to reduce the required RF source power to only about 14 MW, which opens the door for a variety of sources, including sources that are commercially available now, and including those that include a pulse compression system.

3. Imaging and Target Position Verification Options

Given that treatment according to certain embodiments of the invention is delivered sufficiently fast to freeze physiologic motion, it is important to verify that the target is in the planned position at the time the treatment is triggered or administered. Several dynamic or "real-time" imaging or other localization technologies can be integrated into certain embodiments of the invention for this purpose. Potential such implementations can include any of the following, alone or in combination: integration of two or more x-ray fluoroscopic imaging devices; dynamic optical surface scanning; integration of fast x-ray computed tomography; implantable radiofrequency beacons, whose 3-dimensional position can be read out in real time by an external antenna array. Beacons can be implanted in or near the target and serve as surrogates for the target position; MRI imaging and any of the approaches described in PCT Application No. PCT/US2014/055270 filed Sep. 11, 2014.

4. Implementation of Intensity Modulation

According to certain embodiments of the invention, which may be used with various types of accelerators in accordance with the invention, and in order to achieve highly conformal volumetric dose shaping, radiation fields from each of multiple beam directions can cover an area with varying beam intensity across the field, with the intensity patterns optimized to produce the desired 3-dimensional dose distribution when summed across all beam directions. Such intensity modulation may be produced by raster scanning individual beamlets of varying intensity across the field from each beam direction. Alternatively, it may be produced by using a 2-dimensional intensity-modulated electron pattern at the source, effectively a simultaneously generated array of beamlets of varying intensity, and accelerate and steer the entire array to the target volume. This eliminates the need for a raster scanning mechanism at the exit of each of the beam channels, greatly simplifying the design and reducing the bulk and cost of those components, and increases the treatment delivery speed by delivering beamlets in parallel within a much smaller number of electron pulses or bunches.

II. Technologies to Facilitate Radiation Delivery in Rapid Radiation Treatments

A. Photo Cathode/Photo Electron-Gun

In accordance with certain aspects, methods and systems for rapid generation and delivery of transversely patterned electron beam to targeted tissue for rapid radiation treatment utilize a photo-electron gun. A photo-electron gun is one of various possible techniques that may be used for precise and ultrafast dose delivery using a medical electron accelerator in accordance with the present invention. The dose is produced in rapid pulses of electrons delivered to the targeted tissue from different directions, different transverse beam pattern in each direction. Each pulse has a pre-programmed transverse dose pattern such that the total 3D dose conforms to the target volume in the patient. Projecting a pre-programmed light pattern on a photocathode generates replica of this light pattern with similar transverse distribution of the electrons. This pattern or image is then accelerated through low aberration electron optics toward the targeted tissue.

In an exemplary embodiment, the system operates as follows: a light source, e.g laser, lamp, diode generates short, transversely uniform light pulses. This light pulse is transversely modulated to produce pre-programmed pattern using computer-controlled light-modulator. This patterned light pulse impacts photo-cathodes of the electron gun, creating electron-bunch replica of the light pattern. The resulting patterned electron bunch is accelerated, and projected with required magnification to create the desired intensity profile on the targeted tissue. In one aspect, any distortion of the pattern after steering and/or magnification must be within acceptable limits so that the desired intensity profile is delivered to the targeted tissue according to the treatment pattern, typically with spatial positioning accuracy of within 3 mm and intensity within 3% of specified dose at the targeted tissue.

In accordance with various embodiments, the setup includes following parts: light generation, its transport and diagnostics; photocathode electron gun; low aberration electron optics and electron beam diagnostics.

According to some embodiments, the intensity modulation of the electron source may be produced by using a photocathode illuminated by a light source with the corresponding intensity pattern, in effect, an optical image. One implementation is to use a laser as the light source, and a digital light processing (DLP) micromirror array or other intensity modulating device to produce the charge image on the photocathode to be accelerated and steered. The electron beam optics can be designed to maintain the pattern with high fidelity until it reaches the target.

Figure 8A:
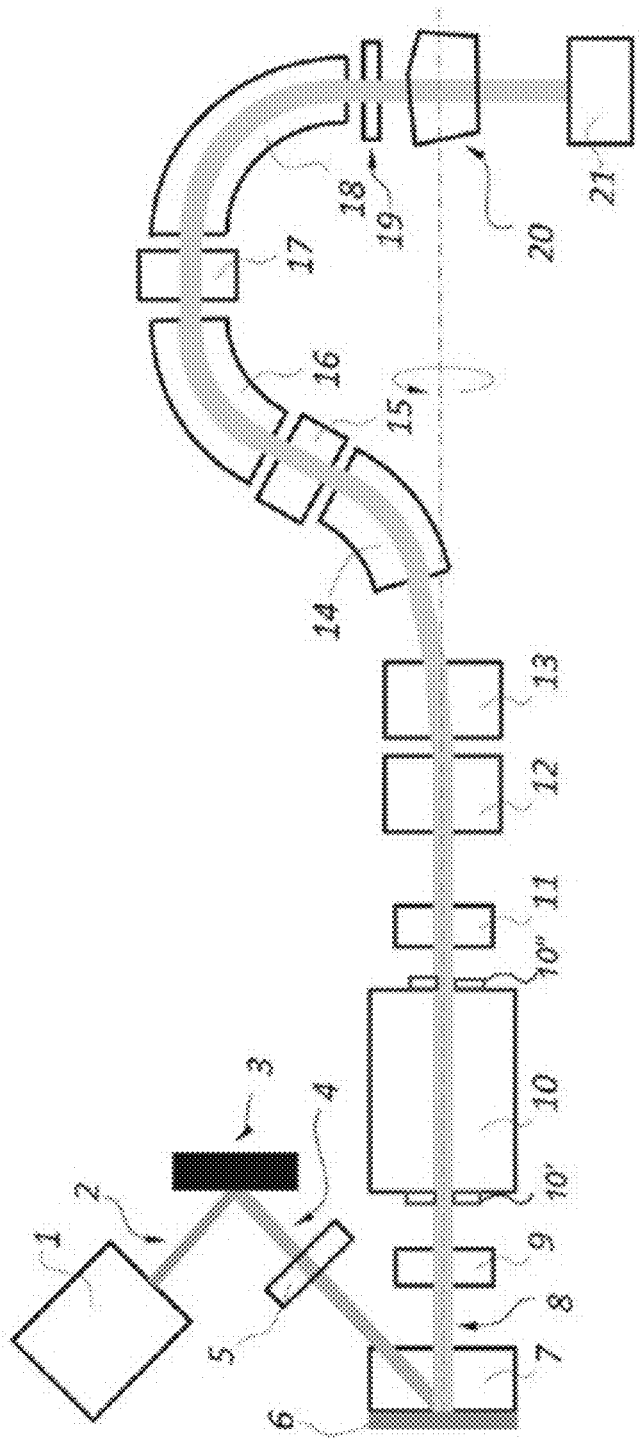
FIGS. 8A-8E schematically show portions of a radiation treatment system with modulation of electron beam transverse profile using pulse-to-pulse modulation of injection laser beam profile impacting a photocathode of an electron injector.

According to one approach, shown in FIG. 8A, a short, typically picosecond-long pulse with substantially uniform transverse profile is generated by a laser 1 (or at least a transverse profile having an intensity distribution that is appropriate to produce the desired pattern at the targeted tissue according to the method described below) The wavelength of the laser is matched with specific photocathode material to obtain required charge and emittance. The laser pulse 2 reflects off a digital-micro-mirror device 3. Pixels of this micro-mirror device are controlled by a computer and will reflect a portion of the laser pulse 4 thus creating an image that is then transferred to the photocathode 6 using precision projection optics 5. Although various types of accelerators may be used with this embodiment, high gradient pulsed devices with a few milliseconds between pulses are preferable. The computer modulates the mirror array thus creating a new image for each consequent pulse. A laser pulse with amplitude-modulated transverse profile that impacts the photocathode 6 will create an electron replica of the laser pulse transverse profile 8. The photocathode 6 is a part of photo-electron gun 7. The gun creates an electric field on the photocathode which accelerates the transverse-modulated electron beam. The gun also provides initial acceleration to boost the electrons to relativistic velocities. The electron beam then passes through the low-aberration focusing system toward accelerator 10. The accelerator increases energy of the beam to a desired value. The electron beam then passes through focusing optics 11 toward horizontal 12 and vertical 13 deflectors. The deflectors are controlled by a computer and are able to send the electron beam in different directions for each consecutive accelerator pulse. The desired direction will depend on (among other things) specific realization of the gantry's beam lines, number of the beam lines and whether they are movable or not. For clarity only one gantry beam line is shown in FIG. 8A. After the deflectors, the electron beam passes through bending magnets 14, 16, 18 and electron optics 15, 17 and is directed through electron-beam monitoring system 19 toward the target 20. The transversely modulated electron beam irradiates the target with required distribution of the dose. After passing through the target, the beam is sent toward beam dump 21 in order to reduce unwanted radiation exposure of the target.

In certain other embodiments, fast deflectors may be used to scan a patterned beam so as to create an effectively larger pattern, which allows the coverage to be increased such as coverage up to 40×40 cm. In certain additional other embodiments, beam deflectors may be used to direct the beam from a single accelerator to more than one beamline, each providing a beam direction toward the targeted tissue. For example, a system having 16 beamlines may require only four electron guns and accelerators if each accelerator feeds four beamlines.

Figure 8B:
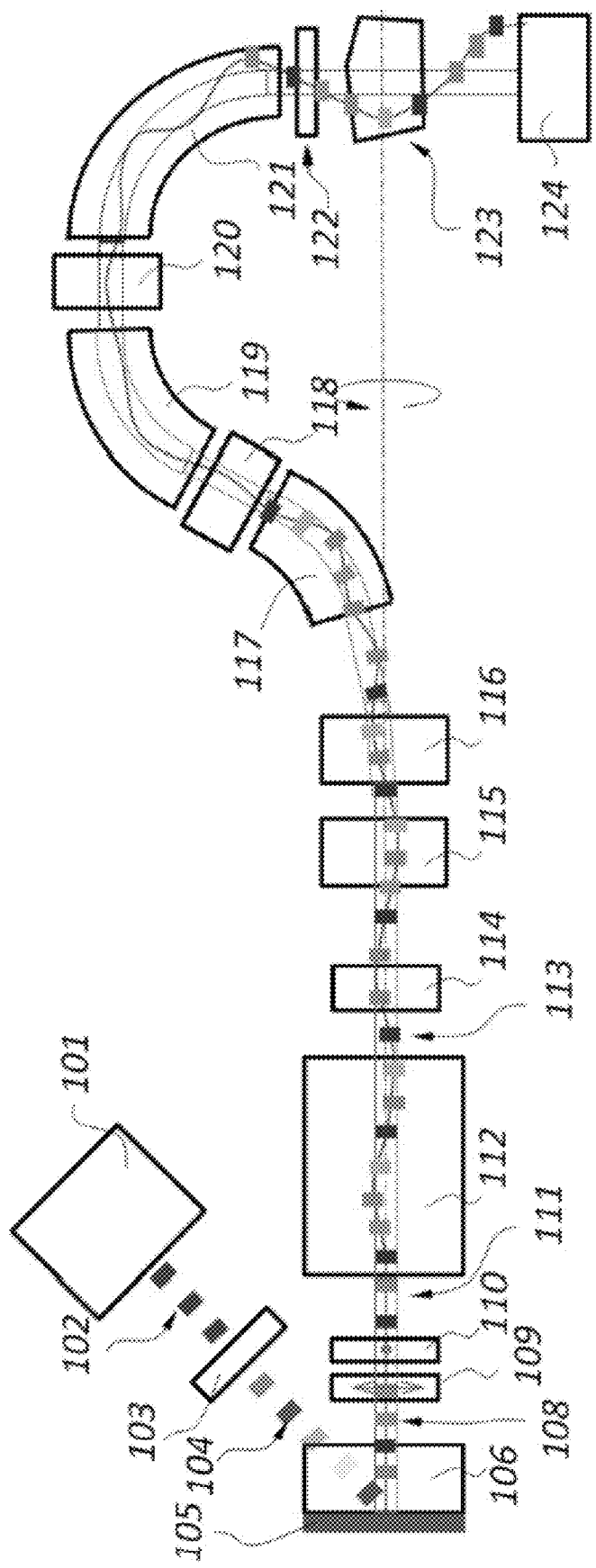

In another approach, the beams having an intensity-modulation directed to the target tissue according to a treatment pattern may be generated by rastering of the beam. FIG. 8B illustrates the concept of a radiation treatment system with pulse-to-pulse modulation of electron beam intensity and rastering of the electron beam at low energy. In this embodiment, a pulsed injection laser 101 generates pulses of laser beams 102, all with the same intensity after which a sub-nanosecond laser beam intensity modulator 103 controlled by a computer forms laser beams with modulated intensity 104 according to the same transverse profile, such that it may be generated by a single spot laser beam. The laser beams having modulated pulse-to-pulse intensity 104 impact the photocathode 105, creating an electron replica of the laser pulse according to the transverse profile. The photocathode 105 is part of a photo-electron gun 106 which creates an electric field on the photocathode that accelerates electron bunches with same transverse profile but with modulated intensity 108 to the fast rastering transverse deflector with vertical kick 109 and the fast rastering transverse deflector with horizontal kick 110 producing low-energy electron bunches with modulated intensity that are rastered in vertical and horizontal directions 111. These low-energy electron bunches are then accelerated in a high gradient electron accelerator 112. The accelerated electron bunches 113 pass through a low aberration lens 114 and horizontal plane and vertical plane magnetic deflectors 115, 116 and are then steered with dipole magnets 117, 119, 121 and focused with low aberration electron lenses 118, 120 for delivery to the targeted tissue. An electron beam monitor 122 may be used to monitor the beam to verify the intensity-modulation according to the treatment pattern before delivery to the target tissue 123. Any remaining beam passing through the tissue is absorbed by electron beam dump 124.

Figure 8C:
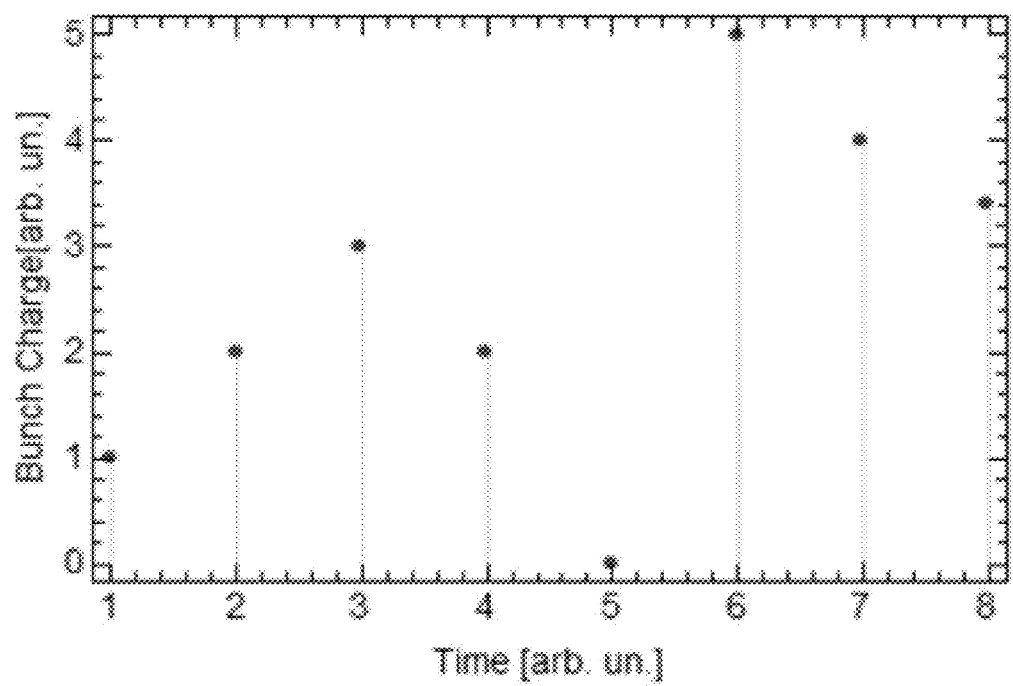
Figure 8D:
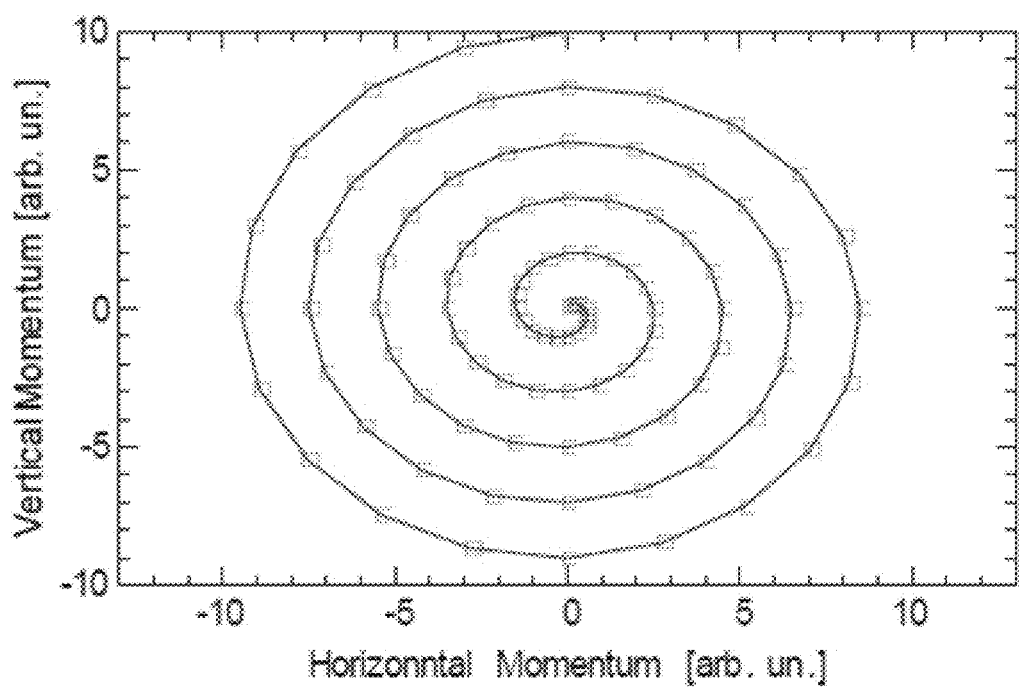
Figure 8E:
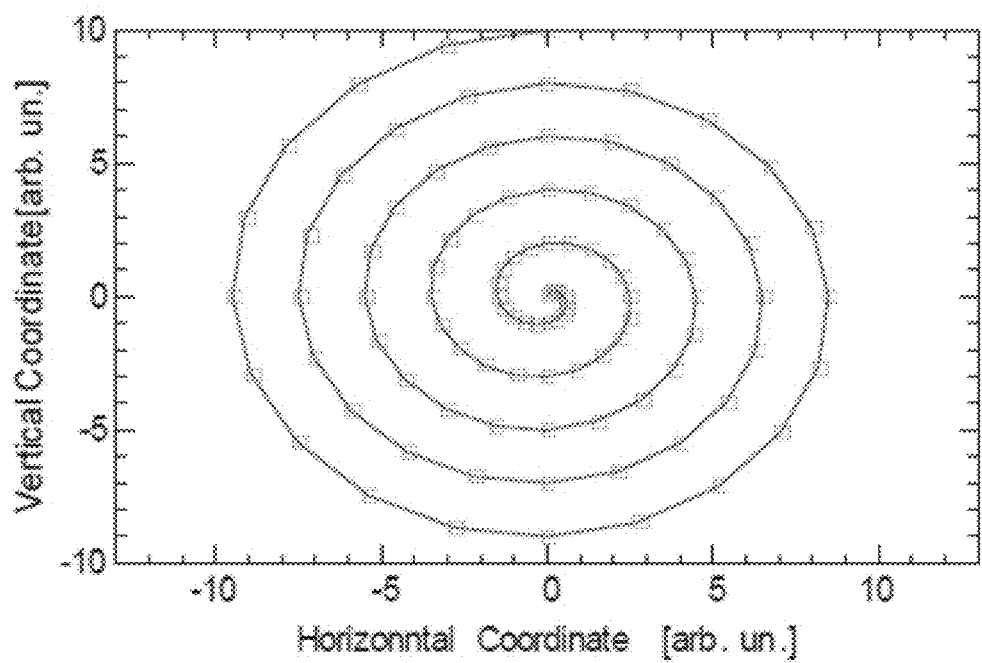

FIGS. 8C through 8E depict various aspects of the rastering approach in FIG. 8B. FIG. 8C illustrates a modulated charge emitted from photo-cathode of photo-electron gun after it exposed to laser pulses with modulated intensity (item 108 in FIG. 8B); FIG. 8D illustrates a plot of vertical and horizontal momenta of electron bunches after passing through two fast rastering transverse deflectors, one with changing vertical kick, another one with changing horizontal kick (item 111 in FIG. 8B). Note that this is but one rastering solutions out of many, as one of skill in the art would be aware. FIG. 8D illustrates a plot of vertical and horizontal coordinate of electron bunches on a targeted tissue (item 123 in FIG. 8B)

Using the same accelerator and beamline transport and magnification optics as required to transport a spatially patterned electron source to the targeted tissue, the same effect can be achieved by modulating charge and transversely rastering an electron point source at low energy, prior to the high energy accelerator. As examples, the electron point source can be created by producing photo-electron point sources at a fixed location on a photocathode, with modulated laser intensity changing pulse-to-pulse charge according to a pre-programmed function, then using fast deflectors to raster the pulses. Another method of creating a rastered electron source is scanning the laser spot with modulated intensity across the photo-cathode to produce required transverse pattern but over multiple pulses. The difference from the concept described in section I.C.3: Ultra-high gradient accelerator structure design is that the spatial modulation of dose in the targeted tissue will be produced by sequential irradiation by multiple pencil beams with pre-programmed intensity, as opposed to irradiating an extended field simultaneously with single or many patterned beams.

Of note, a greater degree of intensity modulation will produce more conformal dose distributions. However, with conventional photon therapy where intensity modulation is delivered in a serial fashion over time, more modulation comes at a cost of longer delivery time, more leakage dose to the patient, and greater uncertainty in delivered dose because of target and organ motion during the longer treatment delivery time and its interplay. With VHEE technology according to certain embodiments of the invention, all of these problems are circumvented: arbitrarily complex intensity modulation can be produced through optical imaging, and rapid parallel delivery eliminates uncertainty from interplay effects.

The concept of conversion of an optical intensity pattern into a radiation intensity pattern within a patient is considered to be unique, and also uniquely applicable to electron beam therapy in accordance with embodiments of the invention as opposed, for example, to photon or proton or other particle therapies. In general, the light-pulse generation could be based on laser, light-emitting diode, or various other light sources with power, wavelength, and pulse length optimized to produce sufficient electron charge and initial emittance from a specific photocathode material.

In some embodiments, the pre-programmed light pattern is imprinted on the light pulse using programmable transparent 2D screens, for example LCD, modulated using programmable mirror arrays (similar to ones used in video-projectors), programmable micro-lens arrays, or programmable deformable mirrors. Using different approach, the light pattern could be generated directly in the light-source from programmable laser or light-emitting-diode 2D array. These programmable devices change transverse light pattern many times per second. Each pattern is synchronized with pulses of electron accelerators in order to generate treatment dose with different transverse pattern on every consequent pulse, again, multiple times per second. The diagnostics of the light pattern is performed simultaneously with the projection of the light on the photocathode, by either splitting light pulse before projection on the photocathode or by imaging the light pulse reflected from the photocathode.

In accordance with the above embodiment, to extract photo-electrons from the photocathodes, the photo-gun exhibits high electric field on its surface, which may be provided by any of DC high voltage, pulsed high voltage, radiofrequency electromagnetic fields or any combination thereof. The photocathode may be transparent or reflective, such as the photo-gun 7 with metal reflective photo-cathode 6 shown in FIG. 10. The materials of the photocathode may include a metal (e.g. copper, magnesium, silver, or other suitable material), dielectric (e.g. diamond), semiconductor (GaAs, etc.), or various compound materials suitable for use in photo-multipliers, streak cameras, various Cs compounds like CsBr, Sb—Cs or materials with a suitable energy gap. The specific photocathode material can be matched in quantum efficiency and light-wavelength to the specific light source. For example UV laser could be used with copper cathode, or CsBr cathode could be used with blue-light laser diode.

In accordance with the above embodiments, the patterned light pulse impacting the photo-cathode creates an electron replica, which is accelerated out of the photo-gun. The electro-magnetic fields of the gun can be configured to preserve phase space of the patterned electron bunch. Prior to delivery, the patterned bunch may be monitored along its path to the targeted area, namely during acceleration, transport and conditioning, by means of invasive electron-bunch diagnostics like phosphor screens, wire scanners, and the like. By use of diagnostics, any drift in the tuning of the instrument to deliver the appropriate pattern to the targeted tissue can be corrected for and a high quality of the delivery of the beam to the targeted tissue can be insured. Monitoring of the electron bunch properties during delivery may be performed with non-invasive diagnostics such as beam position monitors, phase-cavities 10', 10'' (shown as single cells at the entrance and exit of linac 10 in FIG. 8A), ion chambers and the like. The non-invasive diagnostics may record centroid transverse and temporal properties and charge at the time of delivery.

In accordance with the above embodiments, after exiting the gun, the bunch is transported in low aberration electron optics and accelerated in electron-accelerator to required energy 1-250 MeV. The transport and the accelerator are designed to preserve emittance of the bunch by means of low-aberration components. The property of the electron-beam transport allows creation of the pre-programmed dose pattern on the targeted tissue.

Figure 9A:
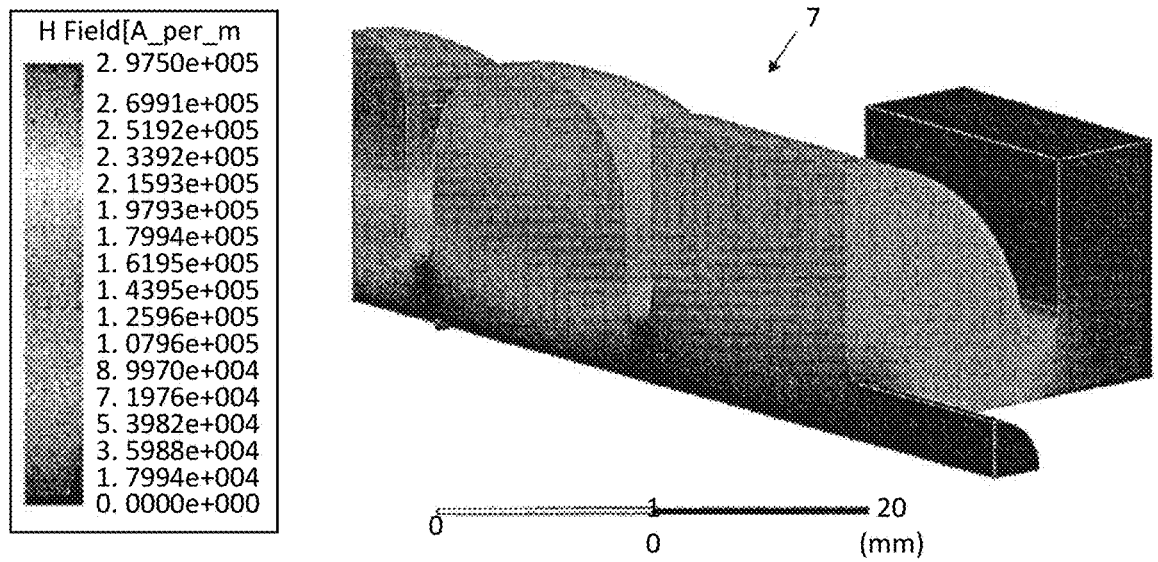
FIGS. 9A-9B illustrate electric and magnetic fields in an example photo-gun in accordance with certain embodiments of the invention.
Figure 9B:
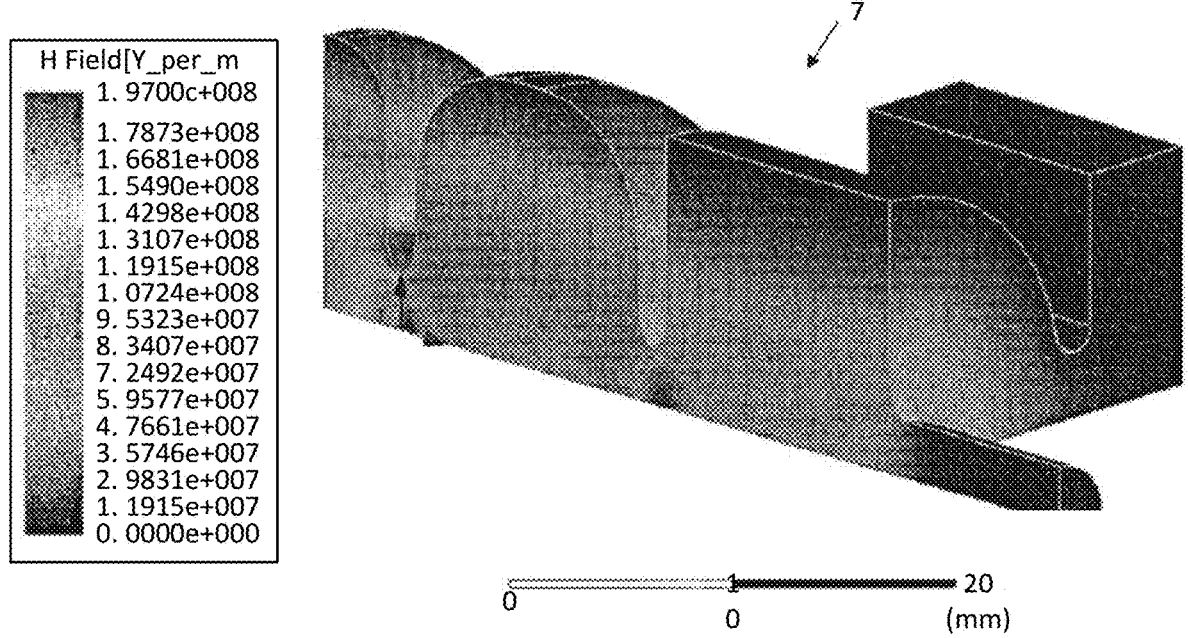
Figure 10:
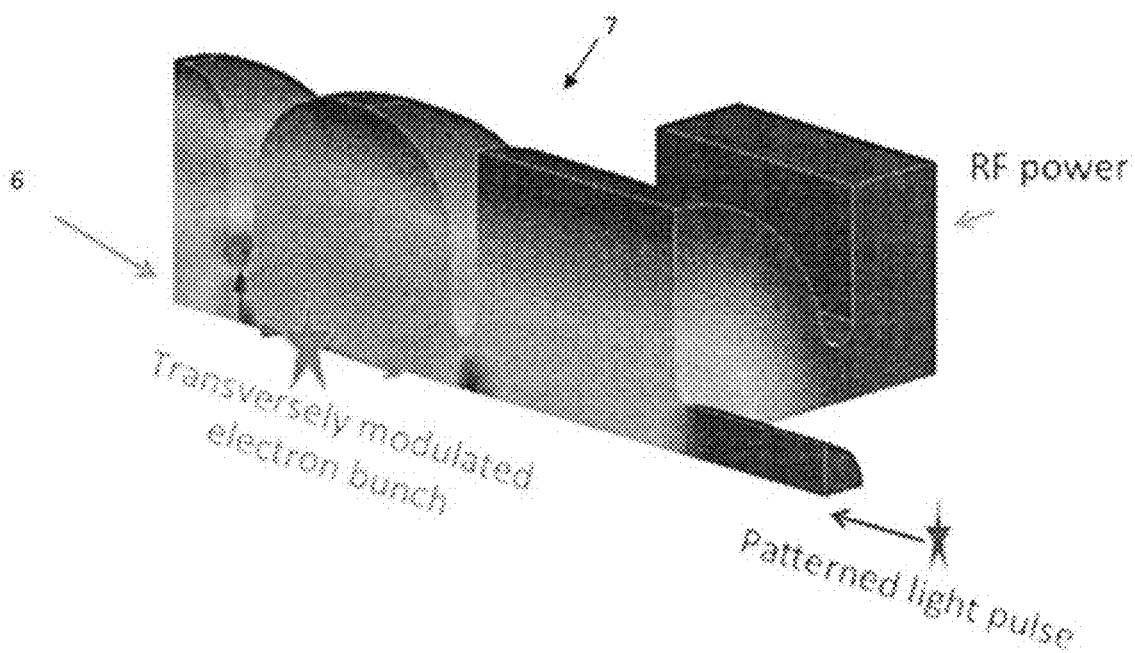
FIG. 10 illustrates associated electric fields in an example photo-gun in accordance with certain embodiments of the invention.
Figure 11:
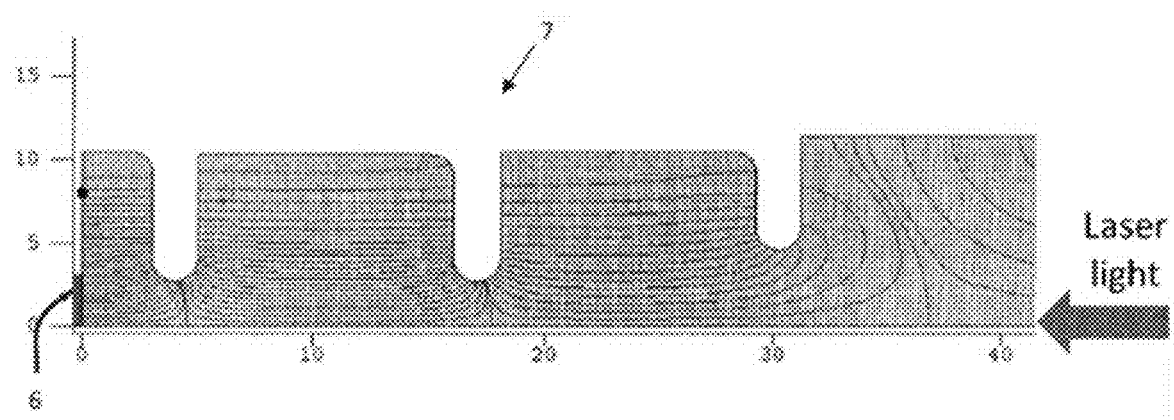
FIG. 11 illustrates an example photo-gun in accordance with embodiments of the invention.

FIGS. 9A-9B illustrates electric and magnetic fields in an example 9.3 GHz photo-gun suitable for use with the above described embodiments (only one-quarter of the photo-gun being shown). FIG. 9A illustrates surface electric fields and FIG. 9B illustrates surface magnetic fields. FIG. 10 illustrates the 9.3 GHz photo-gun and associated electric fields shown in FIG. 11 and further illustrates the various components and direction of the patterned light pulse suitable for use with the above described embodiments. In some embodiments, the photocathode 6 on which the source treatment pattern is formed includes a CesiumBromide (CsBr) coating. In this example, the peak electric field on the cathode is 164 MV/m for 2 MW of input power. The electric fields can be optimized to preserve bunch emittance. The advantages of using such a design for delivering the radiation include rapid and precisely shaped dose delivery far beyond that of conventional technologies. In addition, this configuration allows for dose modulating and shaping without requiring movement of mechanically moving parts, thereby allowing far more rapid delivery than would be possible with delivery systems used in conventional radiation treatments. This allows delivery of a precise 3D distribution of whole-treatment dose in reduced treatments times, such as delivery of an entire treatment dose in less than a minute, such as less than 10 seconds, preferably one second or less, or even more preferably delivery in a sub-second time, which is not feasible with conventional treatment systems.

The above described embodiments utilizing a photo-gun are particularly suited for treatments with high-energy electron beams, although it is understood that this feature may be used with various other radiation treatment systems including treatment with X-rays. In one such example, a transverse modulated electron beam may be directed to a bremsstrahlung X-ray target combined with X-ray collimators. This combination allows formation of a transversely patterned X-ray dose, which allows delivery of an entire treatment dose in a very short time.

In one aspect, use of a photo-gun, as described in the above embodiments, provides improved rapid, pulse-to pulse modulation of the transverse beam for use in medical accelerators. A medical accelerator with high-energy (50-250 MV) electron beam produces sufficient treatment dose using relatively small charge well within the parameter ranges of the present invention. As one of skill in the art would understand, the above described feature utilizing a photo-gun may be used in various differing radiation systems, including those described herein. The source should be able to produce a spatially modulated pattern of electron emission, with low transverse emittance and longitudinal emittance (compatible with the required compactness of the beamline optics and with the RF frequency). Examples include RF powered guns with photocathodes (currently the most practical option), but other designs for patterned electron emission sources are possible and may become more practical in the near future.

In certain aspects, the patterned electron beam is accelerated, transported, and magnified to the appropriate size to cover the targeted tissues in the patient. The shape, resolution, and contrast of the pattern must be preserved throughout this process. The size of the pattern on the source is typically a few millimeters and thus the smallest feature size or resolution must be a few micrometers. To cover field sizes treated in general radiation therapy (typically up to 30-40 cm), the degree of beam magnification by the time it reaches the patient is on the order of 100-200, and may be different in the two transverse directions if desired.

Figure 12:
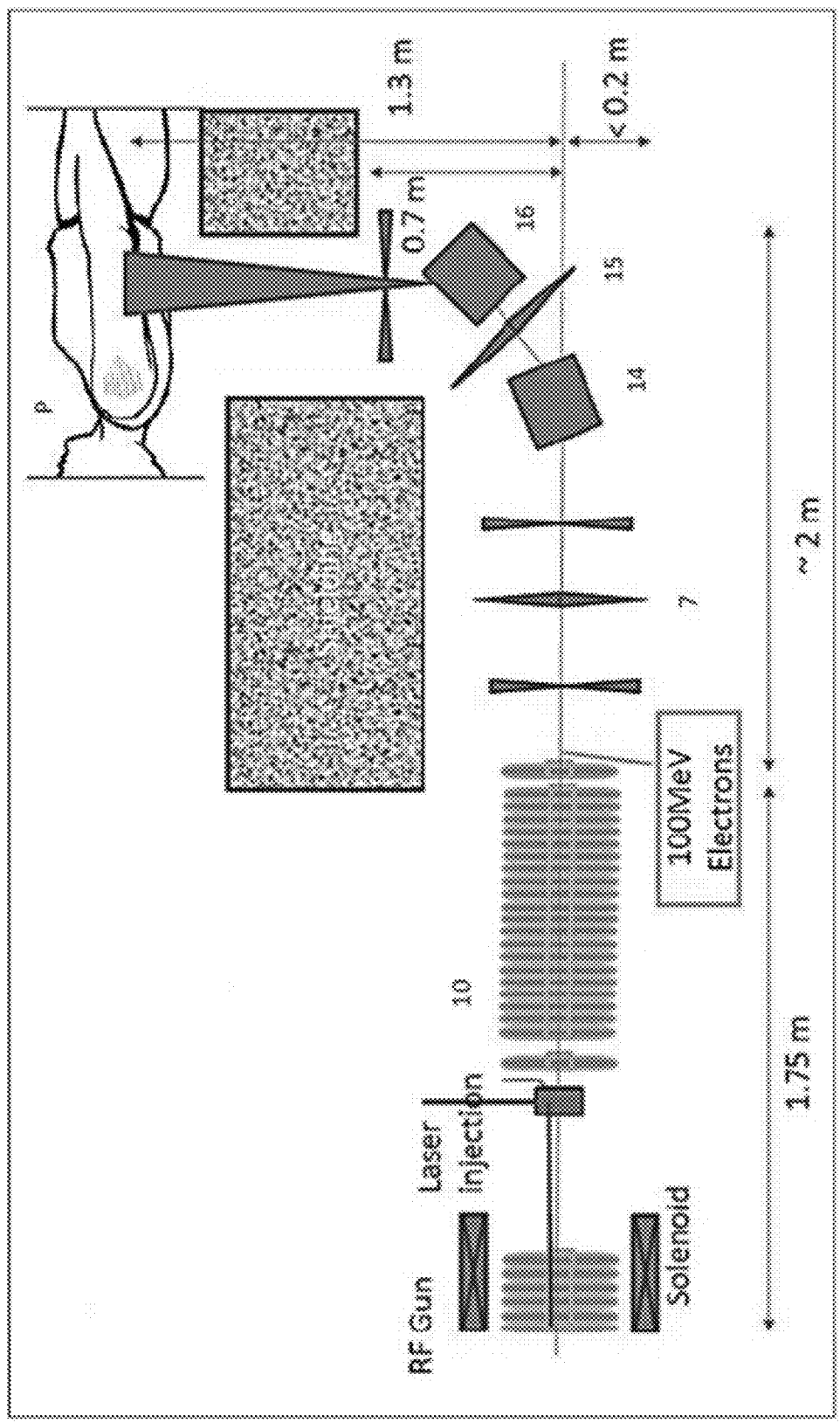
FIG. 12 illustrates a schematic of a beamline in an example treatment system in accordance with certain embodiments of the invention.

FIG. 12 shows one possible compact beamline implementation (only one beamline is shown for clarity) in which the entire system fits within a typical size radiation therapy vault. A series of magnets is included to bend and magnify the beam after acceleration through the linac 10. In the embodiment shown, the linac is 1-m long and accelerates the electrons to form a 100 MeV electron beam, after which the beam passes through focusing optics 7, such as a series of quadrupole magnets, then is steered by use of bending magnets 14, 16 alternating with electron optics 15 to direct the electron beam to the targeted tissue in the patient P. This beam dynamics simulation shows that an electron pattern of less than 2 mm at the source with minimum feature size of about 10 micrometers can be accelerated, transported (including bending toward the patient), and magnified to a final size of nearly 20 cm in this example (about 100 times magnification), with preservation of the pattern including the finest features, such as shown in example pattern of FIG. 13A). FIG. 12 shows an example of a single angle delivery system at the most constraining bending angle (90 degree) from beam generation, acceleration, transport with steering and magnification; the last magnet ends at 60 cm from the patient axis. While various embodiments may be described as having certain dimensions, it is appreciated that these concepts may be used in systems having various other dimensions and configurations to obtain the advantages described herein.

In one aspect, the pattern imprinted on the photo-generated electron beam at the emission from the cathode is chosen to match the required pattern needed at the patient targeted tissue, compensating for aberrations in the beam source, accelerating and transport systems. The steering system and magnifying system of the multiple beamlines occupies a compact space (for example less 3 meters, the height of existing therapy vaults). In some embodiments, a first very strong small aperture electromagnetic lens acts on the small size beam exiting the accelerator. The subsequent electromagnetic lenses have lower strength, compatible with larger apertures as the beam starts expanding. This combination makes all electromagnetic lenses small enough to accommodate the multiple beamlines. In some aspects, steering may be performed by one or more focusing elements, which may include permanent magnets, electromagnets, electro-magnetic lenses or combinations thereof. Typically, dynamic steering of high energy beams is performed by electro-magnetic deflection, that is forces generated by both electric and magnetic fields.

In certain embodiments, a beam spreader (12,13 in FIG. 8A and 115,116 in FIG. 8B) can be used after the accelerating structure to feed in multiple distribution lines up to a few kHz rate to deliver beam to the patient from the various angles using a single common accelerator, thus simplifying the RF distribution system and the footprint. For this case, the laser generation system rapidly (again few kHz rate) switches the modulation pattern sent to the single photocathode matching the different patterns needed at the multiple delivery angles.

In some embodiments, a rapidly changing two-axis electromagnetic steerer can be added after the last electromagnetic lens to cover up to 40×40 cm of targeted tissue. Typically, the time needed to switch this steerer strength is less than the time elapsed between 2 consecutive deliveries to the same arm of the multiple angle arms. Variations of this rastering solution can be used to relax the requirement on magnification to 50 or less. It is appreciated that the 40×40 $cm^2$ coverage noted above is but one example of a desired maximum field size that may be typical for a photon treatment system and that various other configurations providing coverage for larger areas may be realized depending on the application. For example, the technologies described herein may be utilized for various other applications, including but not limited to cargo scanning and non-destructive scanning (e.g. testing/analysis of materials or components in bridges or buildings). Application of these technologies for such applications may necessitate variations in the examples described herein suited for the particular application of interest.

Figure 13B:
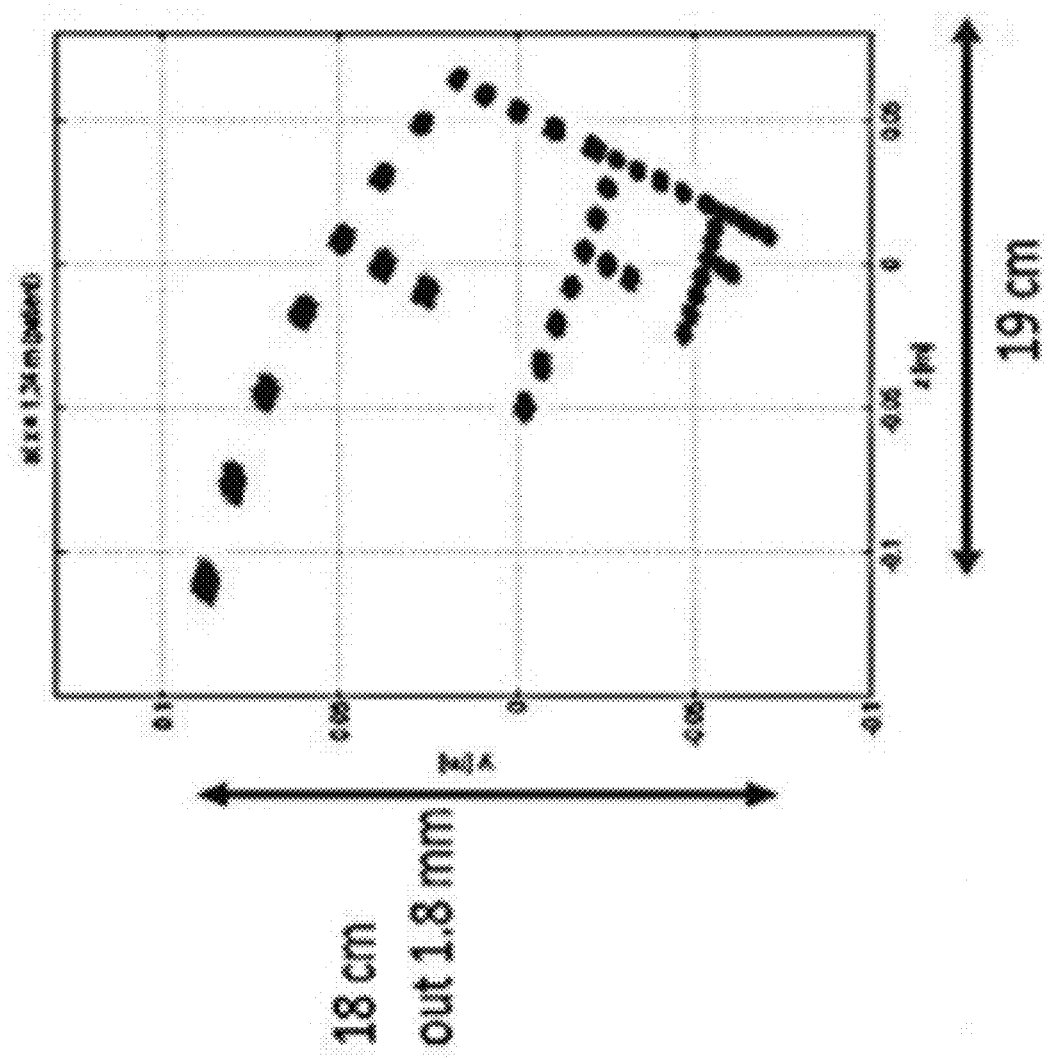
FIGS. 13A-13B illustrate treatment patterns at the source and at the targeted tissue, respectively, after steering and magnification of the intensity-modulated beam in accordance with certain embodiments of the invention.
Figure 13A:
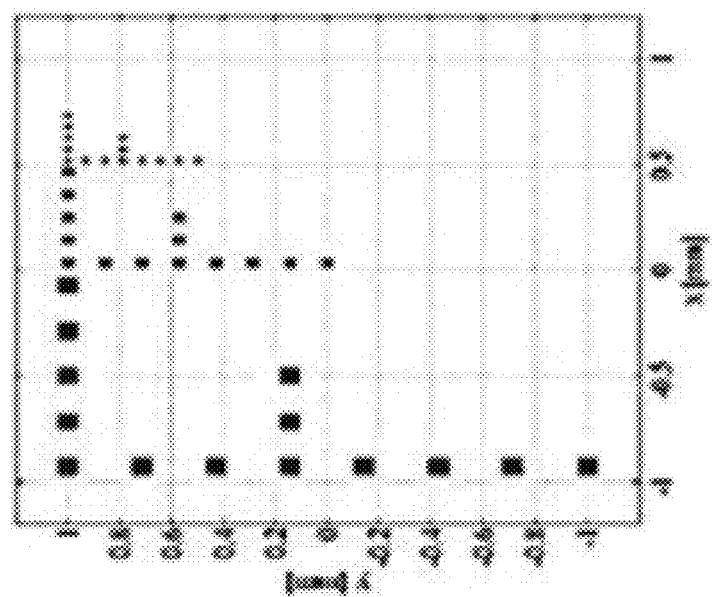

FIGS. 13A-13B show an example of a modulated pattern sent to a photocathode (FIG. 13A) and imaged at the patient targeted tissue (FIG. 13B). In addition to being steered to the targeted tissue, the pattern may be magnified as needed to cover the appropriate treatment area. In this example, the pattern has a magnification of 100 in both planes. As can be seen, there may be variations in the pattern that occur during steering and/or magnification due to non-linearities in the electron beam optical components. These variations may be compensated for in the electron optics, during steering, with the focusing optics, or by adjusting the original pattern on the photocathode. The original pattern may be selected and/or altered so that the resulting electron intensity profile at the targeted tissue after steering and/or magnification is the desired electron intensity profile.

C. Photon Collimation System

In accordance with some embodiments of the invention, the system may utilize a collimation system configured for rapid generation and delivery of transversely modulated photon beams to targeted tissue for radiation therapy. In certain embodiments, the device includes a scanning pencil-array collimated high-speed intensity-modulated X-ray source (SPHINX). Such a device may include a high efficiency collimation system for high energy X-rays produced in medical accelerator. In contrast to conventional collimators, this collimation system allows reduced x-ray irradiation times when combined with an electron beam of sufficient current because the irradiation speed is not limited by slow mechanical motion, thus allowing the ultrafast delivery of radiation to the targeted tissue desired in a rapid radiation treatment system, including those described therein.

In certain aspects, the precision transverse distribution of the photons is generated by rastering electron beam pulses from a linear accelerator onto an array of photon production targets or sheet-shaped target. By controlling the intensity or number of individual electron bunches at each position, the transverse intensity distribution can be shaped as needed for treatment.

In accordance with some embodiments, the system operates as follows: electron bunches from a high repetition rate electron accelerator are rastered onto an array of photon production targets. By controlling the individual electron bunch intensity the produced transverse photon distribution from the array target can be modulated as required by the treatment. Because the electron bunch intensities and positions can be varied electromagnetically, the transverse photon beam shaping does not require movement of mechanically moving parts, thereby enabling far faster treatment times than in conventional radiation treatments.

In order to achieve the sub-second treatment times the array photon source can be combined with an improved high repetition rate linear accelerator and an improved target/collimator design for photon production. In addition, the forward photon intensity characteristics of the photon beam potentially can be improved over the traditional high-Z target photon production schemes by several strategies including using different target materials (e.g. lower-Z materials to favor forward production) and different target/collimation geometries (e.g. pin targets, hole targets, cone targets, glancing beam photon production, as would be known to one of skill in the art, or other strategies as described below in the example variations.

Figure 18A:
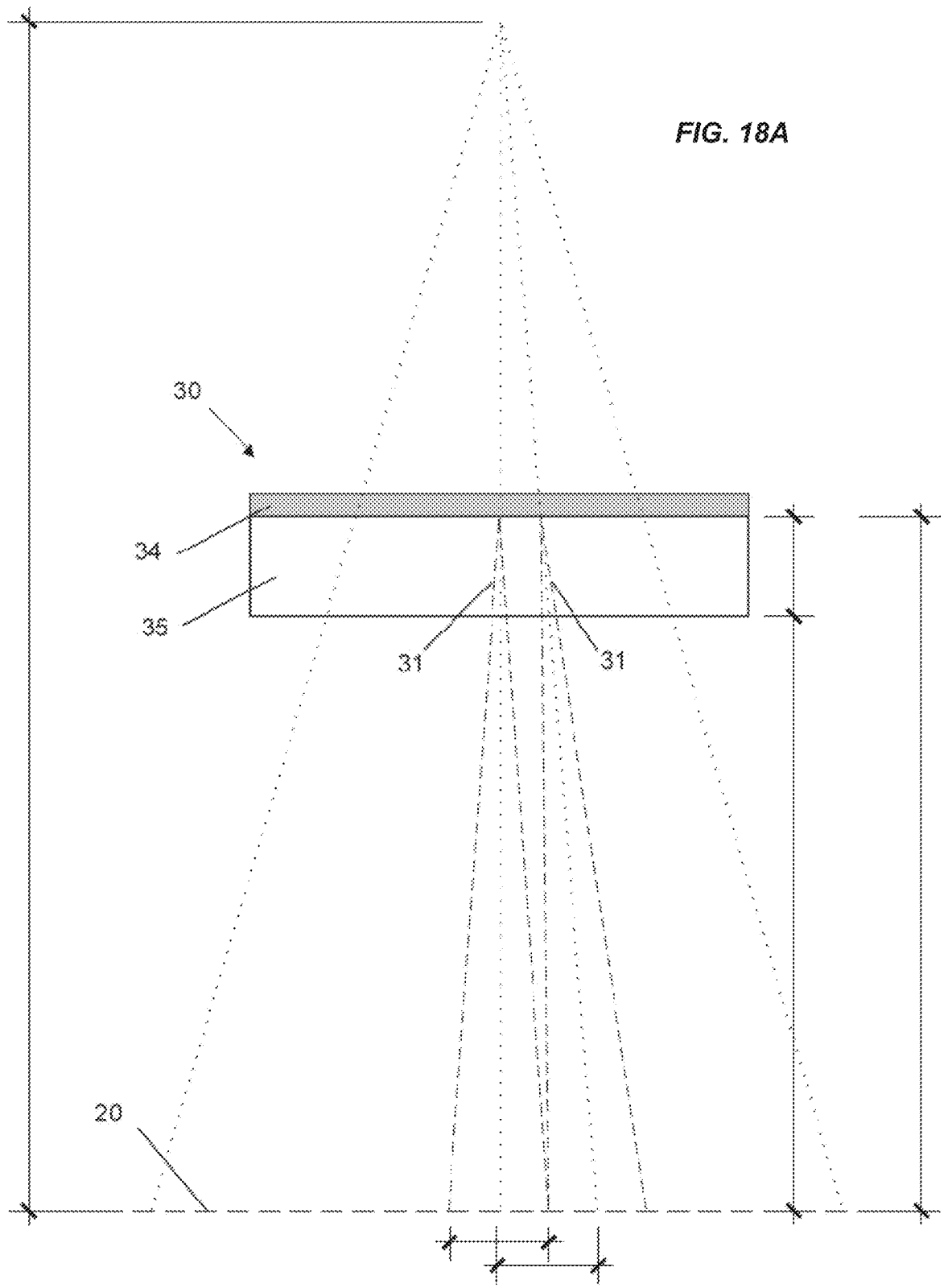
FIG. 18A shows a conceptual schematic channel configuration in which the photon beamlets diverge from one another. They are dosimetrically matched without a gap in the plane of the targeted tissue in this example. Channel spacing may also be chosen such that the beamlets overlap in the plane of the targeted tissue.

According to certain aspects, it is desirable that the 2-D dose distribution produced by the array of pencil beams from any given direction not have dosimetric gaps owing to the space between beams. As shown for example in FIG. 18A, the space between collimator channels 31 should be sufficiently small that the penumbra of individual beams is sufficient to fill the gaps between beams at the targeted tissue location 20. Conversely, the penumbra should be sufficiently sharp that there is good contrast and resolution in the intensity-modulation pattern. Both goals can be fulfilled simultaneously by optimizing the spacing and wall thickness between channels and the length of the channels. The spacing between channels may allow for overlap between the resultant beamlets, perfect matching, or gaps between beamlets. An advantage of overlapping beamlets is more choices for placement of individual beamlets for finer targeting, and better field uniformity when using multiple adjacent beamlets. The desired intensity pattern will range from uniform coverage of a large area to very highly modulated patterns with high spatial resolution and contrast.

Figure 14A:
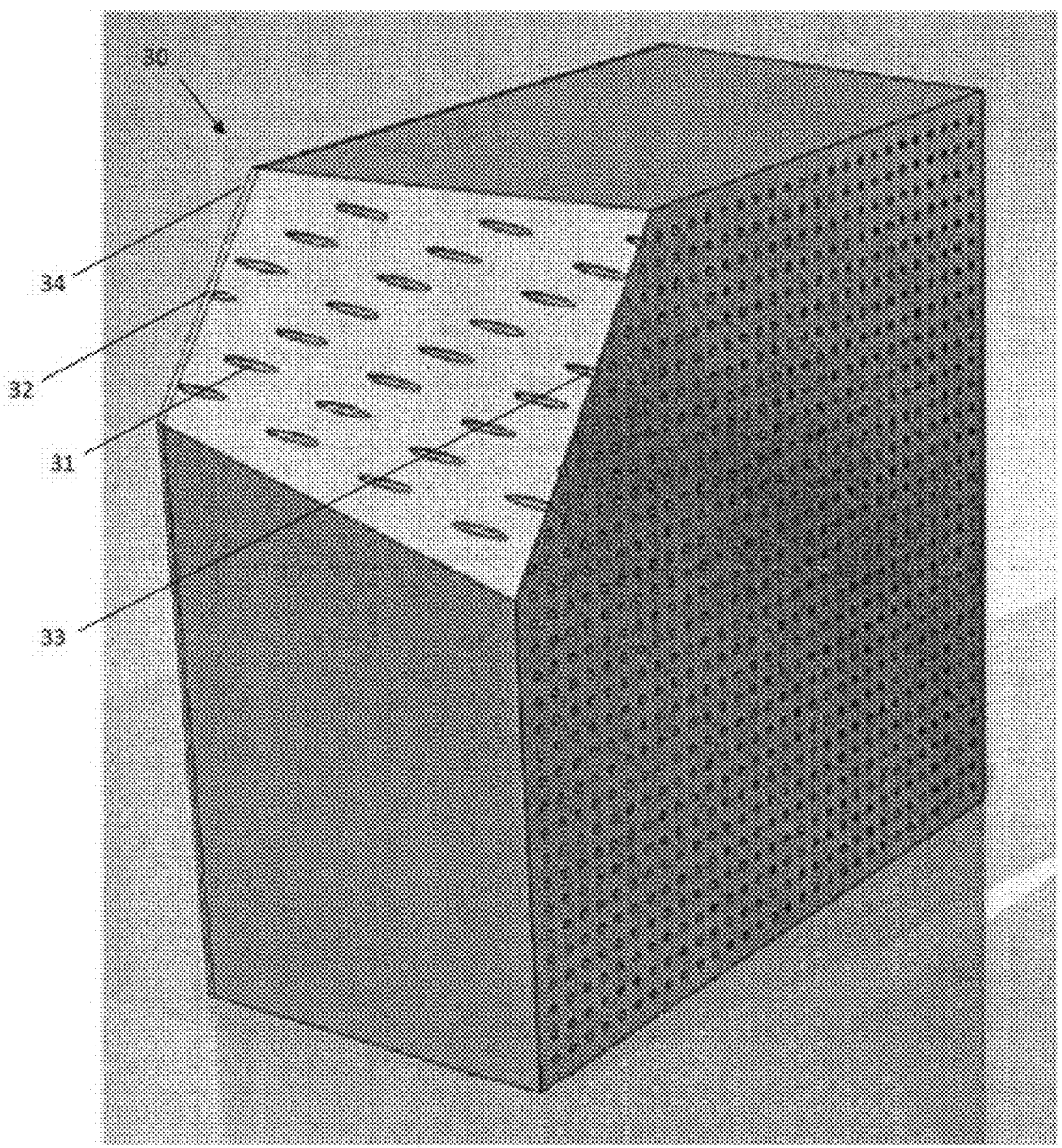
FIGS. 14A-14B illustrate examples of collimator assemblies for use in a rapid radiation treatment system.
Figure 14B:
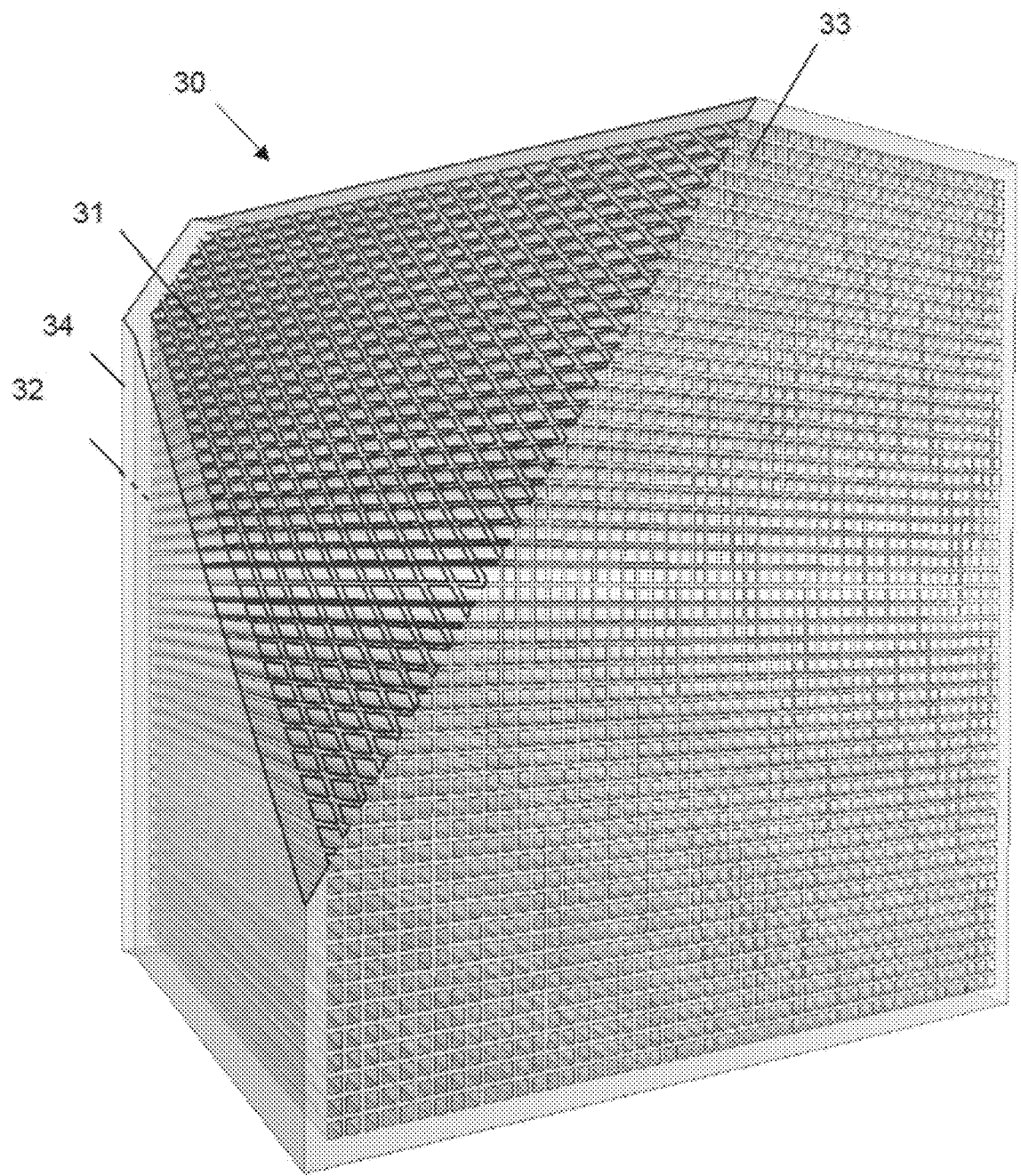

FIGS. 14A-14B illustrate schematics of such a source in an example embodiment, showing the collimator block 30 with its upstream surface abutting a bremsstrahlung target 34 and an array of channels 31 extending through the block to collimate the photon beams produced by the bremsstrahlung target 34. For easier visualization in the figure, the spacing between holes is not to scale and represented larger than would be used for this purpose. In one aspect, such as shown in FIG. 14A the channels 31 are circular in cross-section and extend from an inlet hole 32 at the upstream surface of the collimator block 30 and extend to an outlet hole 33 at the downstream surface of the collimator block 35, the outlet hole 33 being larger than the inlet hole 32. In another aspect, the channels 31 are square or rectangular in cross-section, such as shown in FIG. 14B and described further in later examples, the channels extending from an inlet hole 32 at the upstream surface of the collimator block 30 and extend to an outlet hole 33 at the downstream surface of the collimator block 32, the outlet hole 33 being larger than the inlet hole 32. In some embodiments, each channel 21 tapers from the smaller inlet hole 32 to the larger outlet hole 33. While in this embodiment, the channels generally taper at a fixed rate, in other embodiments, the taper may of a variable rate or the channels may have a fixed diameter along certain portions and taper in certain other portions of the block.

In one aspect, this source design is useful for a photon source in a radiation treatment system in accordance with the present invention. The enhanced ability is particularly advantageous for sub-second treatment times for radiation therapy for cancer and other diseases. It is appreciated that the underlying technology for enhanced forward photon production can also be used for various radiation treatment, including those with longer treatment times, as well as various non-medical applications (e.g. truck/cargo scanning for security applications).

Among the advantages of the design described above is rapid and precisely shaped dose delivery as compared to existing technologies. In addition, this design allows for dose modulating and shaping without requiring movement of mechanically moving parts. The source/target characteristics are further improved, as compared to conventional treatments, so as to allow further reductions in dosage delivery times, including sub-second dose delivery for treatment of cancer and other diseases. This design allows for improved collimation characteristics and does not require use with multi-leaf collimators that require mechanical motion to intensity modulate the radiation.

Another advantage of SPHINX compared to MLCs is improved compatibility with external magnetic fields such as those used in MRI-guided radiation therapy systems, because of lack of electric motors and reduced magnetic materials while still maintaining the ability to intensity modulate the photon beam and perform dynamic target tracking with the photon beam (e.g., for targets in the heart or other rapidly moving targets).

Figure 18B:
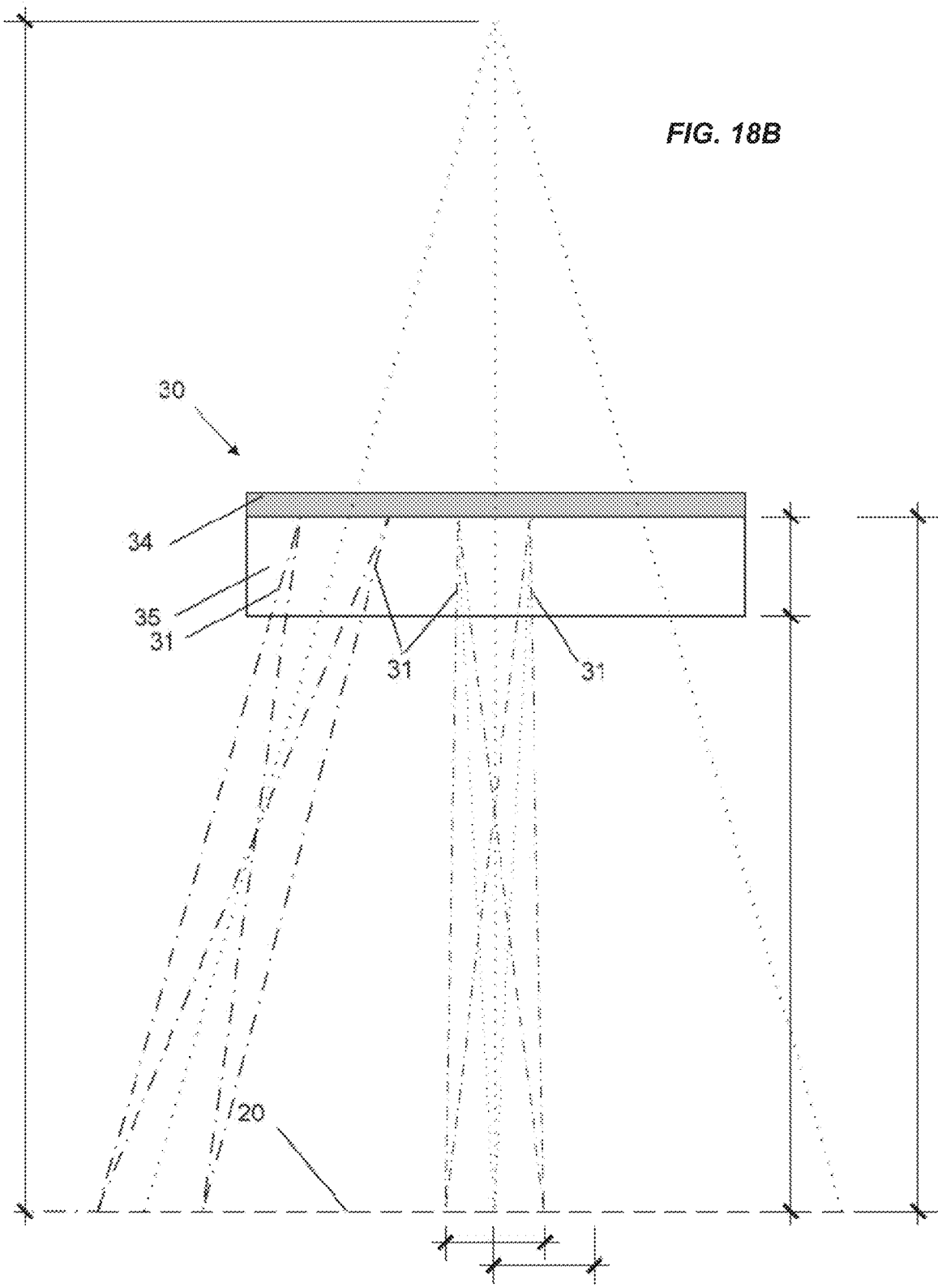
FIG. 18B shows a conceptual schematic channel configuration in which clusters (pairs in this example) of channels converge to a focus in the plane of the targeted tissue, and different clusters form beamlet clusters that diverge from each other. Other sophisticated geometries are possible.
Figure 18D:
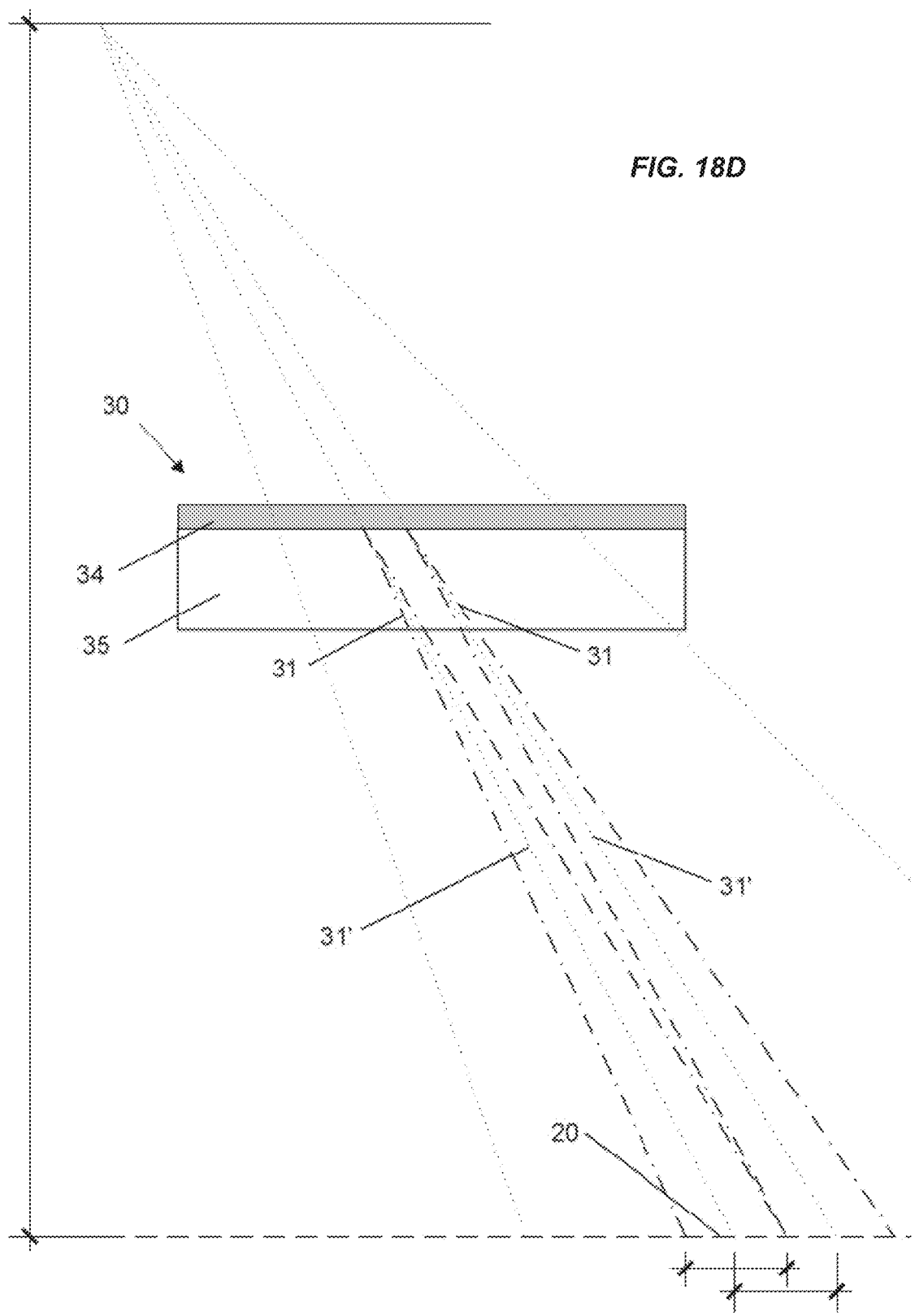
FIG. 18D shows a conceptual schematic channel configuration of an example collimator assembly in which the channels are largely at an oblique angle to the upstream and downstream faces of the block.
Figure 19A:
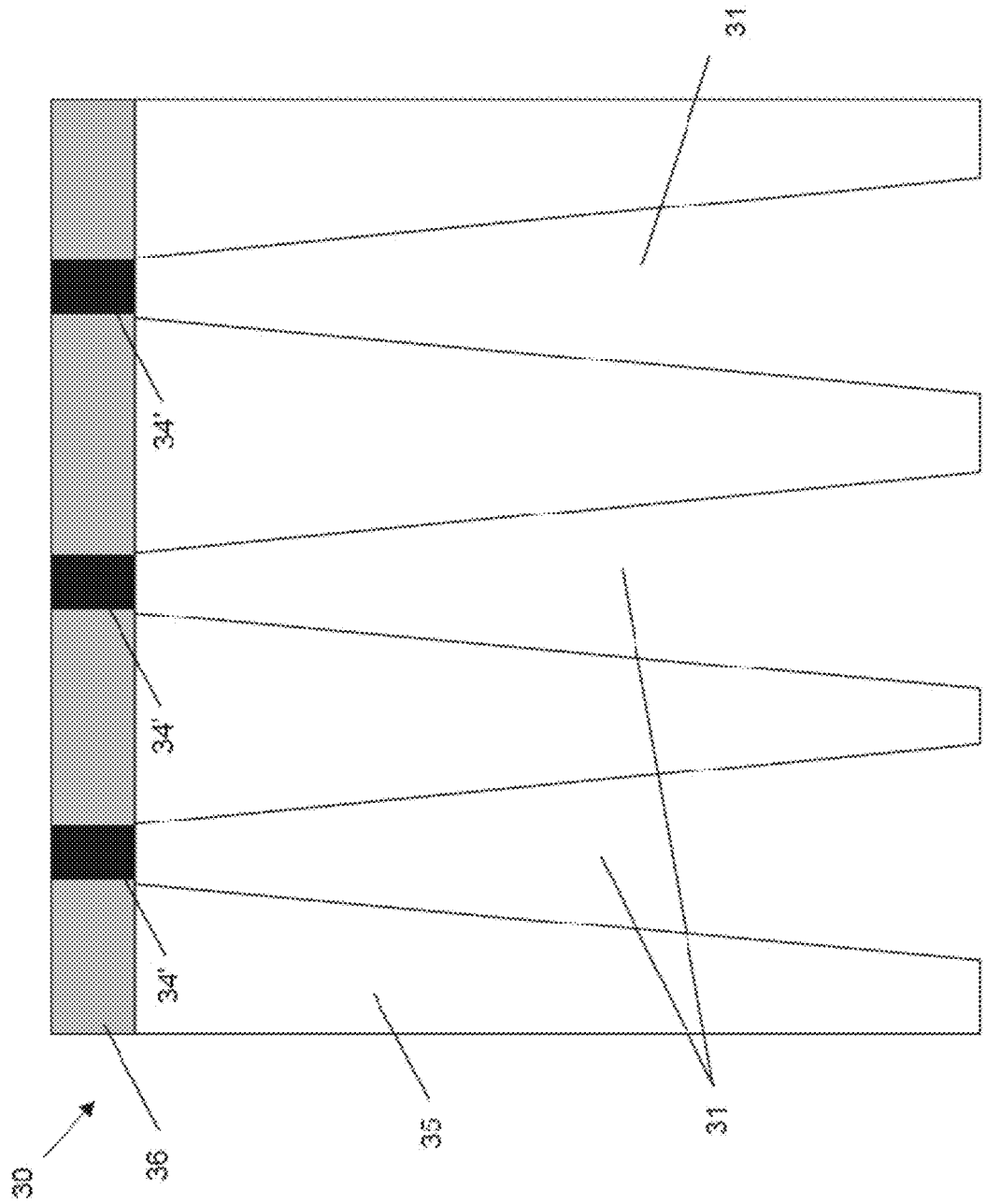
FIG. 19A shows a bremsstrahlung target array comprising tungsten plugs aligned with the collimator channels, embedded in a layer of copper for heat dissipation and conduction.
Figure 19B:
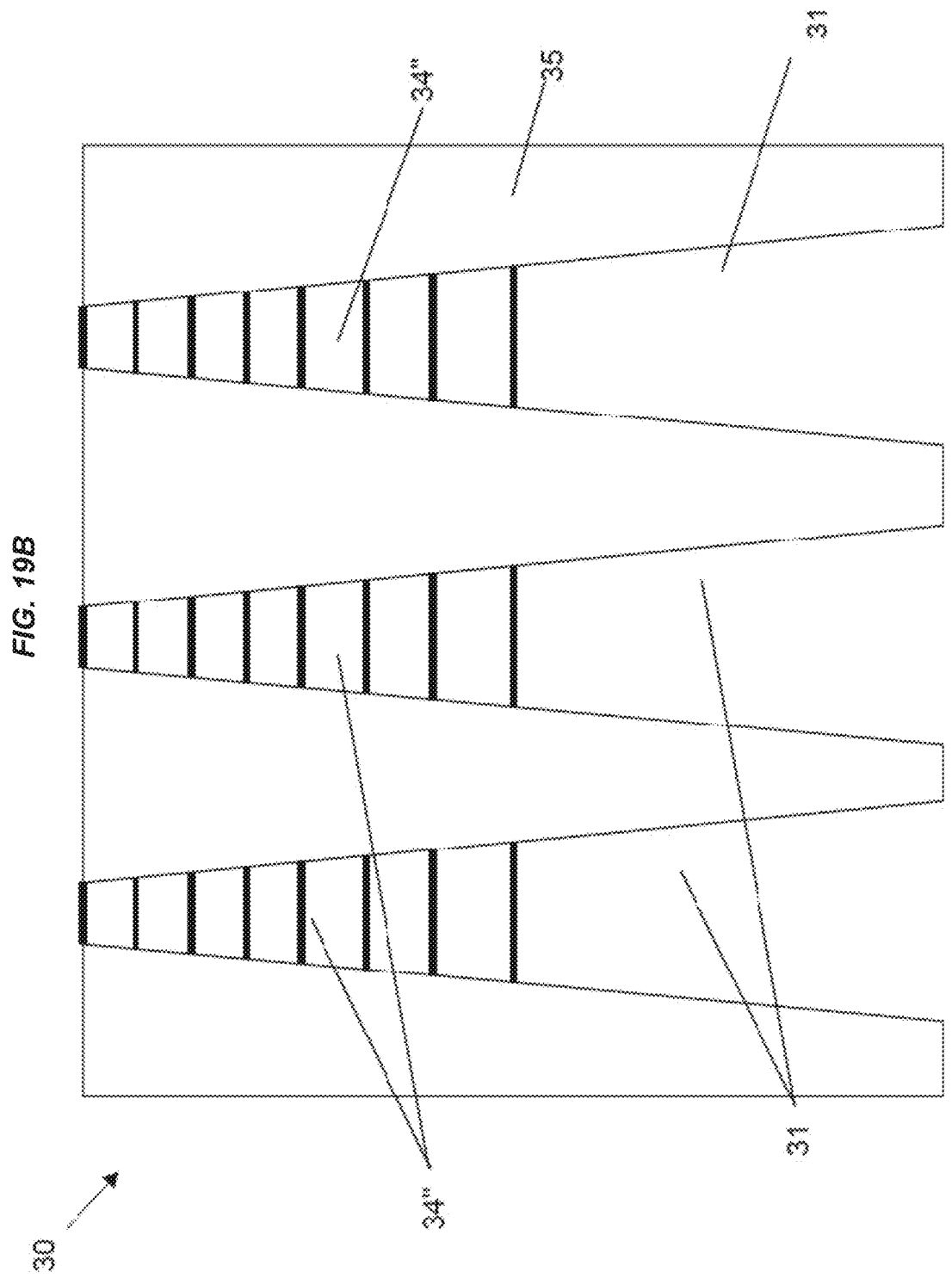
FIG. 19B shows bremsstrahlung targets comprising multiple thin layers of tungsten distributed along the length of each channel with fixed or variable spacing between layers.

It is appreciated that the collimator configuration described above may be varied in a number of ways in keeping with the principles of the invention, including the following examples:

a. The collimator array consists of channels whose central axes diverge from the source to the targeted tissue, in order to cover large-volume targets in the patient (see for example FIGS. 18A, 18C and 18D);

b. The collimator array consists of channels 31 whose central axes 31' are parallel or converge from the source to the targeted tissue 20 (see for example FIG. 18B), which is more suitable for covering smaller-volume targets in the patient;

c. The collimator array has channels 31 with a square profile (see for example FIG. 14B);

d. The collimator array has channels with a non-square profile that may have more optimal area packing (eg, hexagonal, circular, etc.) or edge enhancement characteristics (see for example FIG. 14A);

e. Rather than an array of channels, the collimator array can be formed by an array of slits (diverging, parallel, or converging) in one direction in tandem with an array of slits in the perpendicular direction. A potential advantage of this design is greater ease of manufacture than an array of pencil beam channels, at the cost of greater space requirement;

f. Different channel sizes may be incorporated into the same array in order to improve photon throughput, with more photons being delivered using larger channels and finer shaping using smaller channels, such as shown for example in FIG. 18C. Alternatively, a similar effect can be achieved through a combination of arrays (e.g., one per treatment head in a multi-beamline system) with each array having a different channel size and configuration. Alternatively, on a given treatment head, a choice of collimator arrays of different channel configurations may be used (e.g., by mounting them on a carousel to allow switching between arrays). The choice of array or individual channels used in the plan can be made through treatment planning optimization;

g. The channel configuration within a given array may be more complex, for example, consisting of clusters of converging channels but with the clusters diverging from each other, such as shown for example in FIG. 18B. Such an arrangement would allow large field coverage with improved depth dose characteristics;

h. Strategies for heat dissipation include active target cooling, multiple rapid rescanning of the electron beam over the array, and incorporation of appropriately configured heat conducting materials. In some embodiments, such as shown in the example of FIG. 19A, the bremsstrahlung target may be formed by an array of plugs 34' of target material, such as tungsten or other suitable material, aligned with the collimator channels 31 in the collimator block 35, the array of plugs being embedded in a layer heat conducting material 36, such as copper or other suitable material. In addition, the collimator array itself can serve as a heat sink for the target if they are abutting.

i. Strategies for increased forward photon production include applying electric and/or magnetic fields to refocus the electron beam within the bremsstrahlung target and choice of target and wall materials, and dividing the target material into multiple thin layers 34" along the beam direction to allow electron refocusing between layers, such as shown in the example of FIG. 19B. It is understood that a separation between target layers may be fixed or variable to optimize the refocusing effect. A subset of these aspects can be further understood by referring to the article: W. Ulmer, "On the creation of high energy bremsstrahlung and intensity by a multitarget and repeated focusing of the scattered electrons by small-angle backscatter at the wall of a cone and magnetic fields—A possible way to improve linear accelerators in radiotherapy and to verify Heisenberg-Euler scatter," Radiation Physics and Chemistry 81 (20120 387-402), the entire contents of which are incorporated herein for all purposes.

j. The channels may traverse through the block material at oblique angles so that the collimator array may be mounted at an angle to the beamline for more compactness in certain embodiments, such as shown in FIG. 18D-18E;

k. The transmission bremsstrahlung target will be interposed between the electron beam and the collimator array. Typically, it would consist of a layer of high atomic number such as tungsten although a range of materials may be appropriate. The thickness of the target may be uniform or variable according to an optimized design.

In one aspect, a system includes one or more treatment heads, each having a suitable collimation assemblies disposed within for use in a radiation treatment of a targeted tissue in a patient. In some embodiments, the one or more treatment heads are coupleable with any of a set of collimator assemblies having different shapes and/or geometries, such as any of those described therein, which are selected by a user as desired for a given treatment. In some embodiments, the system includes a rotating carousel having multiple differing collimating assemblies such that selection of a particular collimating assembly can be effected by rotation of the carousel. In another aspect, the collimating assemblies can be removable from the treatment heads such that the desired collimating assemblies are selected and attached to the treatment heads in preparation for the procedure.

Figure 18E:
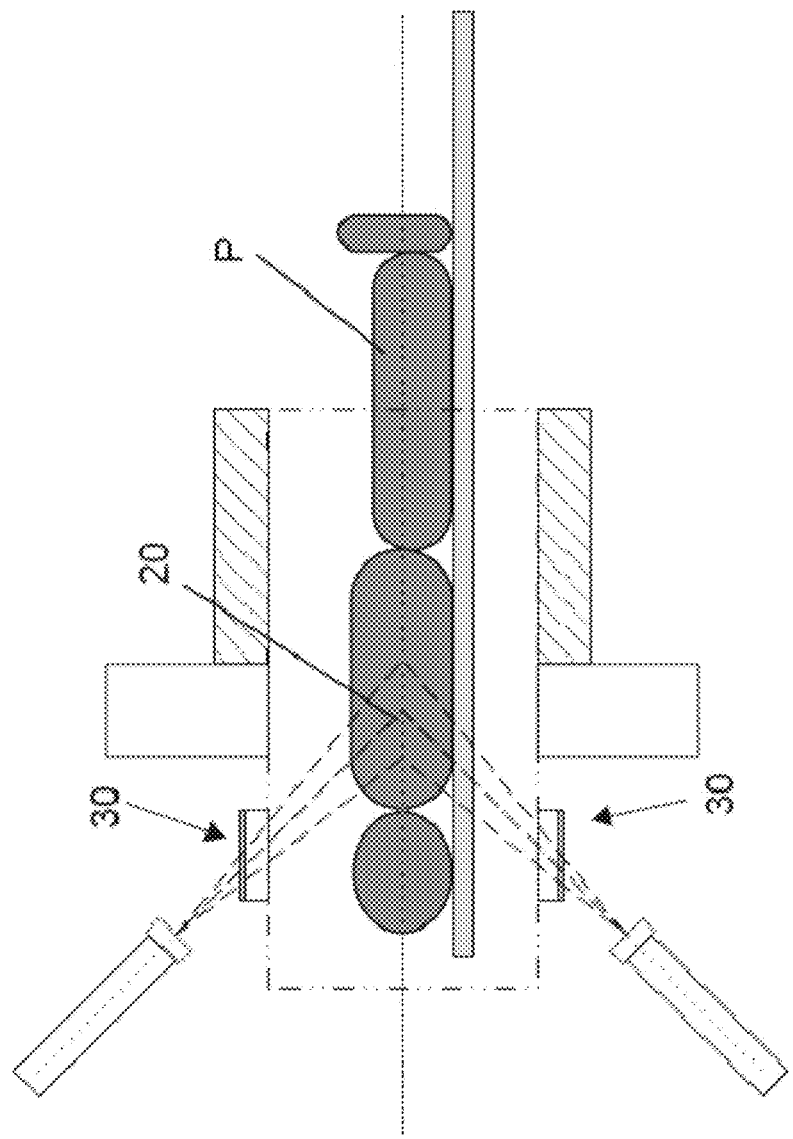
FIG. 18E shows a schematic of a treatment system utilizing the example collimator assembly in FIG. 18D.

In another aspect, one or more beamlines with one or more corresponding collimator arrays may be on a rotating gantry to create a larger number of beam directions as illustrated in FIG. 18E, which for simplicity shows 2 beamlines with two beam directions or alternately one beamline rotating between two directions.

Figure 18F:
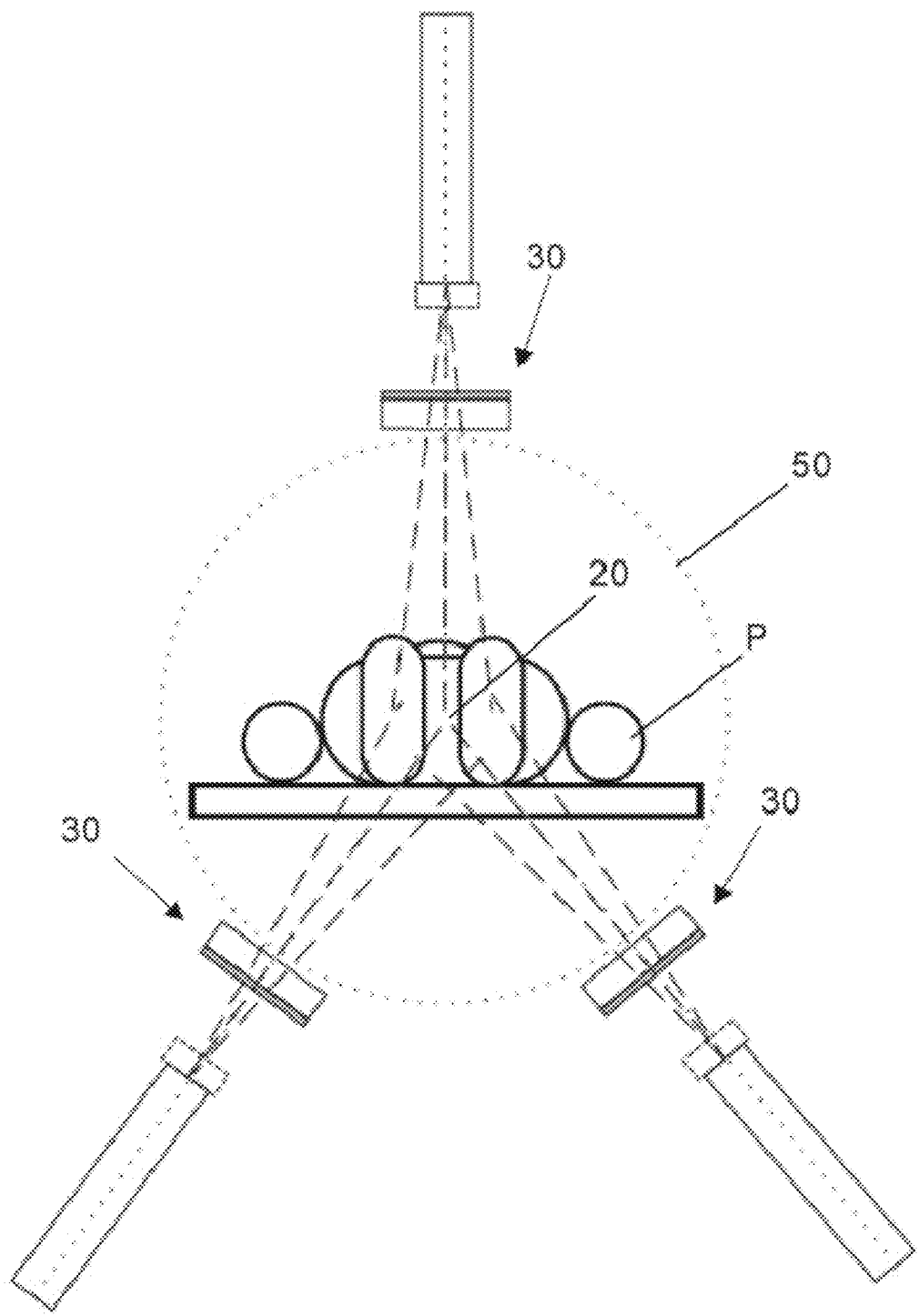
FIG. 18F shows a schematic of a treatment system having a rotating gantry that includes collimation assemblies, in accordance with aspects of the invention.

In one aspect, the system may include a rotating gantry 50 having one or more beamlines and collimation assemblies thereon so as to allow collimated beams from multiple differing directions. In some embodiments, a rotating carousel may be used include one or more collimation assemblies or multiple collimation assemblies with differing geometries. FIG. 18F shows an example of coplanar beamlines perpendicular to the patient, in which there are multiple beamlines, or in the alternative, FIG. 18F may represent a single or a few beamlines and a rotating gantry supporting multiple beamlines and collimation assemblies affixed thereon. Of note, a collimation assembly, such as the SPHINX collimation structure may, be used together with conventional energy electron linacs (up to ~20 MeV). In some embodiments, the beamlines may utilize transport/ magnifying optics rather than a SPHINX collimation structure. Rotation of the gantry allows the beamlines and collimation assemblies to direct beams toward the targeted tissue from different directions as needed. In some embodiments, rotation of the gantry would be a requirement if the number of beamlines is small (for example, less than seven beamlines). In addition, these aspects may apply to a system in which the beamlines are noncoplanar and at an oblique angle to the patient axis.

Figure 18G:
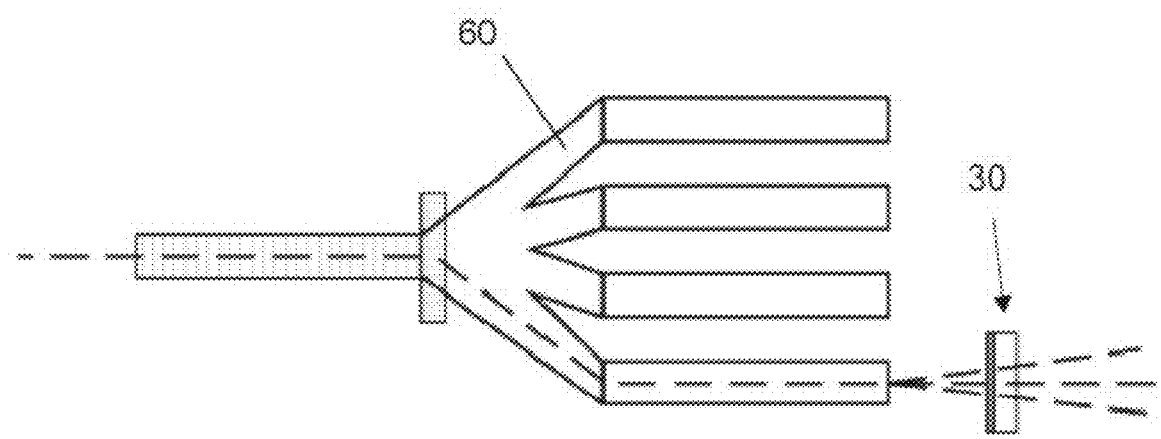
FIG. 18G shows a treatment system having multiple beamlines from a single accelerator for use with or without a collimation assembly, in accordance with aspects of the invention.

FIG. 18G illustrates a schematic of an example system where a single electron linear accelerator feeds multiple beamlines (four beamlines in this example) in a multi-beamline structure 60. A beam deflecting device may be configured to move the beam between the different beamlines. Each beamline may be used with a collimation assembly, such as a SPHINX structure, (only one being shown in FIG. 18G) if the appropriate energy range, or the beamlines may be used without a collimation assembly such as in a very high energy electron beam treatment.

In one aspect, a system includes one or more treatment heads, each having a suitable collimation assemblies disposed within for use in a radiation treatment of a targeted tissue in a patient. In some embodiments, the one or more treatment heads are coupleable with any of a set of collimator assemblies having different shapes and/or geometries, such as any of those described therein, which are selected by a user as desired for a given treatment. In some embodiments, the system includes a rotating gantry having multiple differing collimating assemblies such that selection of a particular collimating assembly can be effected by rotation of the gantry. In another aspect, the collimating assemblies can be removable from the treatment heads such that the desired collimating assemblies are selected and attached to the treatment heads in preparation for the procedure.

Figure 15:
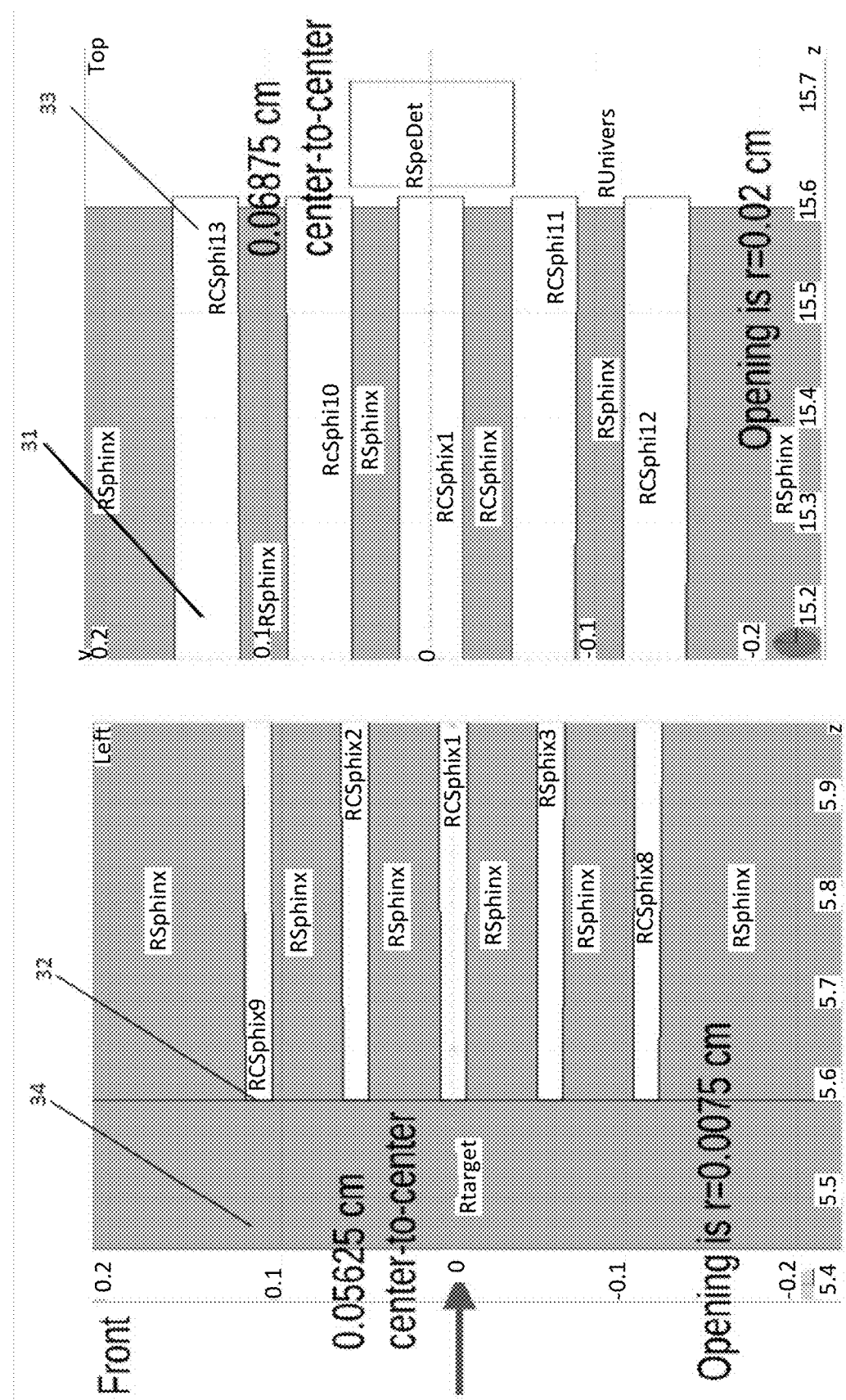
FIG. 15 illustrates a cross section of the channels through a collimator assembly in accordance with certain aspects of the invention.

Another example geometry for a SPHINX collimation assembly is shown in FIG. 15. In this case, the electron beam impinges on a tungsten target 34 of 1.5 mm thickness to produce bremsstrahlung x-rays. Immediately downstream of the bremsstrahlung target is the collimator array, consisting of a 10 cm thick block of tungsten with diverging channels. The channel size is such that each forms a photon beamlet of 3 mm diameter at a distance of 65 cm from the downstream face of the SPHINX, and the spacing is such that the beamlets are 1.5 mm apart (center to center) at that distance, and thus fully overlap by a half-width when adjacent beamlets are formed. This configuration allows finely spaced beamlet selection as well as no dosimetric gap.

FIG. 15 shows a cross-sectional view along the channels at the upstream side and at the downstream side of the collimator 30. The projected width of the photon beamlet at the plane of the targeted tissue depends substantially on the thickness of the collimator block and the diameter of the outlet hole, which is chosen accordingly. The size of the inlet hole should be dimensioned sufficiently large enough to accept the size of the electron beam that forms the x-ray source in the bremsstrahlung target, and would generally be smaller than the size of the outlet hole. For example, in the embodiment shown, each channel 31 has an inlet hole 32 with a half-width of 0.0075 cm and an outlet hole 33 with a half-width of 0.02 cm. This results in a beamlet width at the plane of the targeted tissue (65 cm downstream of the downstream face of the collimator) of approximately 3 mm in this example. In one aspect, the center to center spacing distance between outlet holes is larger than each outlet hole diameter, so that there is sufficient wall thickness to provide adequate collimation of the x-ray beamlets. The center-to-center spacing between channels determines the beamlet spacing at the plane of the targeted tissue. Diverging, parallel, or converging beamlets are produced if the spacing at the downstream surface is larger, equal, or smaller than at the upstream surface. In this embodiment, the center-to-center spacing distance between exit holes is 0.06875 cm, while each outlet hole width is 0.04 cm. At the upstream surface of the collimator 30, along which the bremsstrahlung target 34 is positioned, in this example embodiment, the center-to-center spacing is 0.05625 cm between inlet holes, each inlet hole having a width of 0.015 cm. This produces a set of diverging beamlets with 3 mm width and 1.5 mm spacing in the plane of the targeted tissue, and a virtual focal point 120 cm upstream of the plane of the targeted tissue in this example.

Figure 16:
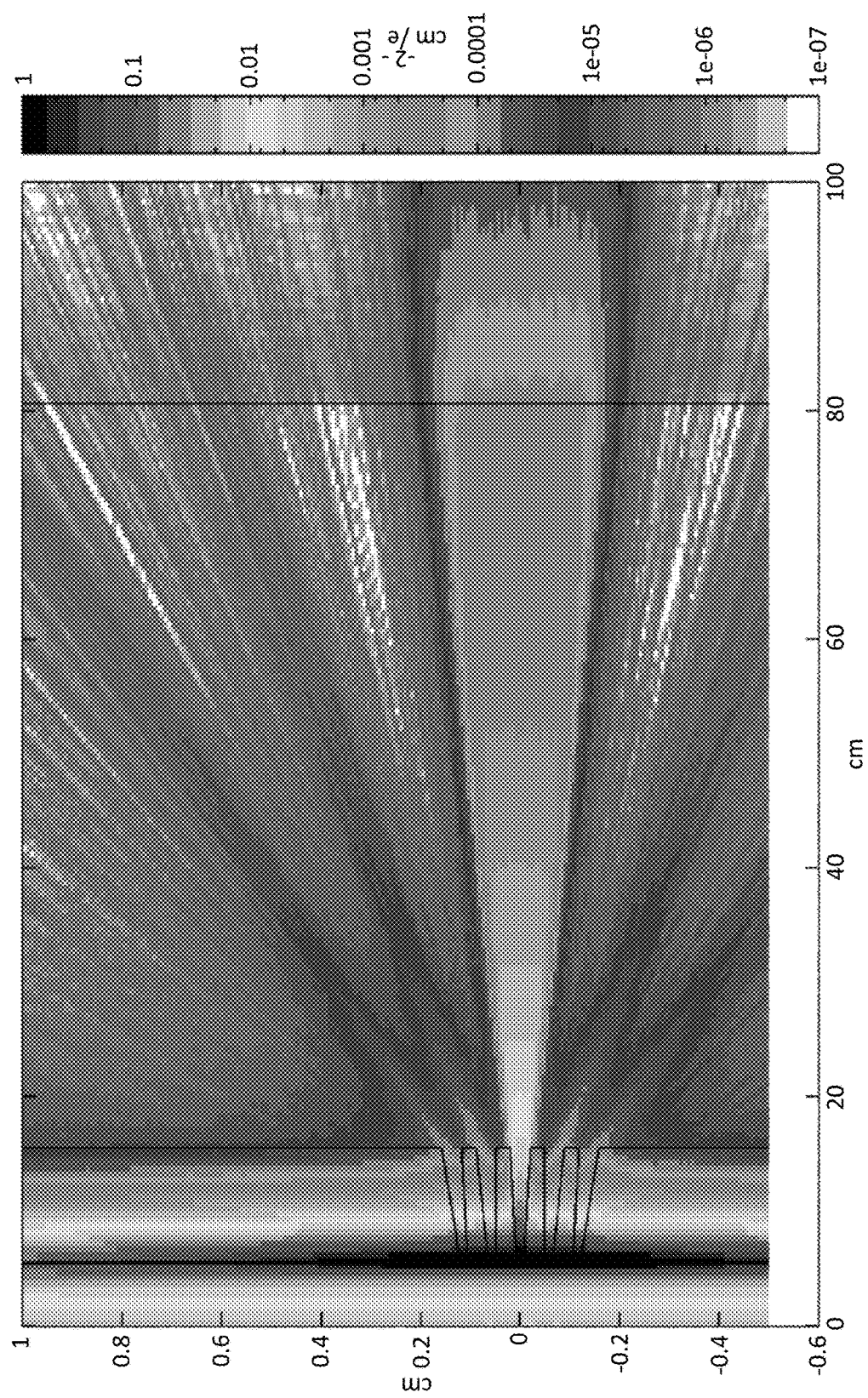
FIG. 16 shows photon fluence when one channel is illuminated by an electron beam of 10 MeV energy in accordance with certain aspects of the invention.

FIG. 16 shows the photon fluence when one channel is illuminated by an electron beam of 10 MeV energy (the bottom channel on the figure) as determined by FLUKA Monte Carlo simulation visualized with FLAIR. (See FLUKA: a multi-particle transport code" A. Fasso', A. Ferrari, J. Ranft, and P. R. Sala, CERN-2005-10 (2005), INFN/TC_05/11, SLAC-R-773; "FLUKA: a multi-particle transport code," A. Fasso', A. Ferrari, J. Ranft, and P. R. Sala, CERN-2005-10 (2005), INFN/TC_05/11, SLAC-R-773; and FLAIR, V. Vlachoudis "*FLAIR: A Powerful But User Friendly Graphical Interface For FLUKA*" Proc. Int. Conf. on Mathematics, Computational Methods & Reactor Physics (M&C 2009), Saratoga Springs, N.Y., 2009; each of which is incorporated herein by reference in its entirety).

Figure 17:
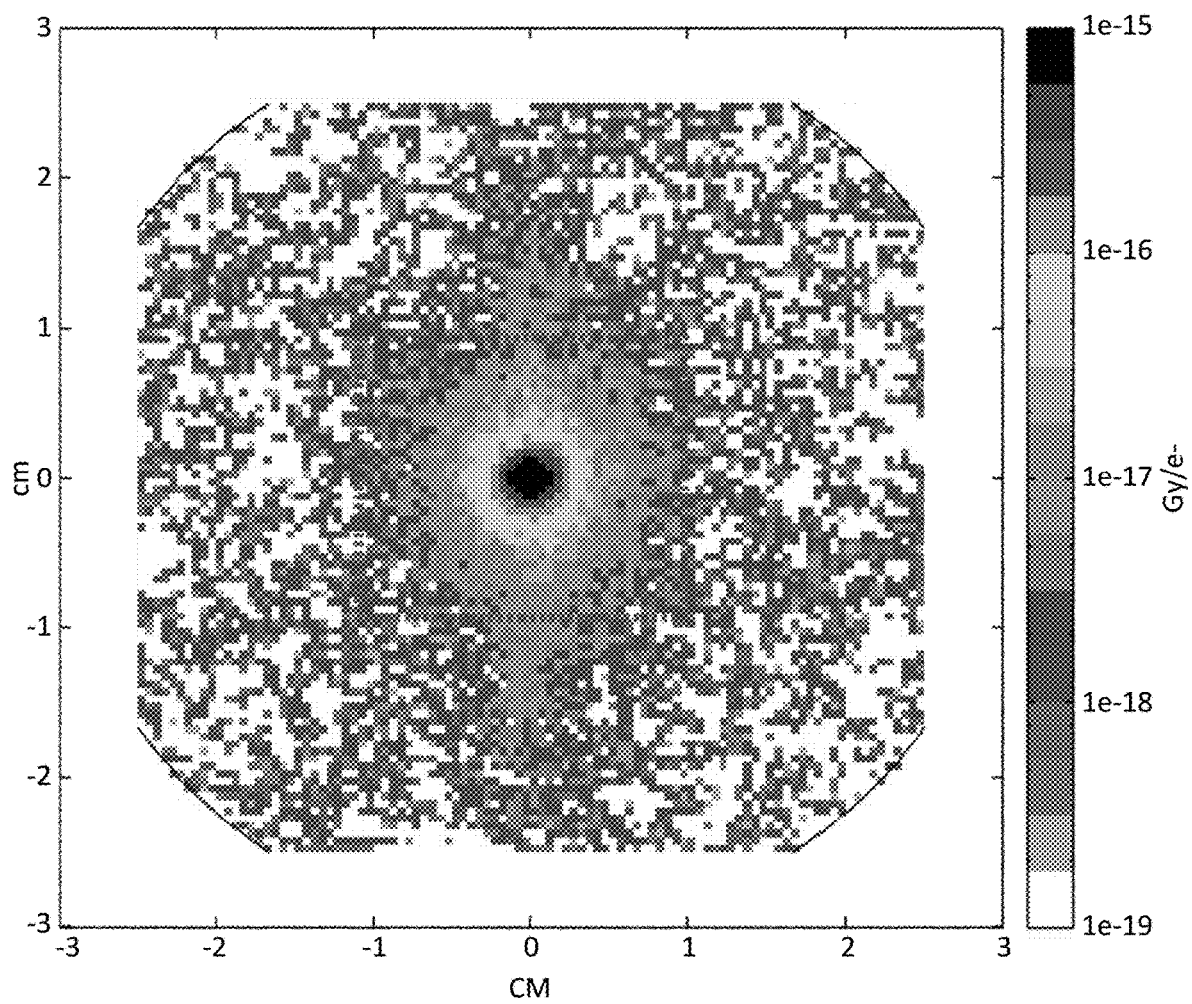
FIG. 17 shows the corresponding dose distribution at 1.5 cm depth in a water phantom in accordance with certain aspects of the invention.

FIG. 17 shows the corresponding dose distribution at 1.5 cm depth in a water phantom. In the example demonstrated, there is a sharp dose profile of 3 mm width and 2 mm penumbra. A small amount of cross-channel leakage is evident as side wings on the dose distribution with an intensity of approximately 1% of the central peak dose. This is approximately equal to the level of transmission through a typical MLC leaf but over a much smaller portion of the field. This demonstrates that the SPHINX design is able to produce spatially modulated beams with a higher degree of modulation and less leakage than MLCs, yet with no mechanical moving parts.

D. General

Numerous specific details are set forth herein to provide a thorough understanding of the claimed subject matter. However, those skilled in the art will understand that the claimed subject matter may be practiced without these specific details. In other instances, methods, apparatuses or systems that would be known by one of ordinary skill have not been described in detail so as not to obscure subject matter that may be claimed. Items in figures are not drawn to scale, unless otherwise indicated. When scale is indicated in drawings, the scale may illustrate the advantages of the invention in allowing a more compact system. It is understood, however, that the embodiments are not confined to the dimensions shown unless otherwise indicated.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art

What is claimed is:

1. A method for treating a patient, comprising:
generating one or more patterned particle beams, wherein each of the one or more patterned particle beams covers an area of the targeted tissue with spatially varying beam intensity according to a treatment pattern of desired radiation dose distribution;
accelerating the one or more patterned particle beams with one or more accelerators; and
transporting and/or magnifying the patterned beam to a desired location, direction, and size suitable for coverage of the targeted tissue, wherein a shape, resolution and contrast of the pattern is suitably maintained during transport and/or magnification so as to deliver the desired radiation dose distribution to the targeted tissue according to the treatment pattern.

2. The method of claim 1, wherein magnifying the patterned beam comprises magnifying the beam through one or more focusing elements disposed within the beamline of the one or more beams.

3. The method of claim 1, further comprising:
steering the one or more patterned particle beams to the targeted tissue with one or more beam steering devices from one or more directions.

4. The method of claim 1, wherein each of the one or more patterned particle beams comprise an array of smaller patterned beams.

5. The method of claim 1, wherein the patterned beam is magnified by up to 100 to 200 times an original size of the pattern of the one or more particle beams generated.

6. The method of claim 5, wherein a resolution of the treatment pattern at the original size is within 1/10 of a width of the overall pattern or smaller.

7. The method of claim 4, wherein the array of smaller patterned beams is produced by raster scanning individual smaller patterned beams from each beam direction of the one or more directions.

8. The method of claim 7, further comprising:
forming the two-dimensional intensity-modulated electron pattern on a photocathode by projecting or scanning a light source onto the photocathode.

9. A system for treating a patient, comprising:
one or more beam generation devices configured to generate one or more patterned particle beams, wherein each of the one or more particle beams covers an area of the targeted tissue with spatially varying beam intensity according to a treatment pattern of desired radiation dose distribution;
one or more accelerators configured for accelerating the one or more patterned particle beams; and
one or more magnification lenses along a beam line of the one or more particle beams between the one or more accelerators and the targeted tissue for magnification of the patterned particle beam to a desired size suitable for coverage of the targeted tissue according to the treatment pattern.

10. The system of claim 9, further comprising:
one or more beam steering devices configured for steering the one or more patterned particle beams to the targeted tissue from one or more directions.

11. The system of claim 10, wherein the system is configured such that steering of the one or more patterned particle beams is performed concurrent with magnifying the respective one or more pattern particle beams.

12. The system of claim 9, wherein the one or more magnification lenses comprise a plurality of lenses.

13. The system of claim 12, wherein a first magnetic lenses of the plurality along the beamline has a substantially higher strength than subsequent magnetic lenses of the plurality.

14. The system of claim 9, further comprising:
a beam deflector disposed between beamlines of the one or more particle beams between the one or more accelerators and the targeted tissue such that the one or more beam lines can be directed to the targeted tissue from multiple differing angles using a single common accelerator.

15. The system of claim 9, wherein the system is configured such that the one or more patterned particle beams comprises an array of smaller patterned beams.

16. The system of claim 15, wherein the system is configured such that the array of smaller patterned beams is produced by raster scanning individual smaller patterned beams from each beam direction.

17. The system of claim 9, further comprising:
an RF powered or DC particle gun and a photo-cathode configured to produce the two-dimensional intensity-modulated electron pattern.

18. The system of claim 9, wherein the system is configured such that the one or more patterned beams comprise multiple patterned beams so that, when delivered from multiple directions, the multiple beams produce a desired three-dimensional dose distribution when summed across the multiple beam directions.

19. The system of claim 9, further comprising:
a controller configured to control delivery of the one or more particle beams to the targeted tissue from the one or more directions thereby irradiating the targeted tissue to deliver an entire treatment dose in less than 10 seconds.

20. The system of claim 19, wherein the controller is configured to rapidly switch a modulation pattern sent to the photocathode within a rate of one pattern every 2 seconds or faster so as to provide delivery of differing treatment patterns to the targeted tissue from multiple directions within less than 10 seconds.

21. The system of claim 9, wherein the treatment pattern is adapted so as to be suitable for use in a non-medical application.

* * * * *

UNITED STATES PATENT AND TRADEMARK OFFICE
CERTIFICATE OF CORRECTION

| | | |
|---|---|---|
| PATENT NO. | : 10,576,303 B2 | Page 1 of 1 |
| APPLICATION NO. | : 15/896407 | |
| DATED | : March 3, 2020 | |
| INVENTOR(S) | : Vinod Bharadwaj et al. | |

It is certified that error appears in the above-identified patent and that said Letters Patent is hereby corrected as shown below:

In the Specification

Column 1, Line 23 add:
STATEMENT OF GOVERNMENT SPONSORED SUPPORT
This invention was made with Government support under contract DE-AC02-76SF00515 awarded by the Department of Energy. The Government has certain rights in the invention.

Signed and Sealed this
Seventh Day of May, 2024

Katherine Kelly Vidal
*Director of the United States Patent and Trademark Office*